United States Patent
Miyata et al.

(10) Patent No.: US 10,950,799 B2
(45) Date of Patent: Mar. 16, 2021

(54) ORGANIC ELECTROLUMINESCENT ELEMENT, DISPLAY DEVICE, LIGHTING DEVICE, PI-CONJUGATED COMPOUND, AND LIGHT-EMITTING THIN FILM

(71) Applicant: Konica Minolta, Inc., Tokyo (JP)

(72) Inventors: Yasuo Miyata, Yokohama (JP); Taketo Namikawa, Osaka (JP); Hiroshi Kita, Hachioji (JP)

(73) Assignee: Merck Patent GmbH, Darmstadt (DE)

( * ) Notice: Subject to any disclaimer, the term of this patent is extended or adjusted under 35 U.S.C. 154(b) by 425 days.

(21) Appl. No.: 15/329,851

(22) PCT Filed: Jul. 30, 2015

(86) PCT No.: PCT/JP2015/071638
§ 371 (c)(1),
(2) Date: Jan. 27, 2017

(87) PCT Pub. No.: WO2016/017757
PCT Pub. Date: Feb. 4, 2016

(65) Prior Publication Data
US 2017/0271597 A1 Sep. 21, 2017

(30) Foreign Application Priority Data
Jul. 31, 2014 (JP) .............................. JP2014-155852

(51) Int. Cl.
| | | |
|---|---|---|
| H01L 51/00 | (2006.01) | |
| C07D 219/02 | (2006.01) | |
| C07D 241/46 | (2006.01) | |
| C07D 241/48 | (2006.01) | |
| C07D 265/38 | (2006.01) | |

(Continued)

(52) U.S. Cl.
CPC ........ *H01L 51/0072* (2013.01); *C07D 209/86* (2013.01); *C07D 219/02* (2013.01); *C07D 241/46* (2013.01); *C07D 241/48* (2013.01); *C07D 265/38* (2013.01); *C07D 279/22* (2013.01); *C07D 307/91* (2013.01); *C07D 333/76* (2013.01); *C07D 401/10* (2013.01); *C07D 401/12* (2013.01); *C07D 403/10* (2013.01); *C07D 403/12* (2013.01); *C07D 409/10* (2013.01); *C07D 413/14* (2013.01); *C07D 417/10* (2013.01); *C07D 487/04* (2013.01); *C07F 5/02* (2013.01); *C07F 5/027* (2013.01); *C07F 7/0812* (2013.01); *C07F 7/10* (2013.01); *C09K 11/06* (2013.01); *H01L 51/008* (2013.01); *H01L 51/0071* (2013.01); *H01L 51/0094* (2013.01); *H01L 51/5004* (2013.01); *H05B 33/20* (2013.01); *C09K 2211/1018* (2013.01); *C09K 2211/1022* (2013.01); *H01L 51/0067* (2013.01); *H01L 51/0074* (2013.01); *H01L 51/0085* (2013.01);

(Continued)

(58) Field of Classification Search
CPC ............. H01L 51/0072; H01L 51/5004; H01L 51/0067; H01L 51/0074; H01L 2251/552; H01L 51/5016; H01L 51/5028; H01L 51/0071; H01L 51/0094; H01L 51/008; H01L 51/0085; H01L 2251/5376; H01L 51/50; C07D 209/86; C07D 279/22; C07D 265/38; C07D 487/04; C07D 417/10; C07D 241/46; C07D 409/10; C07D 403/10; C07D 401/10; C07D 333/76; C07D 403/12; C07D 307/91; C07D 401/12; C07D 241/48; C07D 219/02; C07D 413/14; C07F 5/027; C07F 7/0812; C07F 7/10; C07F 5/02; H05B 33/20; C09K 2211/1018; C09K 2211/1022; C09K 11/06
USPC ......................................................... 428/690
See application file for complete search history.

(56) References Cited

U.S. PATENT DOCUMENTS

| | | | |
|---|---|---|---|
| 2001/0021478 A1* | 9/2001 | Shi ........................ | H01L 51/005 430/57.1 |
| 2015/0141642 A1* | 5/2015 | Adachi ................. | C07C 317/36 544/102 |

(Continued)

FOREIGN PATENT DOCUMENTS

| | | |
|---|---|---|
| CN | 103848822 A | 6/2014 |
| JP | 2011-153201 A | 8/2011 |

(Continued)

OTHER PUBLICATIONS

CAS reg. No. 855828-26-1, Jul. 18, 2005. (Year: 2005).*
(Continued)

*Primary Examiner* — Douglas J McGinty
(74) *Attorney, Agent, or Firm* — Lucas & Mercanti, LLP

(57) ABSTRACT

An object of the present invention is to provide an organic electroluminescent element containing an organic layer interposed between an anode and a cathode, the organic layer containing at least one light emitting layer, wherein the at least one light emitting layer contains a π-conjugated compound having an electron donor portion and an electron acceptor portion in the molecule; the π-conjugated compound has a direction vector from an atom having a HOMO orbital in the electron donor portion to an electron cloud of the HOMO orbital, and a direction vector from an atom having a LUMO orbital in the electron acceptor portion to an electron cloud of the LUMO orbital, and the two direction vectors form an angle θ in the range of 90 to 180 degrees; and the π-conjugated compound has a plurality of the electron donor portions or a plurality of the electron acceptor portions.

12 Claims, 11 Drawing Sheets

(51) Int. Cl.

| | | |
|---|---|---|
| *C07D 279/22* | (2006.01) | |
| *C07D 307/91* | (2006.01) | |
| *C07D 333/76* | (2006.01) | |
| *C07D 401/10* | (2006.01) | |
| *C07D 401/12* | (2006.01) | |
| *C07D 403/10* | (2006.01) | |
| *C07D 403/12* | (2006.01) | |
| *C07D 409/10* | (2006.01) | |
| *C07D 413/14* | (2006.01) | |
| *C07D 417/10* | (2006.01) | |
| *C07D 487/04* | (2006.01) | |
| *C07F 5/02* | (2006.01) | |
| *C07F 7/08* | (2006.01) | |
| *C07F 7/10* | (2006.01) | |
| *C09K 11/06* | (2006.01) | |
| *H01L 51/50* | (2006.01) | |
| *H05B 33/20* | (2006.01) | |
| *C07D 209/86* | (2006.01) | |

(52) U.S. Cl.
CPC ...... *H01L 51/5016* (2013.01); *H01L 51/5028* (2013.01); *H01L 2251/5376* (2013.01); *H01L 2251/552* (2013.01)

(56) References Cited

U.S. PATENT DOCUMENTS

| | | | |
|---|---|---|---|
| 2016/0268516 A1* | 9/2016 | Tanaka | ............... H01L 51/0072 |
| 2018/0212157 A1* | 7/2018 | Oshiyama | ............ C07D 403/12 |

FOREIGN PATENT DOCUMENTS

| | | | |
|---|---|---|---|
| JP | 2013116975 | A | 6/2013 |
| JP | 2013179291 | A | 9/2013 |
| KR | 10-2014-0045368 | A | 4/2014 |
| KR | 10-2014-0076521 | A | 6/2014 |
| WO | 2005062675 | A1 | 7/2005 |
| WO | 2010134350 | A1 | 11/2010 |
| WO | 2013161437 | A1 | 10/2013 |
| WO | 2014157619 | A1 | 10/2014 |

OTHER PUBLICATIONS

CAS reg. No. 1477512, Nov. 20, 2013. (Year: 2013).*
CAS reg. No. 1873378-50-7, Feb. 24, 2016. (Year: 2016).*
English Translation of WO 2005062675, dated Jul. 7, 2005. (Year: 2005).*
IPRP dated Oct. 27, 2015 from corresponding International Application No. PCT/JP2015/071638; Applicant: Konica Minolta, Inc.; English translation of IPRP; Total of 11 pages.
Office Action dated Dec. 5, 2017 from corresponding Chinese Patent Application No. 201580041898.X and English translation.
Office Action dated May 9, 2018 from the corresponding Korean Patent Application No. KR 10-2017-7001500 and English translation.
Office Action dated Dec. 5, 2017 from corresporading Chinese Patent Appiication No. 201580041898.X and English transiation
Office Action dated Mar. 8, 2019 from the corresponding Korean Patent Application No. KR10-2017-7001500 and English translation.
Office Action dated Nov. 20, 2018 from the corresponding Korean Patent Application No. 10-2017-7001500 and English translation.
H. Uoyama, et al; Nature; vol. 492; 2012; pp. 234-238.
Q. Zhang, et al, Nature; Photonics; vol. 8; 2014, pp. 326-332.
H. Nakanotani, et al, Nature Communication; vol. 5; 2014, pp. 4016-4022.
International Search Report dated Oct. 27, 2015 for PCT/JP2015/071638 and English translation.
JPO, Office Action for the corresponding Japanese Patent Application No. 2016-538435, dated Jul. 30, 2019, with English translation.
JPO, Office Action for a related Japanese patent application No. 2016-538435, dated Feb. 12, 2020, with English translation (8 pages).
CNIPA, Office Action for a related Chinese patent application No. 201811293780.8, dated Mar. 30, 2020, with English translation (24 pages).

* cited by examiner a-1 
θ = 90° a-2 
θ = 135° a-3 
θ = 180° b 
θ = 45°

TADF compound

+

HOST compound

- D : Donor portion
- A : Acceptor portion
- ⌒ : Bond or Linking group

LIGHT

LIGHT

ORGANIC ELECTROLUMINESCENT ELEMENT, DISPLAY DEVICE, LIGHTING DEVICE, PI-CONJUGATED COMPOUND, AND LIGHT-EMITTING THIN FILM

CROSS REFERENCE TO RELATED APPLICATION

This Application is a 371 of PCT/JP2015/071638 filed on Jul. 30, 2015, which, in turn, claimed the priority of Japanese Patent Application No. JP 2014-155852 filed on Jul. 31, 2014, both applications are incorporated herein by reference.

TECHNICAL FIELD

The present invention relates to an organic electroluminescent element. Further, the present invention relates to a display device and a lighting device provided with the organic electroluminescent element, a π-conjugated compound and a light-emitting thin film containing the π-conjugated compound. More specifically, the present invention relates to an organic electroluminescent element achieving improved light emitting efficiency.

BACKGROUND

Organic electroluminescent (hereinafter referred to as "EL") elements (also referred to as "organic electroluminescence elements"), which are based on electroluminescence of organic materials, have already been put into practice as a new generation of light emitting systems capable of achieving planar light emission. Organic EL elements have recently been applied to electronic displays and also to lighting devices and display devices. Thus, it has been demanded further development of organic EL elements.

As an emission mode of an organic EL, there are two types. One is "a phosphorescence emission type" which emits light when a triplet excited state returns to a ground state, and another one is "a fluorescence emission type" which emits light when a singlet excited state returns to a ground state.

When an electric filed is applied to an organic EL element, a hole and an electron are respectively injected from an anode and a cathode, they are recombined in a light emitting layer to produce an exciton. At this moment, a singlet exciton and a triplet exciton are formed with a ratio of 25%:75%. Therefore, it is known that a phosphorescence emission type using a triplet exciton will produce theoretically high internal quantum efficiency compared with a fluorescence emission type.

However, in order to obtain high quantum efficiency in a phosphorescence emission type, it is required to use a complex compound having a rare metal of iridium or platinum in the center metal. This may induce an industrial problem of the amount of deposits or the cost of the rare metals in the future.

On the other hand, in recent years, new techniques relevant to a fluorescence emission type have been proposed to improve emission efficiency.

For example, Patent document 1 discloses a technique which is focused on a phenomenon wherein singlet excitons are generated by collision of two triplet excitons (it is called as Triplet-Triplet Annihilation (TTA), or Triplet-Triplet Fusion (TTF)), and which improves the emission efficiency of a fluorescent element by allowing the TTA phenomenon to occur effectively. Although this technique can increase power efficiency of a fluorescence emission material (hereafter, it is called as a fluorescent emission material or fluorescent material) from two to three times larger than the power efficiency of a conventional fluorescent material, the emission efficiency in TTA is not as high as that of the aforementioned phosphorescent material due to a theoretical limitation, because the rate of conversion of the excited triplet energy level to the excited singlet energy level will remain to about 40%.

Recent studies have disclosed a fluorescent material that employs a thermally activated delayed fluorescent mechanism (hereinafter also referred to as "TADF"). It is reported that it may be applied to an organic EL element (for example, refer to Patent document 2 and Non-patent documents 1 to 2). By making use of this delayed fluorescence caused by the TADF mechanism, theoretically, it is possible to achieve an internal quantum efficiency of 100% in fluorescence emission, which is similar to the phosphorescent emission.

In order to make appear the TADF phenomenon, it is required that a reverse intersystem crossing from the triplet state, which is produced with an amount of 75% by an electric field excitation in an amount of 75% at room temperature or at an emission layer temperature on the emission device, to the singlet state should be taken place. Further, by the mechanism that the singlet exciton produced by the reverse intersystem crossing emits fluorescence in the same way as the singlet exciton produced with an amount of 25%, it is theoretically possible to realize 100% internal quantum efficiency. In order to make appear this reverse intersystem crossing, it is necessary that the absolute value of the difference between the singlet excited level and the triplet excited level (hereafter, it is called as $\Delta E_{ST}$) is very small. To obtain a minimum $\Delta E_{ST}$ in an organic compound, it is preferable that a HOMO and a LUMO in the molecule are not mixed and localized respectively.

For example, in the case of 2CzPN illustrated in "a" of FIG. 1, a HOMO is localized at a carbazolyl group at the 1 position and the 2 position of the benzene ring, and a LUMO is localized at cyano groups at the 4 position and the 5 position. As a result, the HOMO and the LUMO of 2CzPN may be separated, and $\Delta E_{ST}$ becomes very small as indicated in "b" of FIG. 1. Thus a TADF phenomenon will be produced. On the other hand, in the case of 2CzXy ("a" of FIG. 2) which is produced by substituting cyano groups at the 4 position and the 5 position of 2CzPN with methyl groups, the HOMO and the LUMO cannot be clearly separated as is seen in 2CzPN. As a result, $\Delta E_{ST}$ cannot be made small, and a TADF phenomenon will not be produced.

Further, it is known that an addition of the third component (an assist-dopant compound) which exhibits a TADF property into a light emitting layer composed of a host compound and an emission compound is effective to achieve high efficiency (Non-patent document 3). By producing 25% of singlet exciton and 75% of triplet exciton via an electric field excitation on an assist-dopant compound, the triplet exciton will produce the singlet exciton through the reverse intersystem crossing (RISC). The energy of the singlet exciton will be moved to the emission compound via an energy transfer. It is possible that the emission compound emits light. Consequently, theoretically, it is possible to emit light from the emission compound by making use of 100% of the exciton. It may achieve high emission efficiency.

However, the localization of the HOMO and the LUMO, which is a requirement for making appear the TADF phenomenon, will form an excited state having an intermolecular charge transfer (CT) property. This will become a factor of broadening an absorption spectrum or an emission spectrum. This broadening phenomenon becomes a fatal problem for a color designing of an organic EL element. The reason of this problem will be described in the following, An electronic state of 2CzPN is schematically illustrated in "a" of FIG. 3. A molecule known as a TADF emission material (hereafter, it may be called as "a TADF compound") has a localized HOMO and a localized LUMO, and it has an imbalanced charge in the molecule. This charge imbalance will induce imbalance in the medium substance (for example, a solvent or a host compound, see "b" of FIG. 3). Therefore, as indicated in "c" of FIG. 3, the medium substance will be electrostatically adsorbed to the TADF compound. Interactions will be formed at a variety of positions and directions. As a result, an energy distribution in the excited state of the TADF compound will be spread, and it is known that an absorption spectrum or an emission spectrum will be broadened.

On the other hand, FIG. 4 illustrates a schematic diagram of an interaction between a phosphorescent compound and a host compound. As illustrated in "a" of FIG. 4, the phosphorescent compound (Ir(ppy)$_3$) has a localized HOMO and a localized LUMO respectively placed in the inner portion and in the outer portion of the molecule. Since the HOMO portion exists substantially at an iridium metal in the center of the complex, it will not contribute to an electrostatic interaction with the surrounding medium. The LUMO distributed in the ligand will interact with the host compound ("b" of FIG. 4). Since it is localized in the outer side of the molecule, the location and direction of the interaction will be limited. Consequently, an energy distribution in the excited state of the phosphorescent compound will be restrained, and broadening of an absorption spectrum and an emission spectrum will become small compared with a conventional TADF compound ("c" of FIG. 4).

Accordingly, it is required a new molecular design for a TADF compound enabling to restrain an energy distribution in the excited state as the phosphorescent compound. A conventional organic EL element has not achieved all of the following properties at the same time: restrain of broadening of an absorption spectrum and an emission spectrum, high emission efficiency, and non-use of a rare metal.

PRIOR ART DOCUMENTS

Patent Documents

Patent document 1: WO 2010/134350
Patent document 2: JP-A No. 2013-116975

Non-Patent Documents

Non-patent document 1: I. Uoyama, et al., Nature, 2012, 492, 234-238.
Non-patent document 2: Q. Mang et al., Nature, Photonics, 2014, 8, 326--332.
Non-patent document 3: H. Nakanotani, et al., Nature Communication, 2014, 5, 4016-4022.

SUMMARY OF THE INVENTION

Problems to be Solved by the Invention

The present invention has been made in view of the above-described problems and situation. An object of the present invention is to provide an organic electroluminescent element enabling to achieve restrained broadening of an absorption spectrum and an emission spectrum, and high emission efficiency without using a rare metal. An object of the present invention is to provide a display device and a lighting device provided with the organic electroluminescent element. Further, an object of the present invention is to provide a π-conjugated compound enabling to achieve restrained broadening of an absorption spectrum and an emission spectrum, and high emission efficiency without using a rare metal, and a light-emitting thin film containing the π-conjugated compound.

Means to Solve the Problems

The present inventors have investigated the cause of the above-described problems in order to solve the problems. It was found to provide an organic EL element capable of improving emission efficiency by incorporating a specific π-conjugated compound having a donor portion and an acceptor portion each being placed in a specific positional relationship in the molecule in at least one of the light-emitting layer.

That is, the above-described problems of the present invention are solved by the following embodiments.

1. An organic electroluminescent element comprising an organic layer interposed between an anode and a cathode, the organic layer containing at least one light emitting layer, wherein the at least one light emitting layer contains a π-conjugated compound having an electron donor portion and an electron acceptor portion in the molecule;

the π-conjugated compound has a direction vector from an atom having a HOMO orbital in the electron donor portion to an electron cloud of the HOMO orbital, and a direction vector from an atom having a LUMO orbital in the electron acceptor portion to an electron cloud of the LUMO orbital, and the two direction vectors form an angle θ in the range of 90 to 180 degrees; and the π-conjugated compound has at least one of a plurality of the electron donor portions and a plurality of the electron acceptor portions.

2. The organic electroluminescent element described in the embodiment 1, wherein the angle θ is in the range of 135 to 180 degrees.

3. The organic electroluminescent element described in the embodiments 1 or 2, wherein one of the electron acceptor portions is bonded to two or more electron donor portions through a linking group, or one of the electron donor portions is bonded to two or more electron acceptor portions through a linking group.

4. The organic electroluminescent element described in the embodiments 1 or 2, wherein one of the electron acceptor portions is directly bonded to two or more electron donor portions, or one of the electron donor portions is directly bonded to two or more electron acceptor portions.

5. The organic electroluminescent element described in any one of the embodiments 1 to 4, wherein the at least one light emitting layer contains a π-conjugated compound represented by any one of Formulas (1) to (8).

Formula (1)

Formula (2)

Formula (3)

Formula (4)

$$Y^{10}-X^4-Y^{12}$$
$$\quad\ \ |$$
$$\quad Y^{13}$$
$$\quad\ Y^{11}$$

Formula (5)

$$Y^{14}\diagdown\quad\diagup Y^{15}$$
$$\quad X^5$$
$$\quad\ |$$
$$\quad Y^{16}$$

Formula (6)

$$Y^{17}-X^6-Y^{18}$$

Formula (7)

Formula (8)

$$Y^{20}-X^8$$

In Formulas, $X^1$ to $X^8$ and $Y^1$ to $Y^{20}$ each respectively represent the electron donor portion or the electron acceptor portion; when $X^1$ to $X^8$ each respectively represent the electron donor portion, $Y^1$ to $Y^{20}$ each respectively represent the electron acceptor portion; when $X^1$ to $X^8$ each respectively represent the electron acceptor portion, $Y^1$ to $Y^{20}$ each respectively represent the electron donor portion; $L^1$ to $L^{10}$ represent a linking group, $L^1$ to $L^{10}$ each respectively represent an aryl group which may have a substituent or a heteroaryl group which may have a substituent, $L^1$ binds $X^1$ and $Y^1$ through adjacent carbon atoms, $L^2$ binds $X^1$ and $Y^2$ through adjacent carbon atoms, $L^3$ binds $X^1$ and $Y^3$ through adjacent carbon atoms, $L^4$ binds $X^1$ and $Y^4$ through adjacent carbon atoms, $L^5$ binds $X^2$ and $Y^5$ through adjacent carbon atoms, $L^6$ binds $X^2$ and $Y^6$ through adjacent carbon atoms, $L^7$ binds $X^2$ and $Y^7$ through adjacent carbon atoms, $L^8$ binds $X^3$ and $Y^8$ through adjacent carbon atoms, $L^9$ binds $X^3$ and $Y^9$ through adjacent carbon atoms, and $L^{10}$ binds $X^7$ and $Y^{19}$ through adjacent carbon atoms.

6. The organic electroluminescent element described in the embodiment 5, wherein the electron donor portion and the electron acceptor portion represented by to $X^8$ and to $Y^{20}$ in Formulas (1) to (8) each respectively are one selected from the group consisting of an aryl group which may have a substituent, a heteroaryl group which may have a substituent, an alkyl group which may have a substituent, a carbonyl group which may have a substituent, a nitrogen atom which may have a substituent, a sulfur atom which may have a substituent, a boron atom which may have a substituent, a phosphor atom which may have a substituent, an oxygen atom which may have a substituent, and a silicon atom which may have a substituent.

7. The organic electroluminescent element described in the embodiments 5 or 6,
wherein $L^1$ to $L^{10}$ in Formulas (1) to (3) and (7) each are a benzene ring.

8. The organic electroluminescent element described in any one of the embodiments 1 to 7,
wherein an absolute value of a difference between a lowest excited singlet energy level and a lowest excited triplet energy level ($\Delta E_{ST}$) is 0.5 eV or less.

9. The organic electroluminescent element described in any one of the embodiments 1 to 8,
wherein the at least one light emitting layer contains: the π-conjugated compound; and at least one of a fluorescent compound and a phosphorescent compound.

10. The organic electroluminescent element described in any one of the embodiments 1 to 9,
wherein the at least one light emitting layer contains: the π-conjugated compound; at least one of a fluorescent compound and a phosphorescent compound; and a host compound.

11. A display device provided with the organic electroluminescent element described in any one of the embodiments 1 to 10.

12. A lighting device provided with the organic electroluminescent element described in any one of the embodiments 1 to 10.

13. A π-conjugated compound having an electron donor portion and an electron acceptor portion in the molecule,
wherein the π-conjugated compound has a direction vector from an atom having a HOMO orbital in the electron donor portion to an electron cloud of the HOMO orbital, and a direction vector from an atom having a LUMO orbital in the electron acceptor portion to an electron cloud of the LUMO orbital, and the two direction vectors form an angle θ in the range of 90 to 180 degrees; and the π-conjugated compound has a plurality of the electron donor portions or a plurality of the electron acceptor portions.

14. A light-emitting thin film containing the π-conjugated compound described in the embodiment 13.

Effects of the Invention

By the above-described embodiments of the present invention, it is possible to provide an organic electroluminescent element enabling to achieve restrained broadening of an absorption spectrum and an emission spectrum, and high emission efficiency without using a rare metal. It is also possible to provide a display device and a lighting device provided with the organic electroluminescent element. Further, it is possible to provide a π-conjugated compound enabling to achieve restrained broadening of an absorption spectrum and an emission spectrum, and high emission efficiency without using a rare metal, and a light-emitting thin film containing the π-conjugated compound.

A formation mechanism or an action mechanism of the effects of the present invention is not clearly identified, but it is supposed as follows.

The present invention is specifically effective when the above-described angle θ is in the range of 90 to 180 degrees.

In FIG. 5, "a-1" to "a-3" and "b" each are a schematic drawing illustrating a π-conjugated compound containing one electron donor portion and one electron acceptor portion for convenience. It will be described the case in which the angle θ formed with a direction vector of a donor portion and a direction vector of an acceptor portion is in the range of the present invention, and the case in which the angle θ is outside the range of the present invention by making use of these "a-1" to "a-3" and "b" in FIG. 5. Here, arrows in "a-1" to "a-3" and "b" of FIG. 5 each represent: a direction vector from an atom having a HOMO orbital in the electron donor portion to an electron cloud of the HOMO orbital; or a direction vector from an atom having a LUMO orbital in the electron acceptor portion to an electron cloud of the LUMO orbital.

In "a-1" to "a-3" of FIG. 5 indicating the angle θ in the range of the present invention, an electron transfer in space will easily occur from a HOMO of the donor portion to a LUMO of the acceptor portion. As a result, high emission efficiency will be achieved in an organic EL element. On the other hand, when the angle θ is outside the range of the present invention as illustrated in "b" of FIG. 5, an electron transfer in space will hardly occur from the HOMO of the donor portion to the LUMO of the acceptor portion. As a result, high emission efficiency will not be achieved.

In the following, it will be described the restraining effect of broadening of an absorption spectrum or an emission spectrum. In "a" of FIG. 6, there is illustrated for convenience a simplified schematic drawing of a π-conjugated compound containing one electron donor portion and two electron acceptor portions, and having an angle θ within the range of the present invention. A HOMO distributed in a donor portion of a TADF compound is facing to a LUMO in an acceptor portion. There is no space where the HOMO will interact with the surrounding medium. Consequently, as illustrated in "b" of FIG. 6, the position and the direction of the interaction between the π-conjugated compound (the TADF molecule) of the present invention and the medium (the host compound) will be limited compared with the case of "c" in FIG. 3. As a result, it is produced a restraining effect of broadening of an absorption spectrum or an emission spectrum.

EMBODIMENTS TO CARRY OUT THE INVENTION

Figure 1:
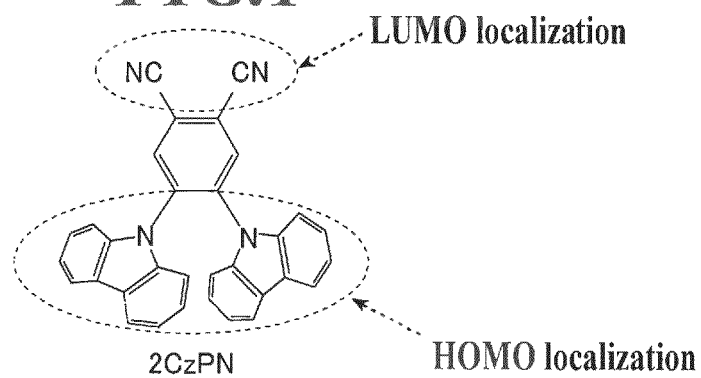
FIG. 1 is an energy diagram illustrating $\Delta E_{ST}$.
Figure 1:
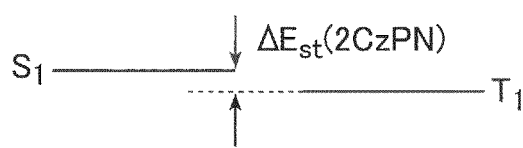
Figure 1:
Figure 2:
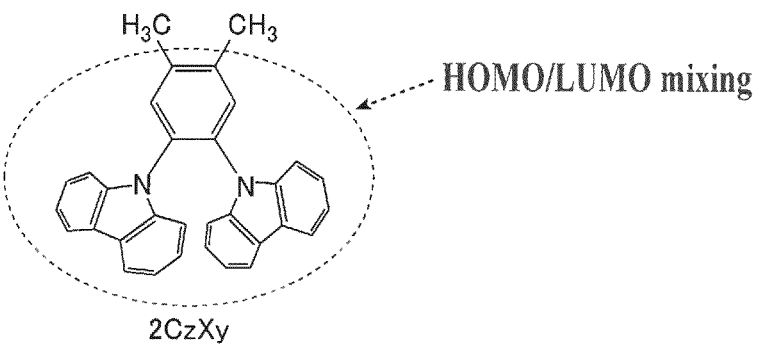
FIG. 2 is another example of an energy diagram illustrating $\Delta E_{ST}$.
Figure 2:
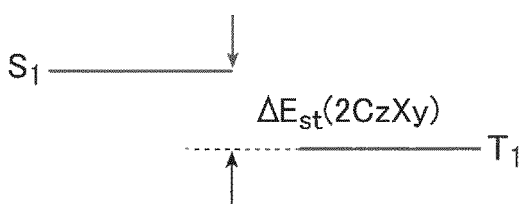
Figure 2:

An organic electroluminescent element of the present invention is characterized in having the following features. It comprises an organic layer interposed between an anode and a cathode, the organic layer containing at least one light emitting layer, wherein the at least one light emitting layer contains a π-conjugated compound having an electron donor portion and an electron acceptor portion in the molecule; the π-conjugated compound has a direction vector from an atom having a HOMO orbital in the electron donor portion to an electron cloud of the HOMO orbital, and a direction vector from an atom having a LUMO orbital in the electron acceptor portion to an electron cloud of the LUMO orbital, and the two direction vectors form an angle θ in the range of 90 to 180 degrees; and the π-conjugated compound has a plurality of the electron donor portions or a plurality of the electron acceptor portions.

The above-described features are technical features commonly owned by the invention according to the embodiments 1 to 14.

From the viewpoint of obtaining an effect of the present invention, a preferable embodiment of the present invention is that the above-described angle θ is in the range of 135 to 180 degrees. By this embodiment, an electron transfer in space will easily occur from the donor portion to the acceptor portion. As a result, emission efficiency will be further improved. This is a preferable embodiment.

A preferable embodiment of the present invention is that one of the electron acceptor portions is bonded to two or more electron donor portions through a linking group, or one of the electron donor portions is bonded to two or more electron acceptor portions through a linking group. This embodiment will restrain broadening of an absorption spectrum or an emission spectrum.

Another preferable embodiment of the present invention is that one of the electron acceptor portions is directly bonded to two or more electron donor portions, or one of the electron donor portions is directly bonded to two or more electron acceptor portions. This embodiment will restrain broadening of an absorption spectrum or an emission spectrum.

Another preferable embodiment of the present invention is that the at least one light emitting layer contains a π-conjugated compound represented by any one of Formulas (1) to (8). This embodiment is preferable from the viewpoint of achieving high emission efficiency.

Another preferable embodiment of the present invention is that the electron donor portion and the electron acceptor portion represented by $X^1$ to $X^8$ and $Y^1$ to $Y^{20}$ in Formulas (1) to (8) each respectively are one selected from the group consisting of an aryl group which may have a substituent, a heteroaryl group which may have a substituent, an alkyl group which may have a substituent, a carbonyl group which may have a substituent, a nitrogen atom which may have a substituent, a sulfur atom which may have a substituent, a boron atom which may have a substituent, a phosphor atom which may have a substituent, an oxygen atom which may have a substituent, and a silicon atom which may have a substituent. This embodiment is preferable from the viewpoint of achieving high emission efficiency.

Another preferable embodiment of the present invention is that $L^1$ to $L^{10}$ in Formulas (1) to (3) and (7) each are a benzene ring. This embodiment is preferable from the viewpoint of achieving high emission efficiency.

Another preferable embodiment of the present invention is that an absolute value of a difference between a lowest excited singlet energy level and a lowest excited triplet energy level ($\Delta E_{ST}$) is 0.5 eV or less. This embodiment is preferable from the viewpoint of easily achieving an intersystem crossing.

Another preferable embodiment of the present invention is that the at least one light emitting layer contains: the π-conjugated compound; and at least one of a fluorescent compound and a phosphorescent compound. This embodiment is preferable from the viewpoint of achieving high emission efficiency.

Another preferable embodiment of the present invention is that the at least one light emitting layer contains: the π-conjugated compound; at least one of a fluorescent compound and a phosphorescent compound; and a host compound. This embodiment is preferable from the viewpoint of achieving high emission efficiency.

An organic electroluminescent element of the present invention is suitably incorporated in a display device. This is a preferable embodiment because a display device having high emission efficiency will be obtained.

An organic electroluminescent element of the present invention is suitably incorporated in a lighting device. This is a preferable embodiment because a lighting device having high emission efficiency will be obtained.

A π-conjugated compound of the present invention is characterized in having an electron donor portion and an electron acceptor portion in the molecule, wherein the π-conjugated compound has a direction vector from an atom having a HOMO orbital in the electron donor portion to an electron cloud of the HOMO orbital, and a direction vector from an atom having a LUMO orbital in the electron acceptor portion to an electron cloud of the LUMO orbital, and the two direction vectors form an angle θ in the range of 90 to 180 degrees; and the π-conjugated compound has at least one of a plurality of the electron donor portions and a plurality of the electron acceptor portions. It may be provided a material having high emission efficiency by this embodiment.

A π-conjugated compound of the present invention may be suitably incorporated in a light-emitting thin film. It will be obtained a light-emitting thin film having high efficiency by this embodiment.

The present invention and the constitution elements thereof, as well as configurations and embodiments, will be detailed in the following. In the present description, when two figures are used to indicate a range of value before and after "to", these figures are included in the range as a lowest limit value and an upper limit value.

<Light Emission Mode of Organic EL>

As a light emission mode of an organic EL, there are two types. One is "a phosphorescence emission type" which emits light when a triplet excited state returns to a ground state, and another one is "a fluorescence emission type" which emits light when a singlet excited state returns to a ground state.

When excitation is done by an electric field such as in the case of an organic EL element, a triplet exciton is produced with a probability of 75%, and a singlet exciton is produced with a probability of 25%. Consequently, it is possible that a phosphorescent emission has higher emission efficiency than fluorescent emission. The phosphorescent emission is an excellent mode to realize low electric consumption.

On the other hand, with respect to the fluorescent emission, it was found a method of using a TTA mechanism in which singlet excitons are generated from two triplet excitons (it is called as Triplet-Triplet Annihilation (TTA), or Triplet-Triplet Fusion (TTF)) to improve the emission efficiency. The TTA mechanism may be achieved by the triplet excitons produced with a probability of 75%, which will normally take the route of radiationless deactivation only to produce heat. By making the triplet excitons to be produced in a high density, the TTA mechanism is effective.

In recent years, the group of Adachi found the following phenomenon. By achieving a small energy gap between the singlet excited state and the triplet excited state, it is allowed to occur a reverse intersystem crossing from the triplet state of lower energy level to the singlet state. This may be done by the Joule heat produced during the emission and/or the environmental temperature in which the light emission element is placed. As a result, it may be achieved a fluorescent emission in a yield of nearly 100% (it is called as a thermally activated delayed fluorescence: TADF). And it was found a compound enabling to occur this phenomenon (refer to Non-patent document 1, for example).

<Phosphorescence Emission Material>

As described above, although the phosphorescence emission has theoretically an advantage of 3 times of the fluorescence emission, an energy deactivation (=phosphorescence emission) from the triplet excited state to the singlet ground state is a forbidden transition. In the same manner, the intersystem crossing from the singlet excited state to the triplet excited state is also a forbidden transition. Consequently, its rate constant is usually small. That is, since the transition takes place hardly, the lifetime of the exciton becomes long such as an order of millisecond or second. As a result, it is difficult to obtain a required emission.

However, when an emission occurs from a complex including a heavy atom of iridium or platinum, the rate constant of the above-described forbidden transition becomes larger by 3 orders due to the heavy metal effect of the center metal. It is possible to obtain a phosphorescence quantum efficiency of 100% when selection of the ligand is properly done.

However, in order to obtain an ideal emission, it is required to use a rare metal such as iridium or palladium, or a noble metal such as platinum. If a large amount of these metals are used, the reserves and the price of these metal will become problem.

<Fluorescence Emission Material>

A common fluorescence emission material is not required to be a heavy metal complex as in the case of a phosphorescence emission material. It may be applied a so-called organic compound composed of a combination of elements such as carbon, oxygen, nitrogen and hydrogen. Further, a non-metallic element such as phosphor, sulfur, and silicon may be used. And a complex of typical element such as aluminum or zinc may be used. The variation of the materials is almost without limitation.

However, the conventional fluorescence emission material will use only 25% of the excitons to light emission. Therefore, it cannot be expected high emission efficiency as achieved in phosphorescence emission.

<Delayed Fluorescent Material>

[Excited Triplet-Triplet Annihilation (TTA) Delayed Fluorescent Material]

A light emission mode employing a delayed fluorescence appeared to solve the problem of the fluorescent material. The TTA mode originated from the collision of the compounds at a triplet state may be described in the following Scheme. That is, in the past, a part of the triplet exciton is only converted to heat. This energy of the exciton is changed to a singlet exciton via an intersystem crossing to result in contributing to the light emission. In a practical organic EL element, it was proved that external quantum efficiency was double of the conventional fluorescent element.

ti Scheme: $T^*+T^* \rightarrow S^*+S$ (In the Scheme, T* represents a triplet exciton, S* represents a singlet exciton, and S represents a ground state molecule.)

However, as can be seen from the above-described Scheme, only one singlet exciton is generated from two triplet excitons. Consequently, theoretically, 100% internal quantum efficiency cannot be obtained based on this mode.

[Thermally Activated Delayed Fluorescent (TADF) Compound]

A TADF mode, which is another type of high efficient fluorescence emission, is a mode enabling to resolve the problem.

A fluorescent material has an advantage of being molecular-designed without imitation as described above. Among the molecular-designed compounds, there are specific compounds having an energy level difference (hereafter, it is indicated as $\Delta E_{ST}$) between a triplet excited state and a singlet excited state being in very close vicinity (refer to "a" in FIG. 1).

In spite of that fact that these compounds don't contain a heavy metal atom in the molecule, there occurs a reverse intersystem crossing reaction from the triplet excited state to the singlet excited state due to the small $\Delta E_{ST}$ value. This reaction will not usually occur. Further, since the rate constant of the deactivation from the singlet excited state to the ground state (=fluorescence emission) is extremely high, the triplet state will likely return to the ground state via the singlet state while emitting fluorescence, instead of thermally deactivating (radiationless deactivation) to the ground state. As a result, in TADF mechanism, ideally, it is possible to realize fluorescence emission of 100%.

<Molecular Designing Idea Concerning $\Delta E_{ST}$>

A molecular designing idea to reduce the $\Delta E_{ST}$ will be described.

In order to reduce the value of $\Delta E_{ST}$, theoretically the most effective way is to minimize the spatial overlaps of the highest occupied molecular orbital (HOMO) and the lowest unoccupied molecular orbital (LUMO).

Generally, in the electronic orbitals of the molecule, it is known that HOMO has a distribution to an electron donating position and LUMO has a distribution to an electron withdrawing position. By introducing an electron donating structure and an electron withdrawing structure in the molecule, it is possible to keep apart the positions in which HOMO and LUMO exist.

For example, Applied Physics vol. 82, no. 6, 2013 "Organic Photo-electronics in the commercialization stage" discloses the following. By introducing an electron withdrawing structure such as a cyano group, a sulfonyl group or a triazine group, and an electron donating structure such as a carbazole group or a diphenyl amino group, LUMO and HOMO are respectively made localized.

In addition, it is also effective to minimize the molecular structure change between the ground state and the triplet excited state of the molecule. As a means to minimize the structure change, it can cite a compound having an inflexible structure. Here, inflexibility indicates the state in which freely movable portions in the molecule are not abundant caused by preventing a free rotation of the bond between the rings in the molecule, or by introducing a condensed ring having a large π-conjugate plane, for example. In particular, by making the portion participating in the light emission to be rigid, it is possible to minimize the molecular structure change in the excited state.

<Common Problem Possessed by TADF Compound>

A TADF compound possesses a variety of problems arisen from the aspects of the light emission mechanism and the molecular structure.

A part of common problems possessed by a TADF compound will be described in the following.

In a TADF compound, it is required to keep apart the portions in which HOMO and LUMO exist as much as possible in order to minimize $\Delta E_{ST}$. For this reason, the electronic state of the molecule becomes almost near the intra molecular CT state (intramolecular charge transfer state).

When a plurality of these molecules exist, these molecules will be stabilized by making in proximity the donor portion in one molecule and the acceptor portion in other molecule. This stabilized condition is formed not only with 2 molecules, but it may be formed with 3 and 5 molecules. Consequently, there are produced a variety of stabilized conditions having a broad distribution. The shape of absorption spectrum or the emission spectrum will be broad. Further, even if a multiple molecular aggregation of 2 or more molecules does not formed, there may be formed a variety of existing conditions having different interaction directions or angles of two molecules. As a result, basically, the shape of absorption spectrum or the emission spectrum will be broad.

When the emission spectrum becomes broad, it will generate two major problems. One is a problem of decreasing the color purity of the emission color. This is not so important when it is applied to an illumination use. However, when it is used for an electronic device, the color reproduction region becomes small. And the color reproduction of pure colors will become decreased. As a result, it is difficult to apply to a commercial product.

Another problem is the shortened wavelength of the rising wavelength in the short wavelength side of the emission spectrum (it is called as "fluorescent zero-zero band"). That is, the $S_1$ level becomes high (becoming higher energy level of the excited singlet energy).

When the fluorescent zero-zero band becomes shortened, the phosphorescent zero-zero band derived from $T_1$ (being lower than $S_1$) will become shortened (becoming higher $T_1$).

Therefore, the host compound is required to have high $S_1$ and high $T_1$ in order to prevent the reverse energy transfer from the dopant.

This is a major problem. A host compound basically made of an organic compound will take plural and unstable chemical species conditions such as a cationic radical state, an anionic radical state and an excited state in an organic EL element. These chemical species may be made existed in relatively stable condition by expanding a π-conjugate system in the molecule.

Further, in a TADF compound without containing a heavy metal, the transition from the triplet excited state to the ground state is forbidden transition. The existing time at the triplet excited state (exciton lifetime) is extremely long such as in an order of several hundred microsecond to millisecond. Therefore, even if the $T_1$ energy level of the host compound is higher than that of the light emitting material, it will be increased the probability of taking place a reverse energy transfer from the triplet excited state of the light emitting material to the host compound due to the long lifetime. As a result, it is difficult to sufficiently make occur a required reverse intersystem crossing from the triplet excited state to the singlet excited state of the TADF compound. Instead, there occurs an unrequired reverse energy transfer to the host compound as a major route to result in failure to obtain insufficient emission efficiency.

In order to solve the above-described problem, it is required to make sharp a shape of an emission spectrum of the TADF compound, and to decrease the difference between the emission maximum wavelength and the rise of the emission spectrum. This may be achieved basically by reducing the change of the molecular structure of the singlet excited state and the triplet excited state.

Further, in order to prevent the reverse energy transfer to the host compound, it is effective to shorten the existing time of the triplet excited state of the TADF compound (exciton lifetime). In order to realize this, the possible ways to solve the problem are: to minimize the molecular structure change between the ground state and the triplet excited state; and to introduce a suitable substituent or an element to loosen the forbidden transition.

It will be described a variety of measuring methods concerning a π-conjugated compound according to the present invention.

[Electron Density Distribution]

From the viewpoint of decreasing $\Delta E_{ST}$, it is preferable that a π-conjugated compound according to the present invention has a HOMO and a LUMO substantially separated with each other in the molecule. The distribution state of the HOMO and the LUMO may be obtained from the electron density distribution in the optimized structure by a molecular orbital calculation.

The structure optimization and the calculation of the electron density distribution of the π-conjugated compound of the present invention with a molecular orbital calculation may be done by employing a software of a molecular orbital calculation using B3LYP as a functional and 6-31G(d) as a base function for a calculation method. There is no limitation to the software, the same results may be obtained with any software.

In the present invention, as a molecular orbital calculation software, it was used Gaussian 09 made by The US Gaussian Inc., (Revision C.01, by M. J. Frisch et al., Gaussian Inc., 2010).

Here, the condition of "a HOMO and a LUMO being substantially separated" indicates the state in which the center portion of the HOMO orbital distribution and the center portion of the LUMO orbital distribution calculated with the above-described molecular calculation method are separated. More preferably, the HOMO orbital distribution and the LUMO orbital distribution are substantially not superimposed.

The separation state of the electron density distribution of the HOMO and the LUMO may be determined by making calculation of excited states with a Time-dependent DFT method starting from the optimized structure calculation using B3LYP as a functional and 6-31G (d) as abase function as described above. The excited state energy levels of $S_1$ and $T_1$ are obtained, and $\Delta E_{ST}$ is calculated from the scheme of: $\Delta E_{ST}=E(S_1)-E(T_1)$. The smaller the calculated $\Delta E_{ST}$, it indicates that the HOMO and the LUMO are more separated. In the present invention, an absolute value of $\Delta E_{ST}$ obtained by the above-described calculation method is preferably 0.5 eV or less, more preferably it is 0.2 eV or less, and still more preferably it is 0.1 eV or less.

[Lowest Excited Singlet Energy Level $S_1$]

In the present invention, the lowest excited singlet energy S1 of the π-conjugated compound of the present invention may be determined by a common technique. Specifically, a target compound is deposited onto a quartz substrate to prepare a sample, and an absorption spectrum of the sample is measured at ambient temperature (300 ) (vertical axis: absorbance, horizontal axis: wavelength). A tangential line is drawn at the rising point of the absorption spectrum on the longer wavelength side, and the lowest excited singlet energy is calculated by a specific conversion expression on the basis of the wavelength at the point of intersection of the tangential line with the horizontal axis.

When the π-conjugated compound used in the present invention has a high aggregation property as a molecule itself, it is likely to cause molecular aggregation, and thus a thin film prepared from the compound may cause a measurement error due to molecular aggregation. In the present invention, the lowest excited singlet energy level is determined from, as an approximation, the peak wavelength of emission of a solution of the π-conjugated compound at room temperature (about 25° C.) in consideration of a relatively small Stokes shift of the π-conjugated compound and a very small structural change of the compound between the excited state and the ground state. This determination process may use a solvent which does not affect the molecular aggregation state of the π-conjugated compound; for example, a non-polar solvent having a small solvent effect, such as cyclohexane or toluene.

[Lowest Excited Triplet Energy Level $T_1$]

The lowest excited triplet energy level ($T_1$) of the π-conjugated compound of the present invention is determined on the basis of the photoluminescent (PL) properties of a solution or thin film of the compound. For example, a thin film is prepared from a dilute dispersion of the π-conjugated compound, and the transient PL properties of the thin film are determined with a streak camera for separation of a fluorescent component and a phosphorescent component to determine the absolute value of the energy difference $\Delta E_{ST}$ therebetween. The lowest excited triplet energy level may be obtained from the lowest excited singlet energy level.

For measurement and evaluation, the absolute PL quantum yield was determined with an absolute PL Quantum yield measuring apparatus C9920-02 (manufactured by Hamamatsu Photonics K. K.). The emission lifetime was determined with a streak camera C4334 (manufactured by Hamamatsu Photonics K.K.) under excitation of the sample with a laser beam.

<<Constitution Layers of Organic EL Element>>

Representative element constitutions used for an organic EL element of the present invention are as follows, however, the present invention is not limited to these.

(1) Anode/light emitting layer/cathode
(2) Anode/light emitting layer/electron transport layer/cathode
(3) Anode/hole transport layer/light emitting layer/cathode
(4) Anode/hole transport layer/light emitting layer/electron transport layer/cathode (5) Anode/hole transport layer/light emitting layer/electron transport layer/electron injection layer/cathode
(6) Anode/hole injection layer/hole transport layer/light emitting layer/electron transport layer/cathode
(7) Anode/hole injection layer/hole transport layer/(electron blocking layer/) light emitting layer/(hole blocking layer/) electron transport layer/electron injection layer/cathode Among these, the embodiment (7) is preferably used. However, the present invention is not limited to this.

The light emitting layer of the present invention is composed of one or a plurality of layers. When a plurality of layers are employed, it may be placed a non-light emitting intermediate layer between the light emitting layers.

According to necessity, it may be provided with a hole blocking layer (it is also called as a hole barrier layer) or an electron injection layer (it is also called as a cathode buffer layer) between the light emitting layer and the cathode. Further, it may be provided with an electron blocking layer (it is also called as an electron barrier layer) or an hole injection layer (it is also called as an anode buffer layer) between the light emitting layer and the anode.

An electron transport layer according to the present invention is a layer having a function of transporting an electron. An electron transport layer includes an electron injection layer, and a hole blocking layer in a broad sense. Further, an electron transport layer unit may be composed of plural layers.

A hole transport layer according to the present invention is a layer having a function of transporting a hole. A hole transport layer includes a hole injection layer, and an electron blocking layer in a broad sense. Further, a hole transport layer unit may be composed of plural layers.

In the representative element constitutions as described above, the layers eliminating an anode and a cathode are also called as "organic layers".

(Tandem Structure)

An organic EL element of the present invention may be so-called a tandem structure element in which plural light emitting units each containing at least one light emitting are laminated.

A representative example of an element constitution having a tandem structure is as follows.

Anode/first light emitting unit/intermediate layer/second light emitting unit/intermediate layer/third light emitting unit/cathode.

Here, the above-described first light emitting unit, second light emitting unit, and third light emitting unit may be the same or different. It may be possible that two light emitting units are the same and the remaining one light emitting unit is different.

The plural light emitting units each may be laminated directly or they may be laminated through an intermediate layer. Examples of an intermediate layer are: an intermediate electrode, an intermediate conductive layer, a charge generating layer, an electron extraction layer, a connecting layer, and an intermediate insulating layer. Known composing materials may be used as long as it can form a layer which has a function of supplying an electron to an adjacent layer to the anode, and a hole to an adjacent layer to the cathode.

Examples of a material used in an intermediate layer are: conductive inorganic compounds such as ITO (indium tin oxide), IZO (indium zinc oxide), $ZnO_2$, TiN, ZrN, HfN, $TiO_X$, $VO_X$, CuI, InN, GaN, $CuAlO_2$, $CuGaO_2$, $SrCu_2O_2$, $LaB_6$, $RuO_2$, and Al; a two-layer film such as $Au/Bi_2O_3$; a multi-layer film such as $SnO_2/Ag/SnO_2$, $ZnO/Ag/ZnO$, $Bi_2O_3/Au/Bi_2O_3$, $TiO_2/TiN/TiO_2$, and $TiO_2/ZrN/TiO_2$; fullerene such as $C_{60}$; and a conductive organic layer such as oligothiophene, metal phthalocyanine, metal-free phthalocyanine, metal porphyrin, and metal-free porphyrin. The present invention is not limited to them.

Examples of a preferable constitution in the light emitting unit are the constitutions of the above-described (1) to (7) from which an anode and a cathode are removed. However, the present invention is not limited to them.

Examples of a tandem type organic EL element are described in: U.S. Pat. Nos. 6,337,492, 7,420,203, 7,473,923, 6,872,472, 6,107,734, 6,337,492, WO 2005/009087, JP-A 2006-228712, JP-A 2006-24791, JP-A 2006-49393, JP-A 2006-49394, JP-A 2006-49396, JP-A 2011-96679, JP-A 2005-340187, JP Patent 4711424, JP Patent 3496681, JP Patent 3884564, JP Patent 4213169, JP-A 2010-192719, JP-A 2009-076929, JP-A 2008-078414, JP-A 2007-059848, JP-A 2003-272860, JP-A 2003-045676, and WO 2005/094130. The constitutions of the elements and the composing materials are described in these documents, however, the present invention is not limited to them.

Each layer that constitutes an organic EL element of the present invention will be described in the following.

<<Light Emitting Layer>>

A light emitting layer according to the present invention is a layer which provide a place of emitting light via an exciton produce by recombination of electrons and holes injected from an electrode or an adjacent layer. The light emitting portion may be either within the light emitting layer or at an interface between the light emitting layer and an adjacent layer thereof. The constitution of the light emitting layer according to the present invention is not particularly limited as long as it satisfies the requirements of the present invention.

A total thickness of the light emitting layer is not particularly limited. However, in view of layer homogeneity, required voltage during light emission, and stability of the emitted light color against a drive electric current, the total layer thickness is preferably adjusted to be in the range of 2 nm to 5 µm, more preferably, it is in the range of 2 to 500 nm, and still most preferably, it is in the range of 5 to 200 nm.

Each light emitting layer is preferably adjusted to be in the range of 2 nm to 1 µm, more preferably, it is in the range of 2 to 200 nm, and still most preferably, it is in the range of 3 to 150 nm.

It is preferable that the light emitting layer of the present invention incorporates a light emitting dopant (a light emitting dopant compound, a dopant compound, or simply called as a dopant) and a host compound (a matrix material, a light emitting host compound, or simply called as a host). When at least one of the light emitting layers contains a π-conjugated compound and at least one of fluorescent compound and a phosphorescent compound, the emission efficiency is improved. It is preferable. Further, when at least one of the light emitting layers contains: a π-conjugated compound; at least one of fluorescent compound and a phosphorescent compound; and a host compound, the emission efficiency is improved. It is also preferable.

(1) Light Emitting Dopant

As a light emitting dopant, it is preferable to employ: a fluorescence emitting dopant (also referred to as a fluorescent dopant and a fluorescent compound) and a phosphorescence emitting dopant (also referred to as a phosphorescent dopant and a phosphorescent emitting material). In the present invention, it is preferable that at least one light emitting layer contains a fluorescence emitting dopant. In the present invention, it is preferable that at least one of the light emitting layers contains a fluorescent compound (described later) and a π-conjugated compound served as an assist-dopant.

In the present invention, it is preferable that the light emitting layer contains a light emitting compound in the range of 0.1 to 50 mass %, more preferably in the range of 1 to 30 mass %.

A concentration of a light emitting compound in a light emitting layer may be arbitrarily decided based on the specific compound employed and the required conditions of the device. A concentration of a light emitting compound may be uniform in a thickness direction of the light emitting layer, or it may have any concentration distribution.

It may be used plural light emitting compounds of the present invention. It may be used a combination of fluorescent compounds each having a different structure, or a combination of a fluorescence emitting compound and a phosphorescence emitting compound. Any required emission color will be obtained by this.

When the light emitting layer contains: a π-conjugated compound of the present invention having an absolute value of a difference between a lowest singlet excited level and a lowest triplet level ($\Delta E_{ST}$) is 0.5 eV or less; a light emitting compound; and a host compound, the π-conjugated compound of the present invention acts as an assist-dopant. Whereas, when the light emitting layer contains a π-conjugated compound of the present invention and a light emitting compound without containing a host compound, the π-conjugated compound of the present invention acts as a host compound.

The mechanism of appearing the effects is the same for both cases. The specific feature is that a triplet exciton produced on the π-conjugated compound of the present invention is converted to a singlet exciton via a reverse intersystem crossing (RISC).

By this, all energy of the excitons produced on the π-conjugated compound of the present invention is theoretically transferred to the light emitting compound. It may be achieved high emission efficiency.

Consequently, when the light emitting layer contains 3 components of a π-conjugated compound of the present invention, a light emitting compound, and a host compound, it is preferable that the energy levels of $S_1$ and $T_1$ of the π-conjugated compound are lower than the energy levels of $S_1$ and $T_1$ of the host compound, and higher than the energy levels of $S_1$ and $T_1$ of the light emitting compound.

In the same manner, when the light emitting layer contains 2 components of a π-conjugated compound of the present invention and a light emitting compound, it is preferable that the energy levels of $S_1$ and $T_1$ of the π-conjugated compound are higher than the energy levels of $S_1$ and $T_1$ of the light emitting compound.

Figure 7:
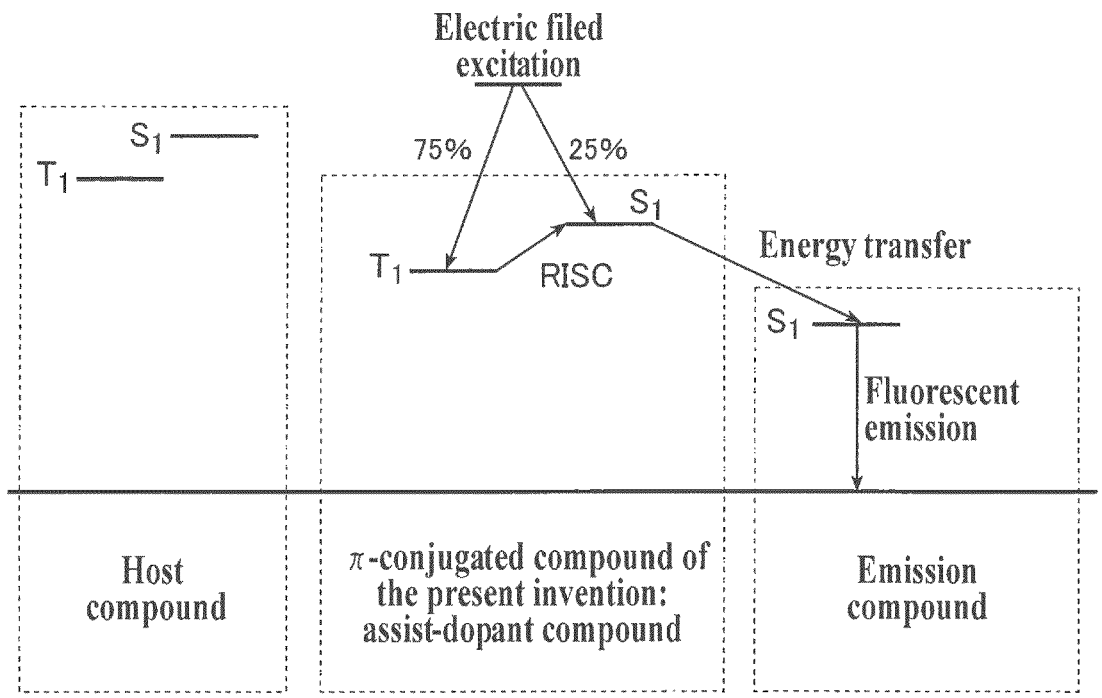
FIG. 7 is a schematic diagram illustrating the case in which a π-conjugated compound has a function of an assist-dopant.
Figure 8:
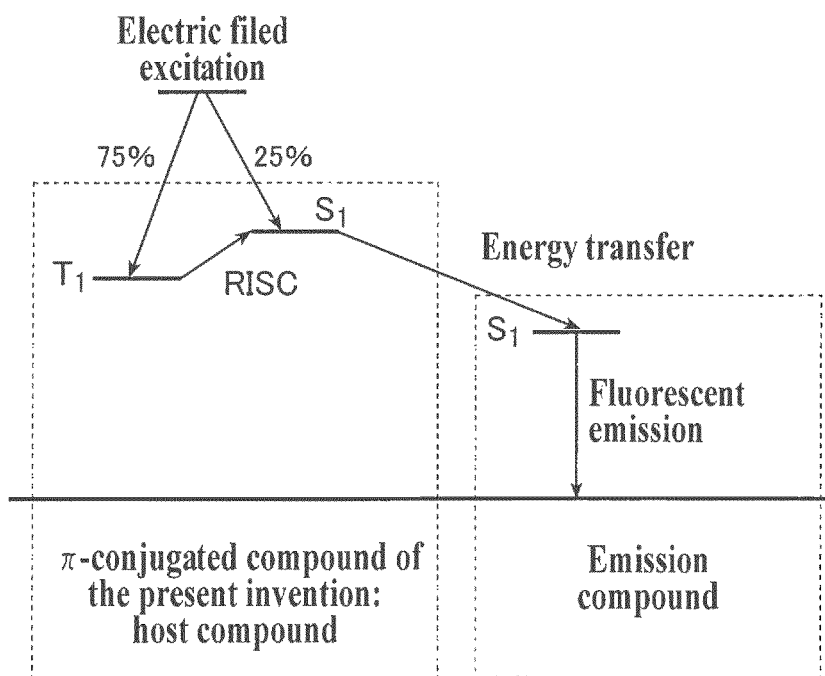
FIG. 8 is a schematic diagram illustrating the case in which a π-conjugated compound has a function of a host compound.

FIG. 7 and FIG. 8 illustrate a schematic diagram of the case in which the π-conjugated compound of the present invention acts as an assist-dopant or a host compound. FIG. 7 and FIG. 8 are only an example, the production process of the triplet exciton on the π-conjugated compound of the present invention is not limited to the electric field excitation, the production process includes the cases of an energy transfer or an electron transfer in the light emitting layer or from the surrounding interface.

Further, FIG. 7 and FIG. 8 illustrate the diagram using a fluorescence emitting compound as a light emitting compound, however, the present invention is not limited to it, and it may be used a phosphorescence emitting compound, and it may be used both of a fluorescence emitting compound and a phosphorescence emitting compound.

When a π-conjugated compound of the present invention is used as an assist-dopant, it is preferable that the light emitting layer contains a host compound in an amount of 100 mass % or more with respect to the π-conjugated compound, and that it contains a fluorescence emitting compound and/or a phosphorescence emitting compound in an amount of 0.1 to 50 mass % with respect to the π-conjugated compound.

When a π-conjugated compound of the present invention is used as a host compound, it is preferable that the light emitting layer contains a fluorescence emitting compound and/or a phosphorescence emitting compound in an amount of 0.1 to 50 mass % with respect to the π-conjugated compound.

When a π-conjugated compound of the present invention is used as an assist-dopant or a host compound, it is preferable that an emission spectrum of the π-conjugated compound of the present invention and an absorption spectrum of the light emitting compound are overlapped from the viewpoint of achieving high light emission efficiency.

Figure 3:
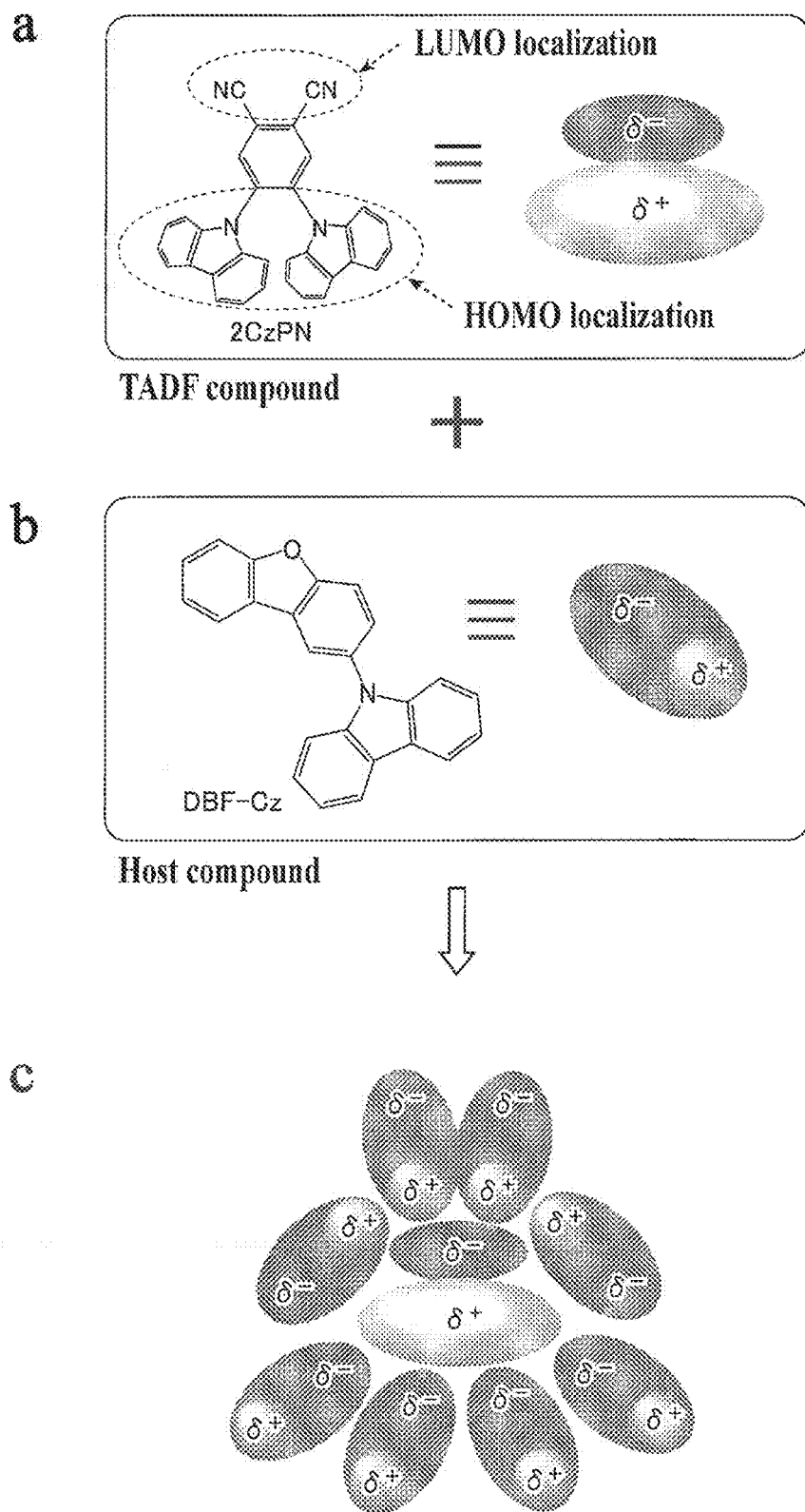
FIG. 3 is a schematic interaction diagram of a TADF compound and a host compound.
Figure 4:
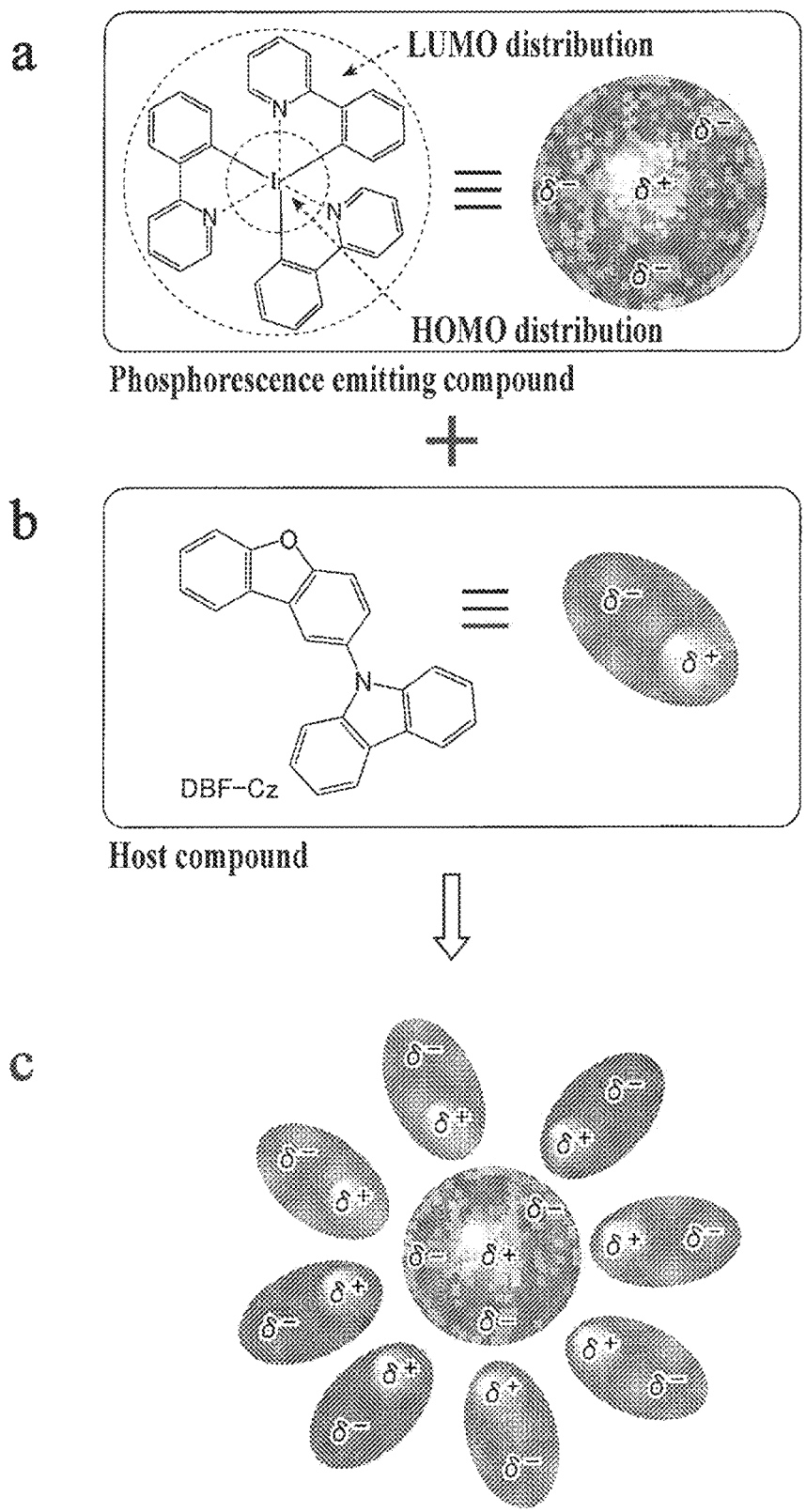
FIG. 4 is a schematic diagram illustrating an interaction of a phosphorescent compound and a host compound.
Figure 5:
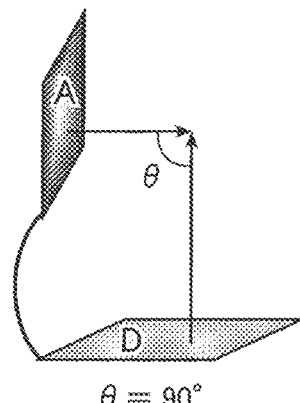
FIG. 5 is a schematic diagram illustrating an angle θ of the present invention.
Figure 5:
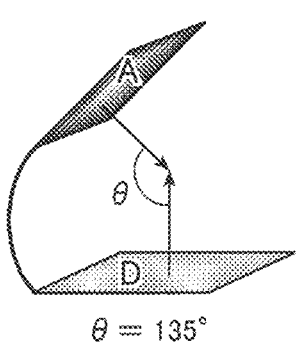
Figure 5:
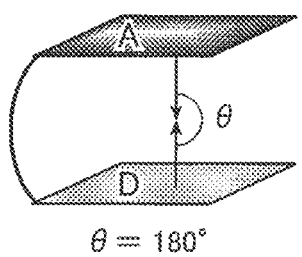
Figure 5:
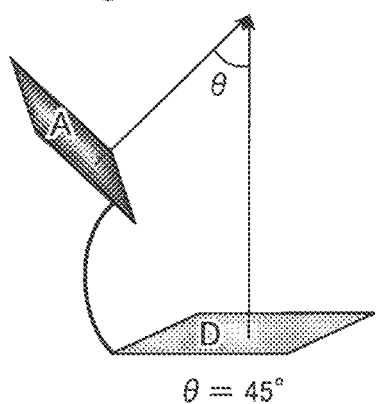
Figure 5:
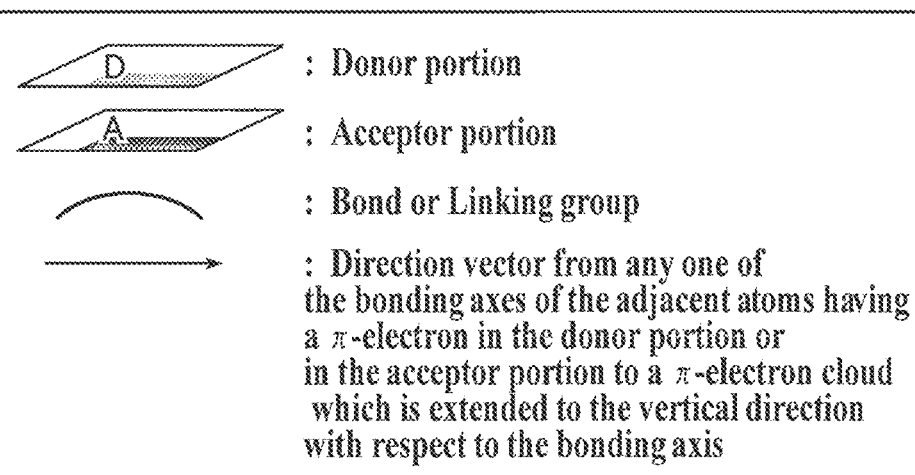

Color of light emitted by an organic EL element or a compound of the present invention is specified as follows. In FIG. 3.16 on page 108 of "Shinpen Shikisai Kagaku Handbook (New Edition Color Science Handbook)" (edited by The Color Science Association of Japan, Tokyo Daigaku Shuppan Kai, 1985), values determined via Spectroradiometer CS-1000 (produced by Konica Minolta, Inc.) are applied to the CIE chromaticity coordinate, whereby the color is specified.

In the present invention, it is preferable that the organic EL element of the present invention exhibits white emission by incorporating one or plural light emitting layers containing plural emission dopants having different emission colors.

The combination of emission dopants producing white is not specifically limited. It may be cited, for example, combinations of: blue and orange; and blue, green and red.

It is preferable that "white" in the organic EL element of the present invention shows chromaticity in the CIE 1931 Color Specification System at 1,000 cd/m$^2$ in the region of x=0.39±0.09 and y=0.38±0.08, when measurement is done to 2-degree viewing angle front luminance via the aforesaid method.

(1.1) π-Conjugated Compound

The π-conjugated compound of the present invention has a direction vector from an atom having a HOMO orbital in the electron donor portion to an electron cloud of the HOMO orbital, and a direction vector from an atom having a LUMO orbital in the electron acceptor portion to an electron cloud of the LUMO orbital, and the two direction vectors form an angle θ in the range of 90 to 180 degrees, and the π-conjugated compound has at least one of a plurality of the electron donor portions and a plurality of the electron acceptor portions. It is more preferable that the angle θ is in the range of 135 to 180 degrees.

This π-conjugated compound may be suitably used for a light-emitting thin film of the present invention described later.

A donor portion is a porting having an electron donating property. In the present invention, a HOMO designates a π-orbital or an n-orbital localized in a donor portion. Here, "portion" in the donor portion indicates a substituent or an atomic group.

Examples of a donor portion are: arylamine derivatives, carbazole, phenoxazine, 9,10-dihydroacridine, and phenothiazine.

An acceptor portion is an electron withdrawing portion that is electron deficient. In the present invention, a LUMO designates a π*-orbital or a σ*-orbital localized in an acceptor portion. Here, "portion" in the acceptor portion indicates a substituent or an atomic group.

Examples of an acceptor portion are: a benzene ring substituted with a cyano group, a triazine ring, a pyrimidine ring, a boron atom, and a sulfonyl group.

It will be described a direction vector from an atom having a HOMO orbital in the electron donor portion to an electron cloud of the HOMO orbital, and a direction vector from an atom having a LUMO orbital in the electron acceptor portion to an electron cloud of the LUMO orbital. The electron cloud of the HOMO orbital in the electron donor portion indicates an electron cloud of a π-orbital or an n-orbital in the donor portion. The electron cloud of the LUMO orbital in the electron acceptor portion indicates an electron cloud of a π*-orbital or a σ*-orbital in the acceptor portion. The directions of π-orbital, n-orbital, π*-orbital and σ*-orbital extended from the atom are known by the molecular orbital method. For example, the π-orbital composed of sp2 hybrid orbitals has a direction of a 2 pz orbital as a direction vector of the present invention.

The angle θ according to the present invention is an angle formed with a direction vector from an atom having a HOMO orbital in the electron donor portion to an electron cloud of the HOMO orbital, and a direction vector from an atom having a LUMO orbital in the electron acceptor portion to an electron cloud of the LUMO orbital.

The angle θ according to the present invention may be calculated using a molecular orbital calculation software of Gaussian 09 made by The US Gaussian Inc., (Revision C.01, by M. J. Frisch et al., Gaussian Inc., 2010) with B3LYP as a functional and 6-31G(d) as a base function for a calculation method. The calculation software and the calculation method are not limited, it may be obtained the same results by using any method.

The π-conjugated compound of the present invention has an electron donor portion and an electron acceptor portion in the molecule. It is preferable that the π-conjugated compound has one electron acceptor portion that is bonded to two or more electron donor portions through a linking group, or it has one electron donor portion that is bonded to two or more electron acceptor portions through a linking group.

Further, it is also preferable that the π-conjugated compound of the present invention has one electron acceptor portion that is directly bonded to two or more electron donor portions, or it has one electron donor portion that is directly bonded to two or more electron acceptor portions.

Specific examples of a preferable π-conjugated compound of the present invention are a π-conjugated compound represented by any one of Formulas (1) to (8). At least one of the light emitting layers according to the present invention preferably contains at least one of these π-conjugated compounds.

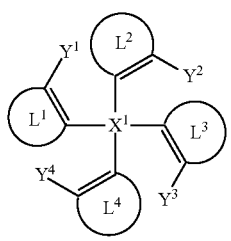

Formula (1)

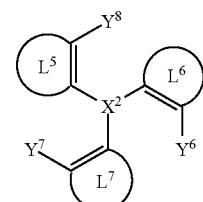

Formula (2)

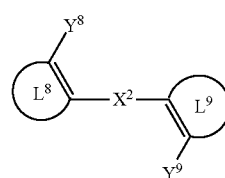

Formula (3)

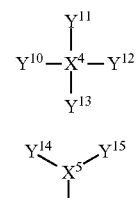

Formula (4)

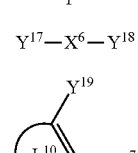

Formula (5)

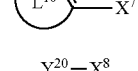

Formula (6)

Formula (7)

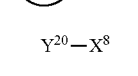

Formula (8)

In Formulas, $X^1$ to $X^8$ and $Y^1$ to $Y^{20}$ each respectively represent the electron donor portion or the electron acceptor portion; when $X^1$ to $X^8$ each respectively represent the electron donor portion, $Y^1$ to $Y^{20}$ each respectively represent the electron acceptor portion; when to $X^8$ each respectively represent the electron acceptor portion, $Y^1$ to $Y^{20}$ each respectively represent the electron donor portion; $L^1$ to $L^{10}$ represent a linking group, $L^1$ to $L^{10}$ each respectively represent an aryl group which may have a substituent or a heteroaryl group which may have a substituent, $L^1$ binds $X^1$ and $Y^1$ through adjacent carbon atoms, $L^2$ binds $X^1$ and $Y^2$ through adjacent carbon atoms, $L^3$ binds $X^1$ and $Y^3$ through adjacent carbon atoms, $L^4$ binds $X^1$ and $Y^4$ through adjacent carbon atoms, $L^5$ binds $X^2$ and $Y^5$ through adjacent carbon atoms, $L^6$ binds $X^2$ and $Y^6$ through adjacent carbon atoms, $L^7$ binds $X^2$ and $Y^7$ through adjacent carbon atoms, $L^8$ binds $X^3$ and $Y^8$ through adjacent carbon atoms, $L^9$ binds $X^3$ and $Y^9$ through adjacent carbon atoms, and $L^{10}$ binds $X^7$ and $Y1^9$ through adjacent carbon atoms.

Further, it is preferable that the electron donor portion and the electron acceptor portion represented by $X^1$ to $X^8$ and $Y^1$ to $Y^{20}$ in Formulas (1) to (8) each respectively are one selected from the group consisting of an aryl group which may have a substituent, a heteroaryl group which may have a substituent, an alkyl group which may have a substituent, a carbonyl group which may have a substituent, a nitrogen atom which may have a substituent, a sulfur atom which may have a substituent, a boron atom which may have a substituent, a phosphor atom which may have a substituent, an oxygen atom which may have a substituent, and a silicon atom which may have a substituent.

Further, it is preferable that the electron acceptor portions represented by $X^1$ to $X^8$ and $Y^1$ to $Y^{20}$ in Formulas (1) to (8) each respectively are one selected from the group consisting of: an aryl ring having 6 to 20 carbon atoms which may by partially substituted with an alkyl group, an aryl ring having 6 to 20 carbon atoms which may by partially substituted with an alkoxy group, a carbazole ring which may have a substituent, an indoloindole ring which may have a substituent, a 9,10-dihydroacrydine ring which may have a substituent, a phenoxazine ring which may have a substituent, a phenothiazine ring which may have a substituent, a 5,10-dihydrophenazine ring which may have a substituent, a dibenzothiophene ring which may have a substituent, an amino group which may have a substituent, and a thio group which may have a substituent.

Further, it is preferable that the electron acceptor portions represented by $X^1$ to $X^8$ and $Y^1$ to $Y^{20}$ in Formulas (1) to (8) each respectively are one selected from the group consisting of: an aryl ring having 6 to 20 carbon atoms which may be partially substituted with a cyano group, an aryl ring having 6 to 20 carbon atoms which may be partially substituted with a fluoroalkyl group, an aryl ring having 6 to 20 carbon atoms which may be partially or wholly substituted with a fluorine atom, a nitrogen atom-containing aromatic ring having 5 to 13 carbon atoms which may have a substituent, a dibenzoborol ring which may have a substituent, a dibenzothiophene oxide ring which may have a substituent, a dibenzothiophene dioxide ring which may have a substituent, a sulfinyl group which may have a substituent, a sulfonyl group which may have a substituent, a boryl group which may have a substituent, a phosphine oxide group which may have a substituent, a silyl group which may have a substituent, a pyridine ring, a pyrdazine ring, a pyrimidine ring, a pyrazine ring, a triazine ring, a quinoline ring, an isoquinoline ring, a quinazoline ring, a cinnoline ring, a quinoxaline ring, a phthalazine ring, a pteridine ring, an acridine ring, a phenanthridine ring, and a phenanthroline ring. It is particularly preferable that they are one selected from the group consisting of: a pyridine ring, a pyridazine ring, a pyrimidine ring, a pyrazine ring, a triazine ring, a quinoline ring, an isoquinoline ring, a phenanthridine ring, and a phenanthroline ring.

Specific examples of the aryl group having 6 to 20 carbon atoms are: a benzene ring, an indene ring, a naphthalene ring, an azulene ring, a fluorene ring, a phenanthrene ring, an anthracene ring, an acenaphthylene ring, a biphenylene ring, a chrysene ring, a naphthacene ring, a pyrene ring, a pentalene ring, an aceanthrylene ring, a heptalene ring, a triphenylene ring, an as-indacene ring, a chrysene ring, an s-indacene ring, a pleiadene ring, a phenalene ring, a fluoranthene ring, a perylene ring, and an acephenanthrylene ring. More preferable examples are: a benzene ring, a naphthalene ring, a fluorene ring, a phenanthrene ring, an anthracene ring, a biphenylene ring, a chrysene ring, a pyrene ring, a triphenylene ring, a chrysene ring, a fluoranthene ring, and a perylene ring. Particularly preferable examples are: a benzene ring, a naphthalene ring, a phenanthrene ring, and a pyrene ring.

The above-describe alkyl group may be straight, branched or cyclic. Examples thereof are: a straight, branched or cyclic alkyl group having 1 to 20 carbon atoms. Specific examples are: a methyl group, an ethyl group, an n-propyl group, an isopropyl group, an n-butyl group, an s-butyl group, a t-butyl group, an n-pentyl group, a neopentyl group, an n-hexyl group, a cyclohexyl group, a 2-ethylhexyl group, an n-heptyl group, an n-octyl group, a 2-hexyloctyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, and an n-icosyl group. More preferable examples are: a methyl group, an ethyl group, an isopropyl group, a t-butyl group, a cyclohexyl group, a 2-ethylhexyl group, and 2-hexyloctyl group.

The above-describe alkoxy group may be straight, branched or cyclic. Examples thereof are: a straight, branched or cyclic alkoxy group having 1 to 20 carbon atoms. Specific examples are: a methoxy group, an ethoxy group, an n-propoxy group, an isopropoxy group, an n-butoxy group, an isobutoxy group, a t-butoxy group, an n-pentyloxy group, a neopentyloxy group, an n-hexyloxy group, a cyclohexyloxy group, an n-heptyloxy group, an n-octyloxy group, a 2-ethylhexyloxy group, a nonyloxy group, a decyloxy group, a 3, 7-dimethyloctyloxy group, an n-undecyloxy group, an n-dodecyloxy group, an n-tridecyloxy group, an n-tetradecyloxy group, a 2-n-hexyl-n-octyloxy group, an n-pentadecyloxy group, an n-hexadecyloxy group, an n-heptadecyloxy group, an n-octadecyloxy group, an n-nonadecyloxy group, and an n-icosyloxy group. More preferable examples are: a methoxy group, an ethoxy group, an isopropoxy group, a t-butoxy group, a cyclohexyloxy group, a 2-ethylhexyloxy group, and a 2-hexyloctyloxy group.

The above-describe linking group (including $L^1$ to $L^{10}$ in Formulas (1) to (3) and (7)) is not limited in particular as long as it does not hinder the effect of the present invention. Preferable examples thereof are: a benzene ring, a naphthalene ring, a thiophene ring, a furan ring, a benzofuran ring, a benzothiophene ring, and a thienothiophene ring. It is particularly preferable that $L^1$ to $L^{10}$ in Formulas (1) to (3) and (7) each are a benzene ring.

As a π-conjugated compound represented by any one of Formulas (1) to (8), it may be cited the following compounds. However, the present invention is not limited to them.

In addition, the following compounds all have the above-described angle θ in the range of 90 to 180 degrees.

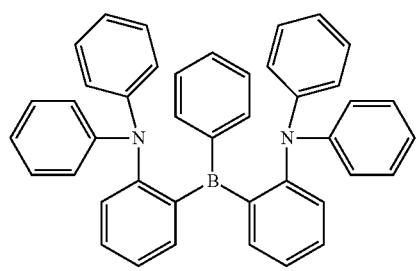

T-1

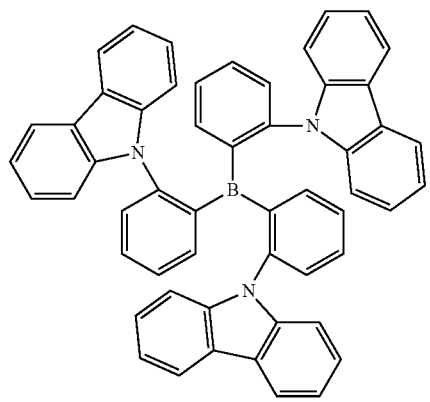

T-2

-continued
T-3
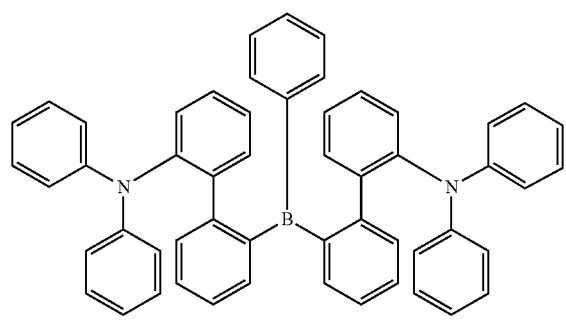
T-4
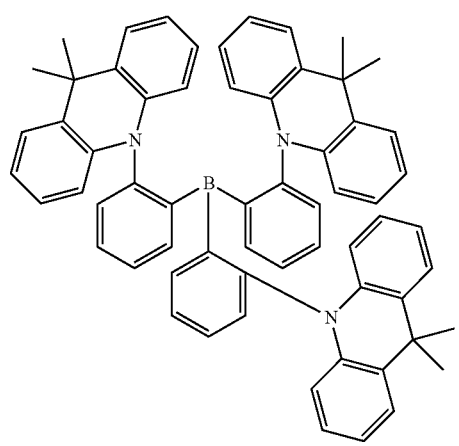
T-5
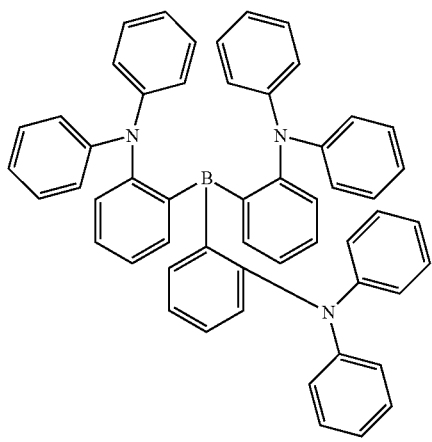
T-6
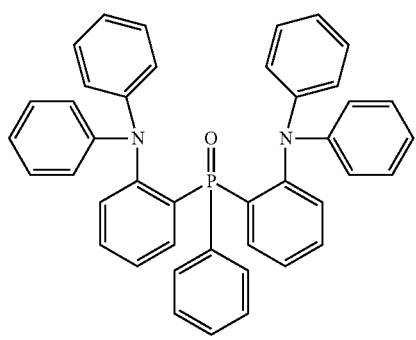
T-7
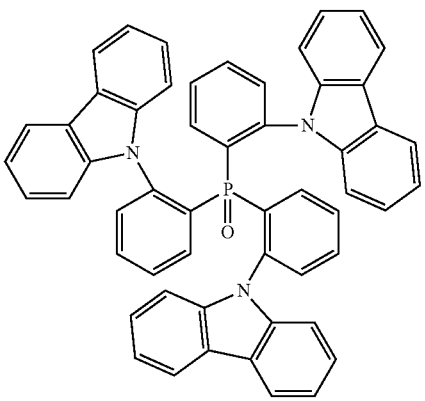
T-8
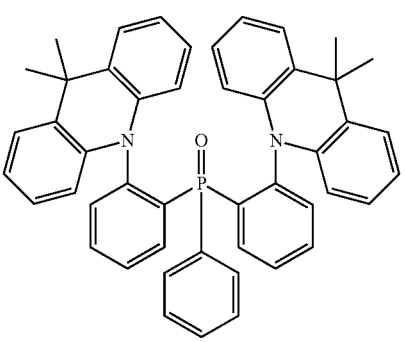
T-9
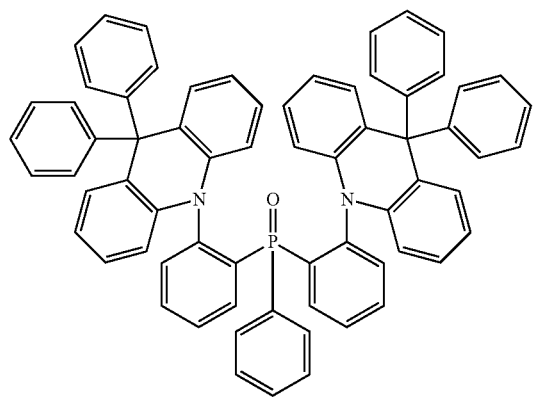
T-10
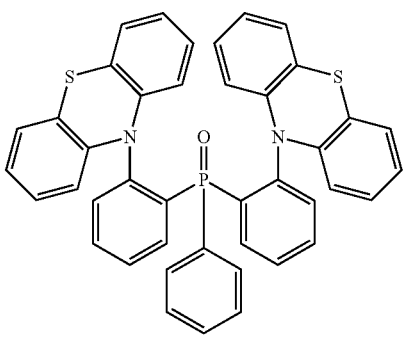

T-11
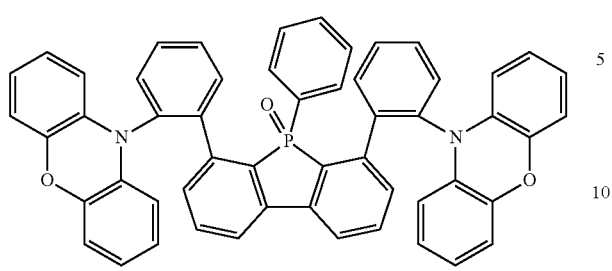
T-12
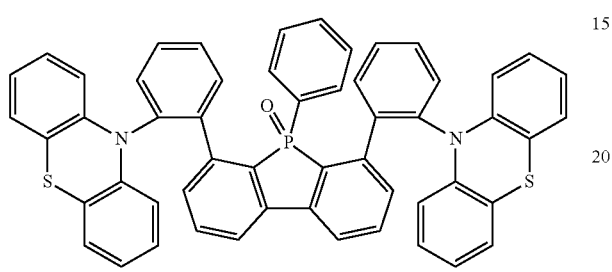
T-13
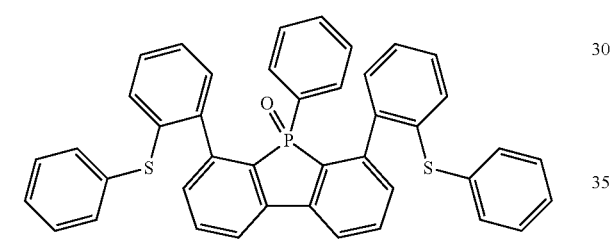
T-14
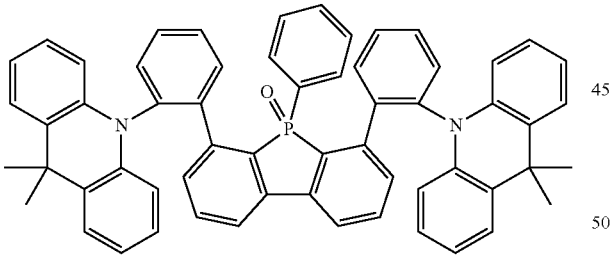
T-15
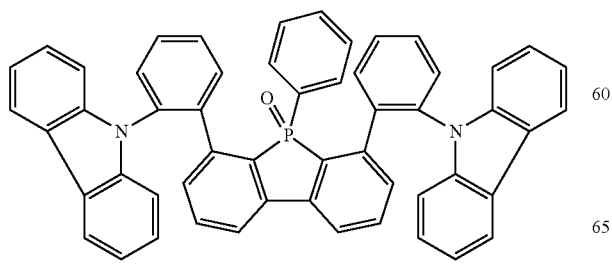
T-16
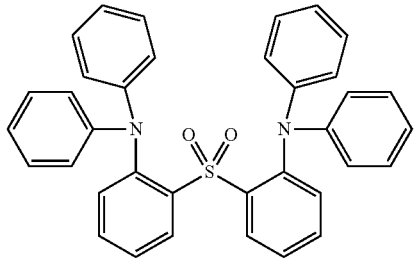
T-17
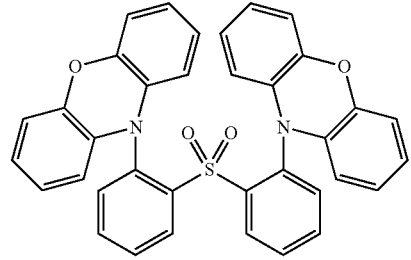
T-18
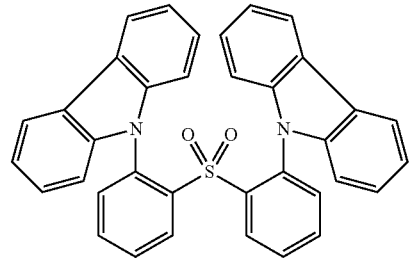
T-19
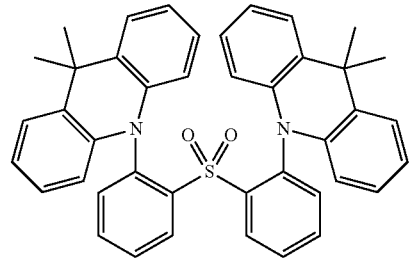
T-20
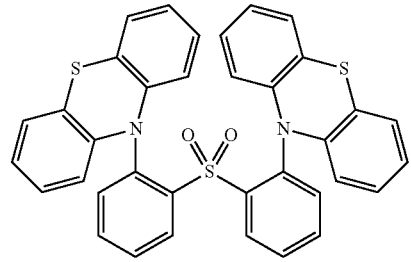
T-21
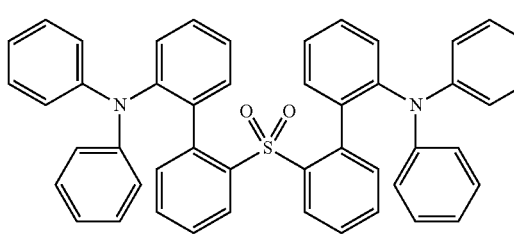

-continued
T-22
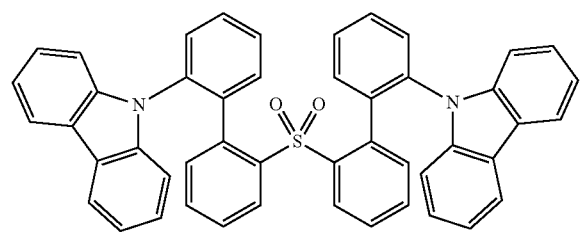
T-23
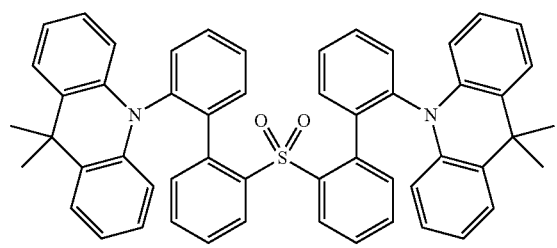
T-24
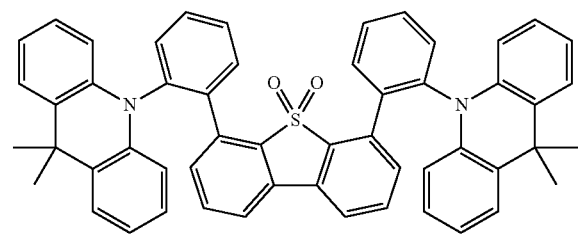
T-25
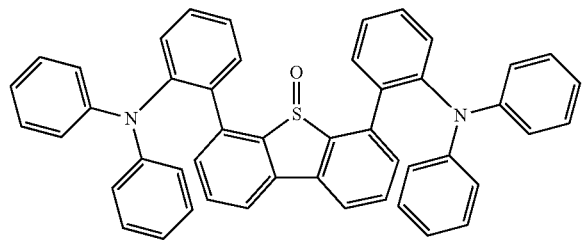
T-26
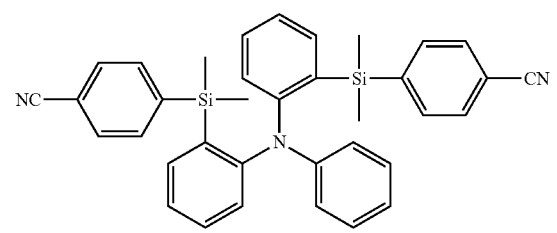
T-27
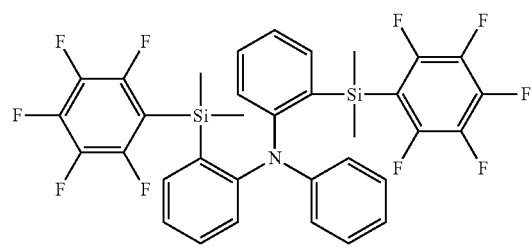
-continued
T-28
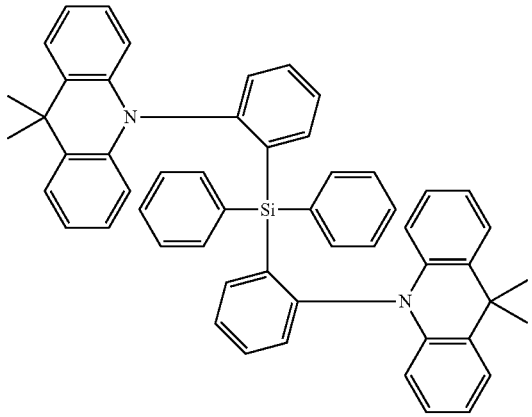
T-29
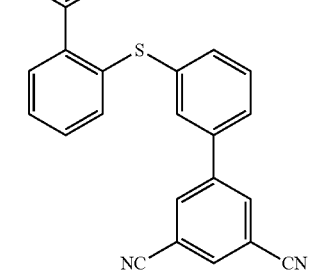
T-30
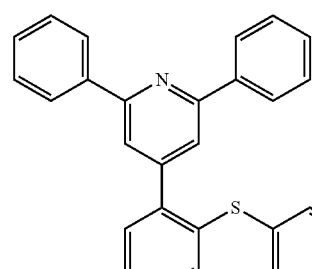
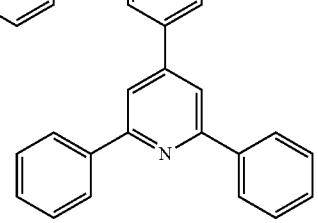
T-31
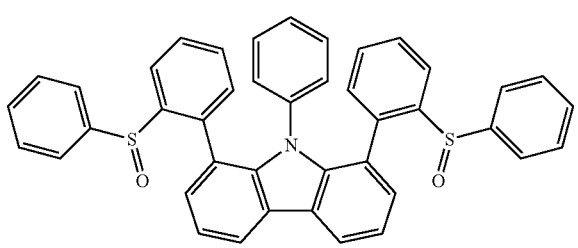

T-32 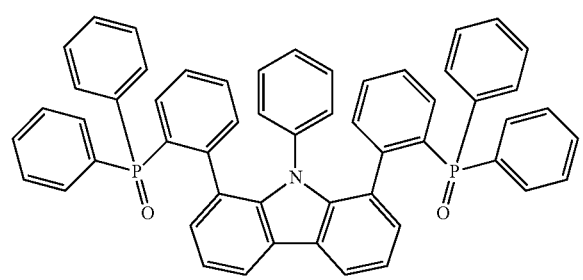
T-33 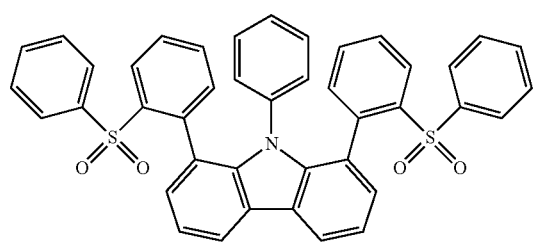
T-34 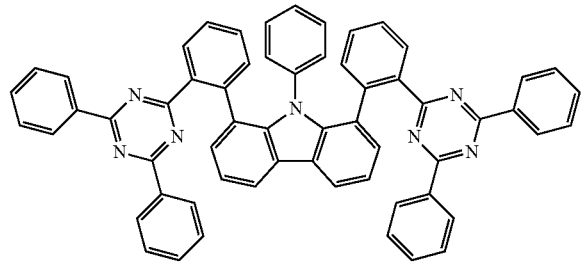
T-35 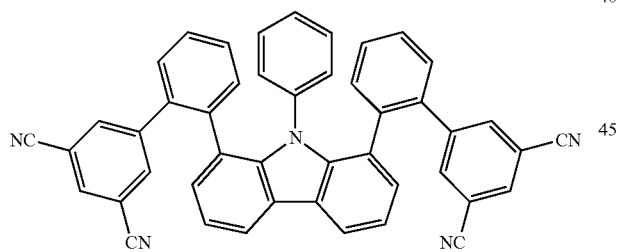
T-36 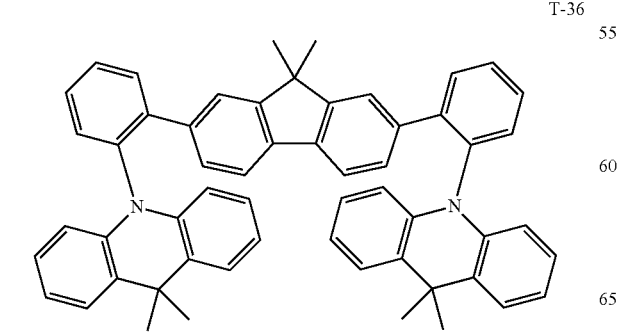
T-37 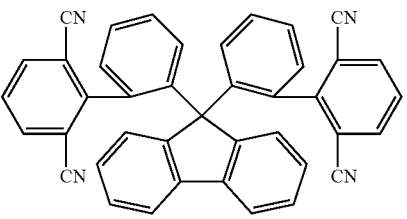
T-38 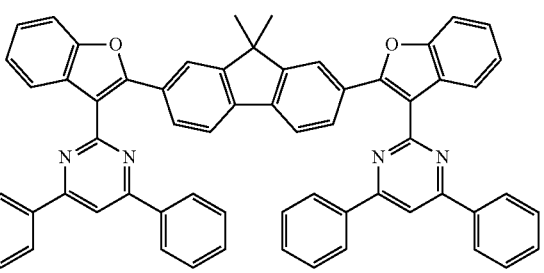
T-39 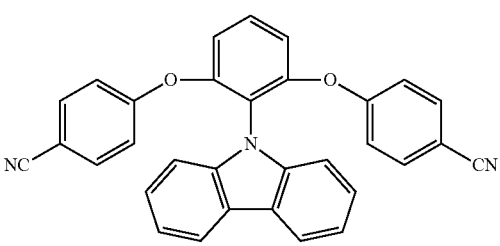
T-40 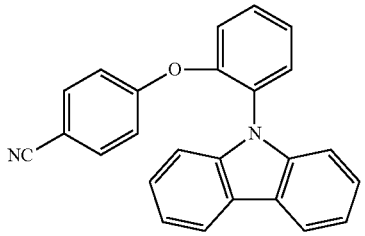
T-41 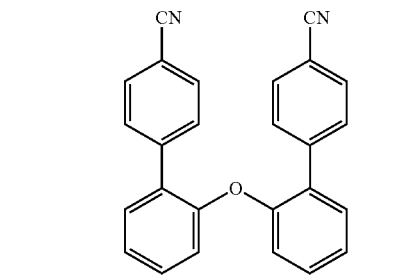
T-42 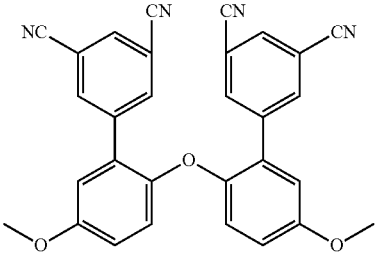

T-43
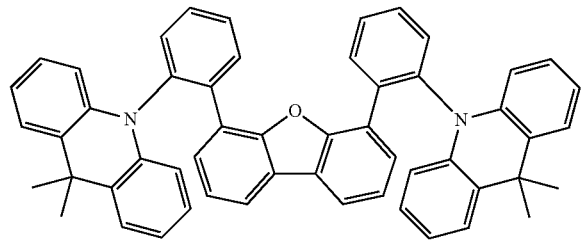
T-44
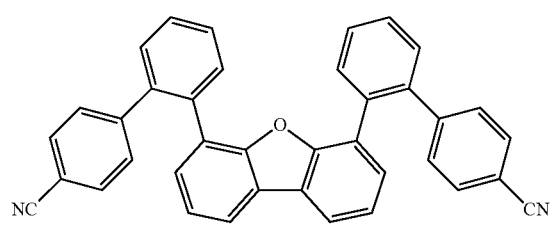
T-45
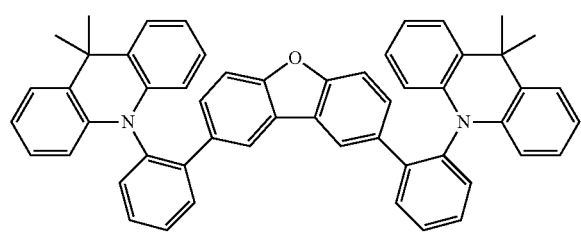
T-46
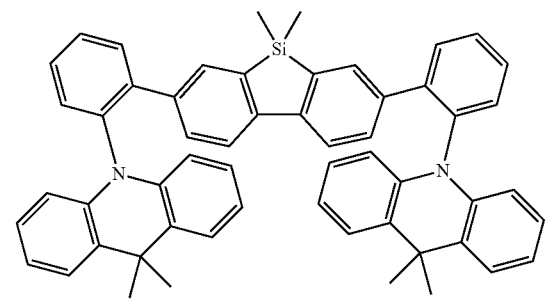
T-47
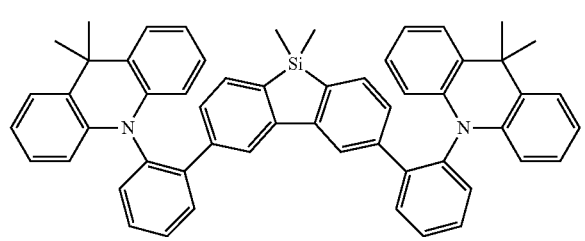
T-48
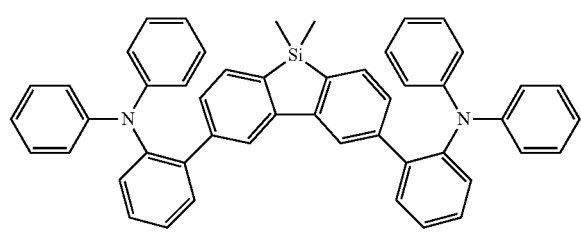
T-49
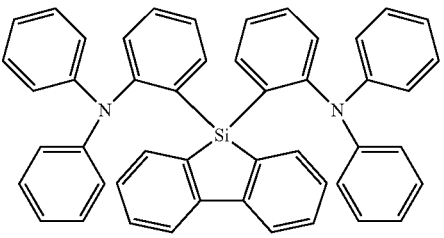
T-50
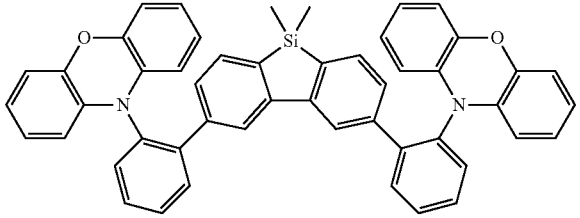
T-51
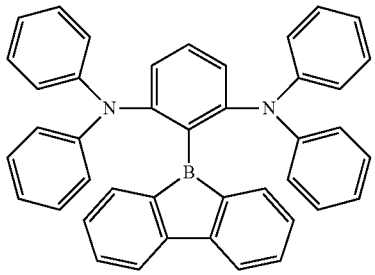
T-52
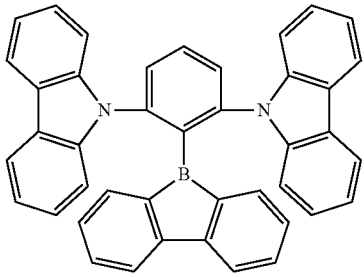
T-53
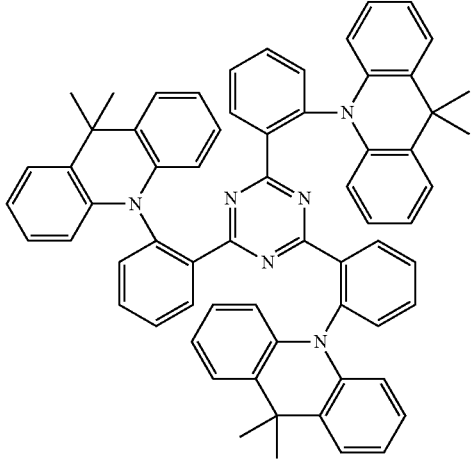

T-54
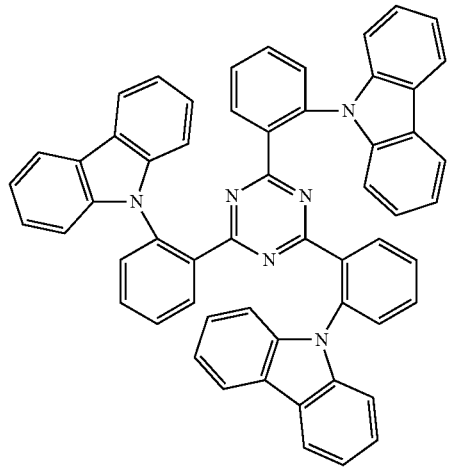
T-55
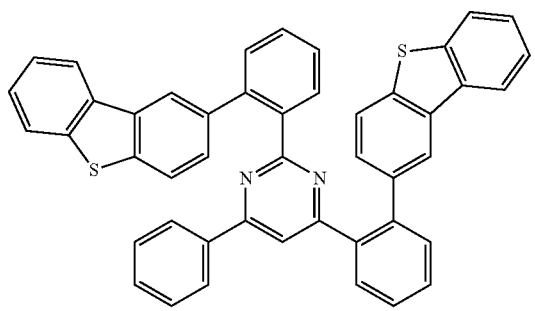
T-56
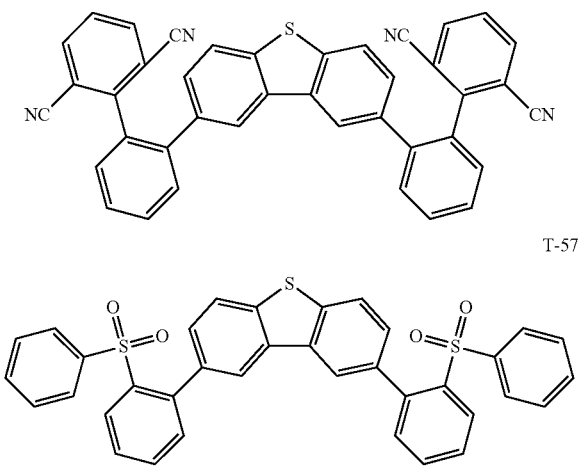
T-57
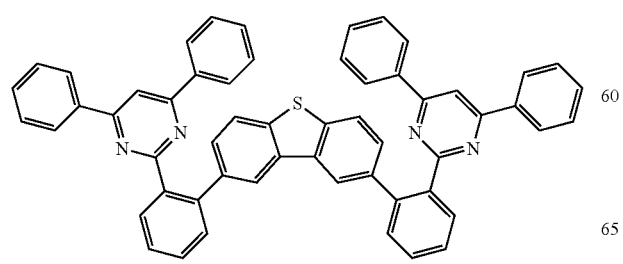
T-58
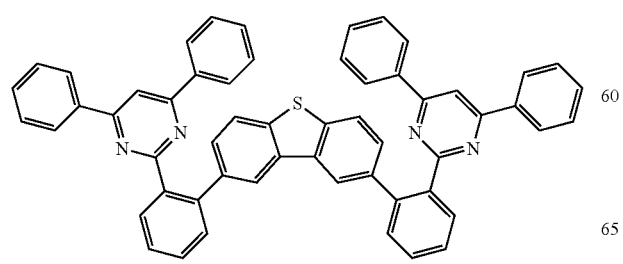
T-59
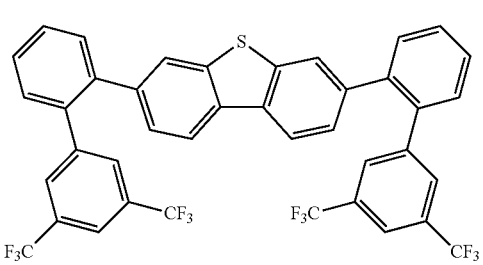
T-60
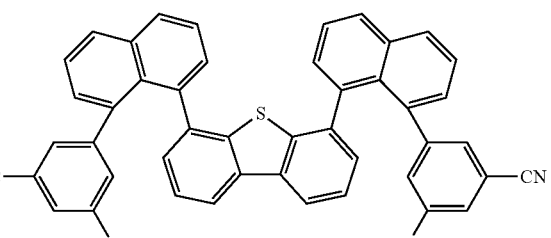
T-61
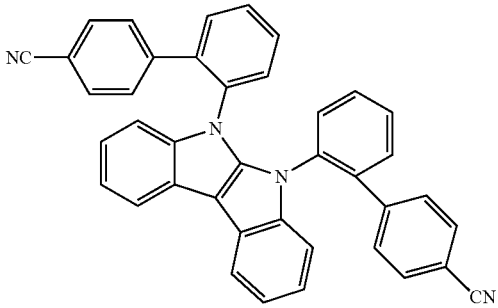
T-62
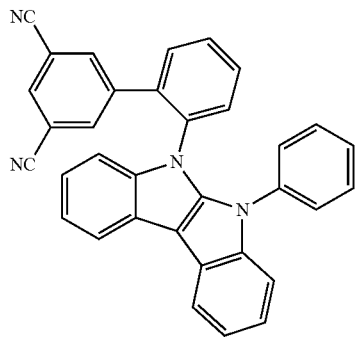
T-63
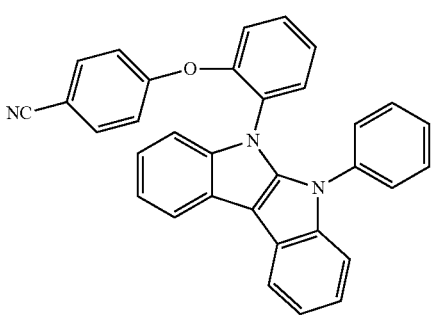

-continued
T-64
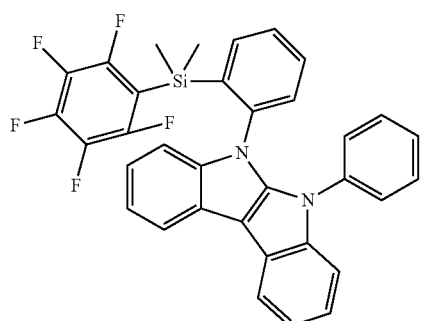
T-65
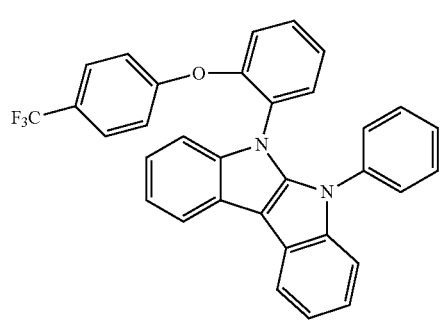
T-66
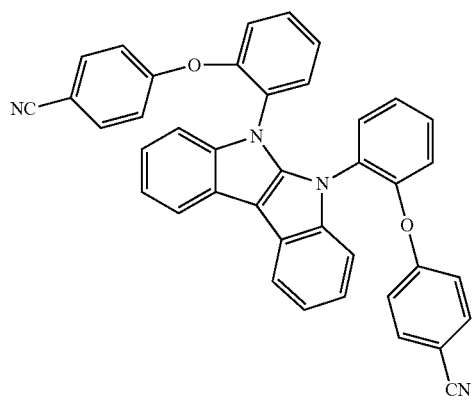
T-67
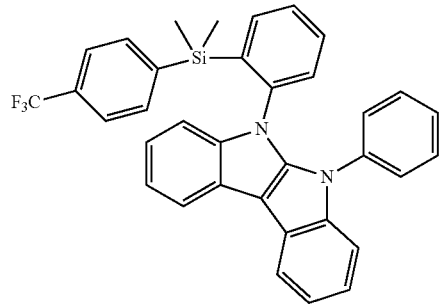
-continued
T-68
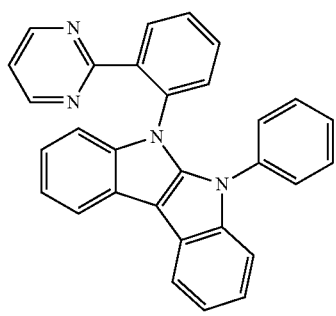
T-69
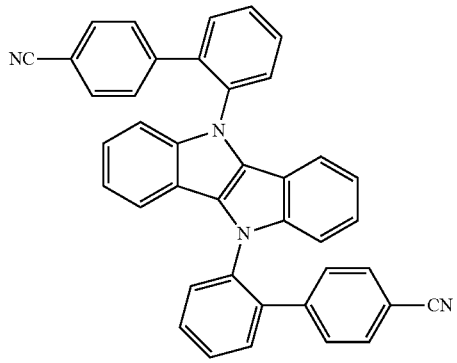
T-70
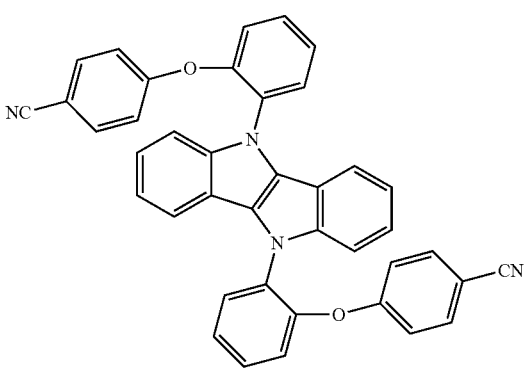
T-71
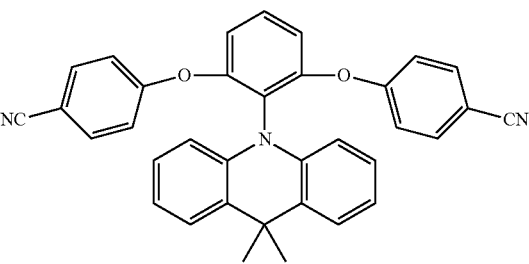

T-72
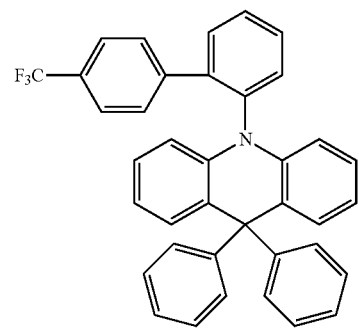
T-73
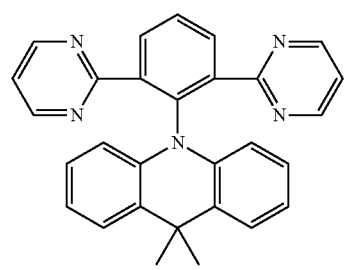
T-74
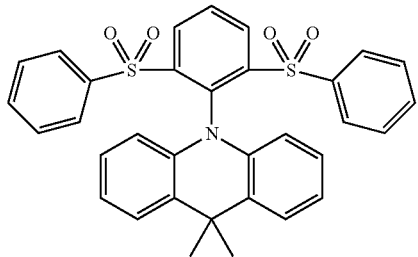
T-75
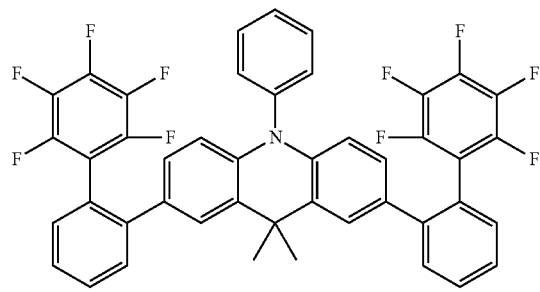
T-76
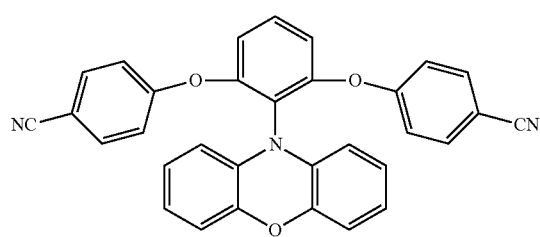
T-77
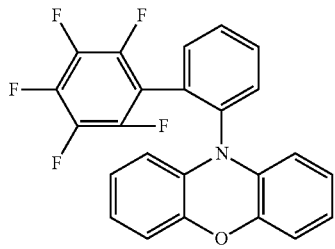
T-78
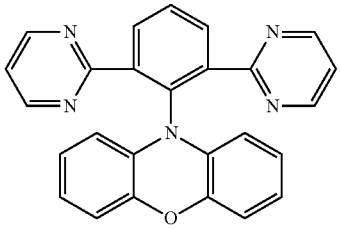
T-79
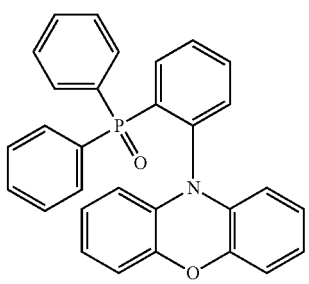
T-80
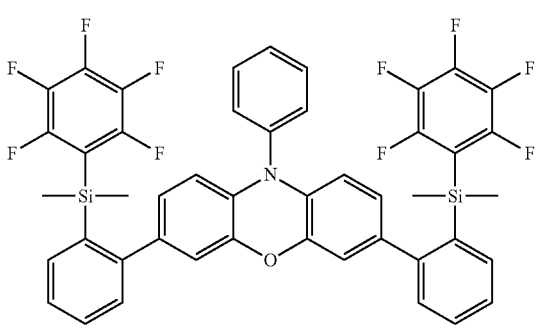
T-81
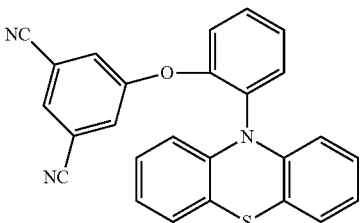
T-82
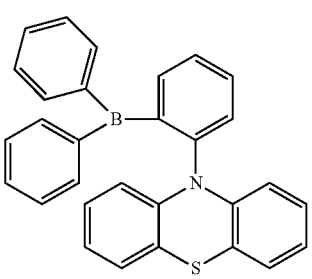

T-83 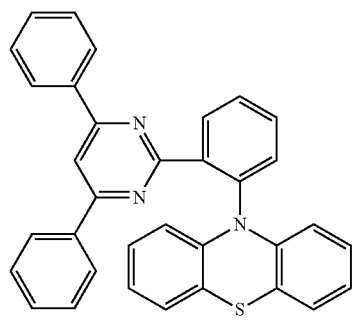
T-84 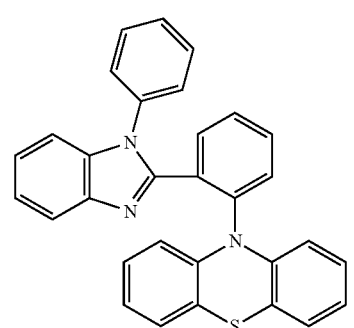
T-85 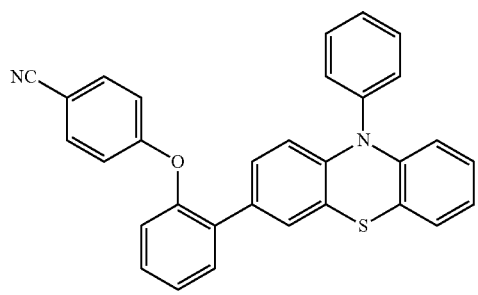
T-86 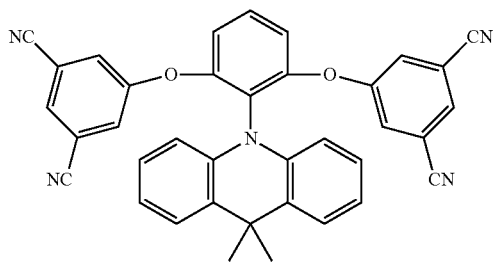
T-87 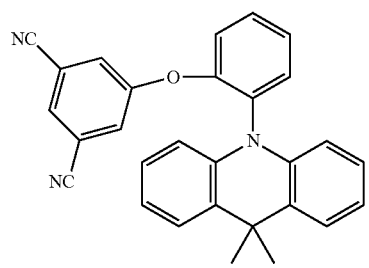
T-88 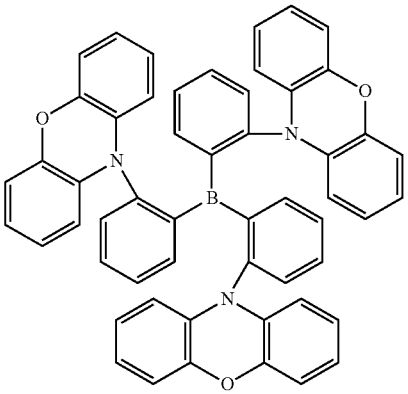
T-89 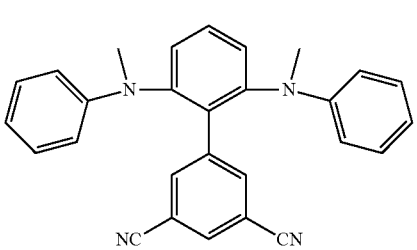
T-90 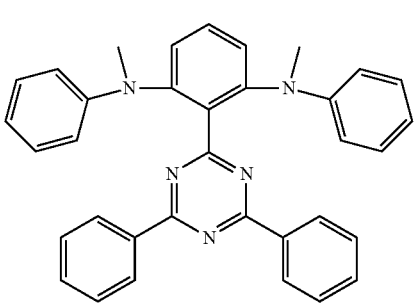
T-91 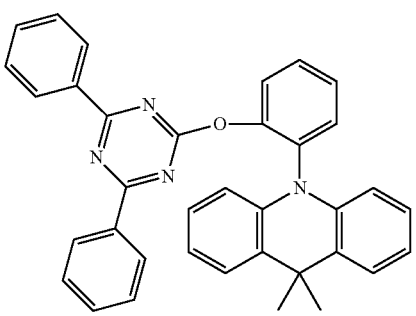
T-92 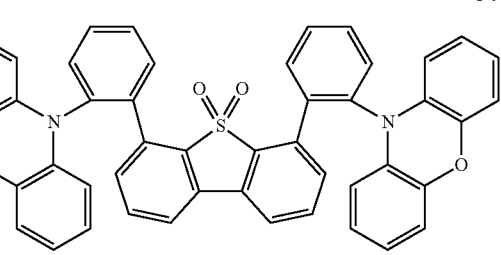

T-93
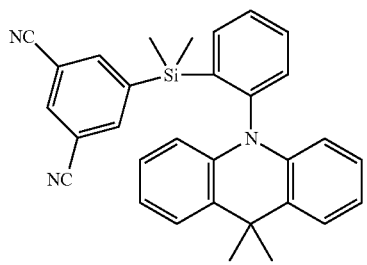
T-94
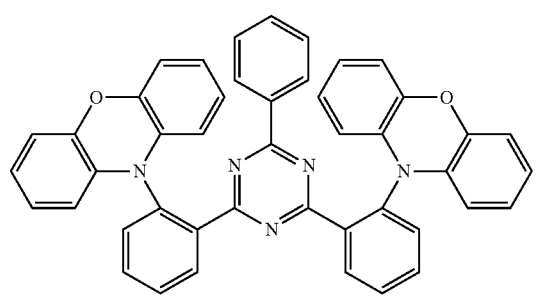
T-95
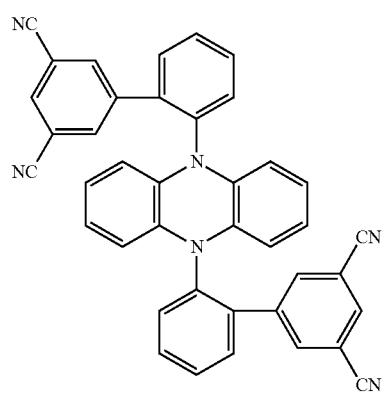
T-96
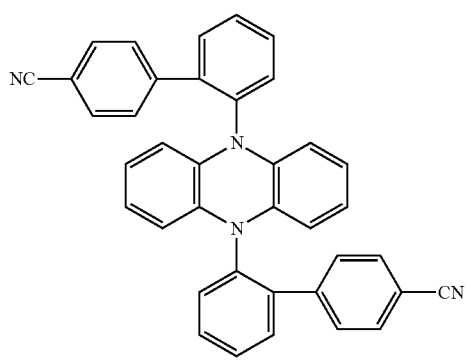
T-97
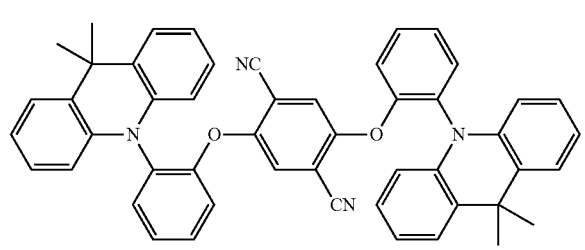
T-98
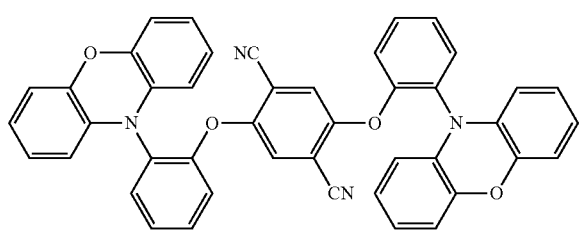
T-99
T-100
T-101
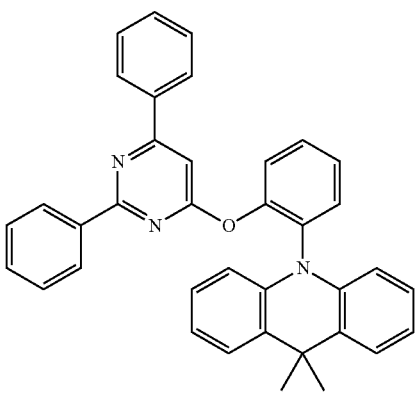
T-102
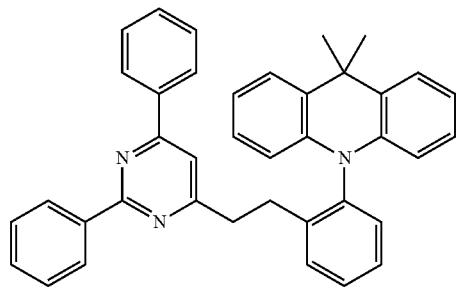

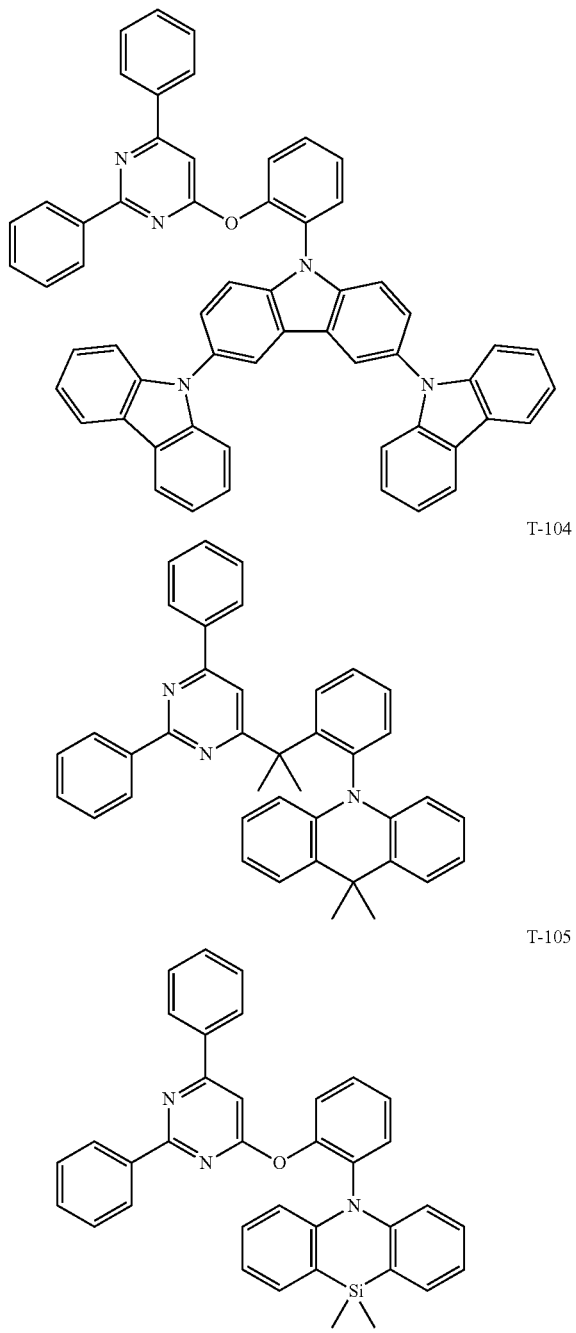

T-103

T-104

T-105

By using these compounds, it is possible to achieve a structure in which an electron transition will be easily taken place from a donor portion to an acceptor portion. In addition, among these compounds, the materials having $\Delta E_{ST}$ (an absolute value) in the range of 0.5 eV or less may exhibit a TADF property. Further, since these compounds have a bipolar property and they may be compatible with a variety of energy levels, they may be used as an emission host, and they may be suitably used as a hole transport compound or an electron transport compound. Consequently, the use of these compounds is not limited to a light emission layer, they may be used in the hole injection layer, a hole transport layer, an electron blocking layer, a hole blocking layer, an electron transport layer, an electron injection layer, or an intermediate layer.

<Synthetic Method>

The above-described π-conjugated compound may be synthesized with the methods described in Non-patent document 2: Journal of Organometallic Chemistry, 2003, 680, 218-222 and WO 2011/8560 or by referring to the methods described in the references of these documents.

(1.2) Fluorescence Emitting Dopant

As a fluorescent dopant, it may be used a π-conjugated compound of the preset invention. Otherwise, it may be suitably selected from the known fluorescent dopants and delayed fluorescent dopants used in a light emitting layer of an organic EL element.

As specific known fluorescence emitting dopants usable in the present invention, listed are compounds such as: an anthracene derivative, a pyrene derivative, a chrysene derivative, a fluoranthene derivative, a perylene derivative, a fluorene derivative, an arylacetylene derivative, a styrylarylene derivative, a styrylamine derivative, an arylamine derivative, a boron complex, a coumarin derivative, a pyran derivative, a cyanine derivative, a croconium derivative, a squarium derivative, an oxobenzanthracene derivative, a fluorescein derivative, a rhodamine derivative, a pyrylium derivative, a perylene derivative, a polythiophene derivative, and a rare earth complex compound.

In addition, it has been developed a light emitting dopant utilizing delayed fluorescence. It may be used a light emitting dopant utilizing this type of fluorescence. Specific examples of utilizing delayed fluorescence are compounds described in: WO 2011/156793, JP-A 2011-213643, and JP-A 2010-93181. However, the present invention is not limited to them.

(1.3) Phosphorescence Emitting Dopant

A phosphorescence emitting dopant according to the present invention will be described.

The phosphorescence emitting dopant according to the present invention is a compound which is observed emission from an excited triplet state thereof. Specifically, it is a compound which emits phosphorescence at a room temperature (25° C.) and exhibits a phosphorescence quantum yield of at least 0.01 at 25° C. The phosphorescence quantum yield is preferably at least 0.1.

The phosphorescence quantum yield will be determined via a method described in page 398 of Bunko II of Dai 4 Han Jikken Kagaku Koza 7 (Spectroscopy II of 4th Edition Lecture of Experimental Chemistry 7) (1992, published by Maruzen Co. Ltd.). The phosphorescence quantum yield in a solution will be determined using appropriate solvents. However, it is only necessary for the phosphorescent dopant of the present invention to exhibit the above phosphorescence quantum yield (0.01 or more) using any of the appropriate solvents.

A phosphorescence dopant may be suitably selected and employed from the known materials used for a light emitting layer for an organic EL element.

Examples of a known phosphorescence dopant are compound described in the following publications.

Nature 395, 151 (1998), Appl. Phys. Lett. 78, 1622 (2001), Adv. Mater. 19, 739 (2007), Chem. Mater. 17, 3532 (2005), Adv. Mater. 17, 1059 (2005), WO 2009/100991, WO 2008/101842, WO 2003/040257, US 2006/835469, US 2006/0202194, US 2007/0087321, US 2005/0244673, Inorg. Chem. 40, 1704 (2001), Chem. Mater. 16, 2480 (2004), Adv. Mater. 16, 2003 (2004), Angew. Chem. Int. Ed. 2006, 45, 7800, Appl. Phys. Lett. 86, 153505 (2005), Chem. Lett. 34, 592 (2005), Chem. Commun. 2906 (2005), Inorg.

Chem. 42, 1248 (2003), WO 2009/050290, WO 2002/015645, WO 2009/000673, US 2002/0034656, U.S. Pat. No. 7,332,232, US 2009/0108737, US 2009/0039776, U.S. Pat. Nos. 6,921,915, 6,687,266, US 2007/0190359, US 2006/0008670, US 2009/0165846, US 2008/0015355, U.S. Pat. Nos. 7,250,226, 7,396,598, US 2006/0263635, US 2003/0138657, US 2003/0152802, U.S. Pat. No. 7,090,928, Angew. Chem. Int. Ed. 47, 1 (2008), Chem. Mater. 18, 5119 (2006), Inorg. Chem. 46, 4308 (2007), Organometallics 23, 3745 (2004), Appl. Phys. Lett. 74, 1361 (1999), WO 2002/002714, WO 2006/009024, WO 2006/056418, WO 2005/019373, WO 2005/123873, WO 2005/123873, WO 2007/004380, WO 2006/082742, US 2006/0251923, US 2005/0260441, U.S. Pat. Nos. 7,393,599, 7,534,505, 7,445,855, US 2007/0190359, US 2008/0297033, U.S. Pat. No. 7,338,722, US 2002/0134984, and U.S. Pat. No. 7,279,704, US 2006/098120, US 2006/103874, WO 2005/076380, WO 2010/032663, WO 2008/140115, WO 2007/052431, WO 2011/134013, WO 2011/157339, WO 2010/086089, WO 2009/113646, WO 2012/020327, WO 2011/051404, WO 2011/004639, WO 2011/073149, JP-A 2012-069737, JP Application No. 2011-181303, JP-A 2009-114086, JP-A 2003-81988, JP-A 2002-302671 and JP-A 2002-363552.

Among them, preferable phosphorescence emitting dopants are organic metal complexes containing Ir as a center metal. More preferable are complexes containing at least one coordination mode selected from a metal-carbon bond, a metal-nitrogen bond, a metal-oxygen bond and a metal-sulfur bond.

(2) Host Compound

A host compound according to the present invention is a compound which mainly plays a role of injecting or transporting a charge in a light emitting layer. In an organic EL element, an emission from the host compound itself is substantially not observed.

Among the compounds incorporated in the light emitting layer, a mass ratio of the host compound in the aforesaid layer is preferably at least 20%.

Host compounds may be used singly or may be used in combination of two or more compounds. By using plural host compounds, it is possible to adjust transfer of charge, thereby it is possible to achieve high efficiency of an organic EL element.

In the following, preferable host compounds used in the present invention will be described.

A host compound may be a π-conjugated compound used in the present invention as described above. However it is not specifically limited to that. From the viewpoint of a reverse energy transfer, it is preferable that the host compound has a larger excited energy level than an excited singlet energy level of the dopant compound. It is more preferable that the host compound has a larger excited triplet energy level than an excited triplet energy level of the dopant.

A host compound bears the function of transfer of the carrier and generation of an exciton in the light emitting layer. Therefore, it is preferable that the host compound will exist in all of the active species of a cation radical state, an anion radial state and an excited state, and that it will not make chemical reactions such as decomposition and addition. Further, it is preferable that the host molecule will not move in the layer with an Angstrom level when an electric current is applied.

In particular, when the jointly used light emitting dopant exhibits TADF emission, since the lifetime of the triplet excited state of the TADF material is long, it is required an appropriate design of a molecular structure to prevent the host compound from having a lower $T_1$ level such as: the host compound has a high $T_1$ energy; the host compounds will not form a low $T_1$ state when aggregated each other; the TADF material and the host compound will not form an exciplex; and the host compound will not form an electromer by applying an electric field.

In order to satisfy the above-described requirements, it is required that: the host compound itself has a high hopping mobility; the host compound has high hole hopping mobility; and the host compound has small structural change when it becomes a triplet excited state. As a representative host compound satisfying these requirements, preferable compounds are: a compound having a high $T_1$ energy such as a carbazole structure, an azacarbazole structure, a dibenzofuran structure, a dibenzothiophene structure and an azadibenzofuran structure. In particular, when the light emitting layer contains a carbazole derivative, it will promote suitable carrier hopping in the light emitting layer and suitable dispersion of the emitting material. Thereby it may be obtained the effect of improved emitting property and improved stability of the thin layer. It is a preferable embodiment.

A host compound has a hole transporting ability or an electron transporting ability, as well as preventing elongation of an emission wavelength. In addition, from the viewpoint of stably driving an organic EL element at high temperature, it is preferable that a host compound has a high glass transition temperature (T) of 90° C. or more, more preferably, has a Tg of 120° C. or more.

Here, a glass transition temperature (Tg) is a value obtained using DSC (Differential Scanning Colorimetry) based on the method in conformity to JIS-K-7121-2012.

A host compound suitably used in the present invention is a π-conjugated compound according to the present invention as described above. The reason of this is that the π-conjugated compound of the present invention has a condensed ring structure and the π-electron cloud is extended. As a result, the compound has high carrier transport ability and a high glass transition temperature (Tg). Further, the π-conjugated compound of the present invention has a high triplet energy $(T_1)$, and it is appropriately used for an emission of short wavelength (namely, having large $T_1$ and $S_1$).

As specific examples of a known host compound used in an organic EL element of the present invention, the compounds described in the following Documents are cited. However, the present invention is not to them.

Japanese patent application publication (JP-A) Nos. 2001-257076, 2002-308855, 2001-313179, 2002-319491, 2001-357977, 2002-334786, 2002-8860, 2002-334787, 2002-15871, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084 and 2002-308837; US Patent Application Publication (US) Nos. 2003/0175553, 2006/0280965, 2005/0112407, 2009/0017330, 2009/0030202, 2005/0238919; WO 2001/039234, WO2009/021126, WO 2008/056746, WO 2004/093 207, WO 2005/089025, WO 2007/063796, WO2007/063754, WO2004/107822, WO2005/030900, WO2006/114966, WO 2009/086028, WO 2009/003898, WO 2012/023947, JP-A 2008-074939, JP-A 2007-254297, EP 2034538, WO 2011/055933, and WO 2012/035853. The specific host compounds which may be used in the present invention are: Compounds H-1 to H-231 in paragraphs [0255] to [0293] of JP-A No.

2015-38941, or H-232 to H-236 as described in the following. However, the host compounds in the present invention are not limited to them.

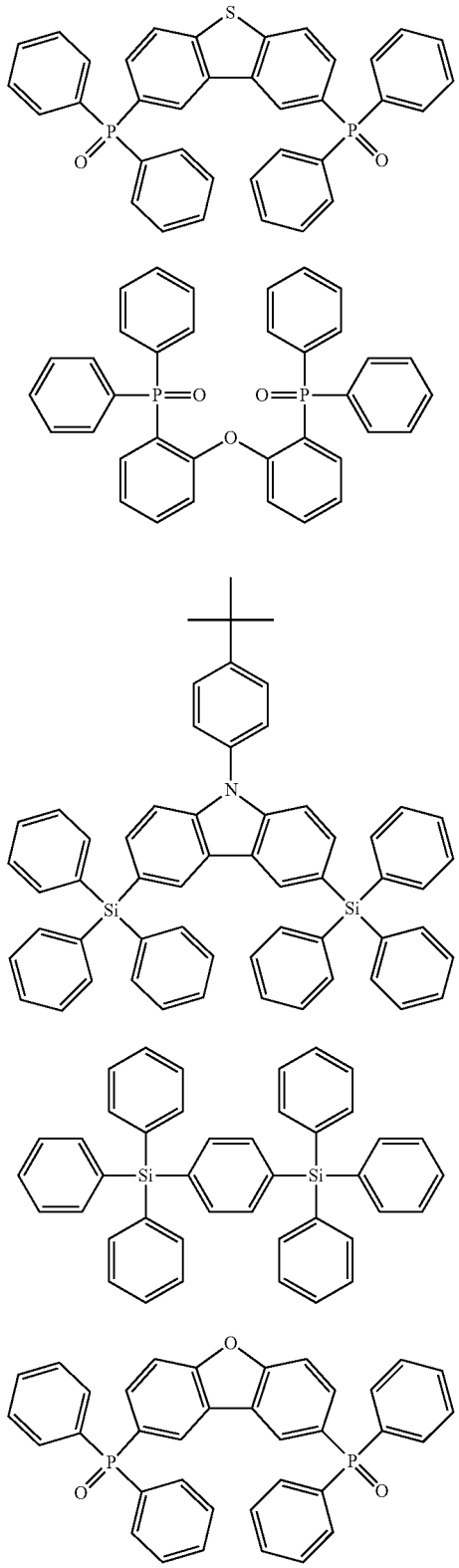

A preferable host compound used for the present invention may be a low molecular weight compound which has a molecular weight enabling to be purified with sublimation, or it may be a polymer having a repeating unit.

The low molecular weight compound has an advantage of obtaining a highly purified material since it is possible to purify with sublimation. The molecular weight thereof is not specifically limited as long as it is possible to purify with sublimation. A preferable molecular weight is 3,000 or less, and a more preferable molecular weight is 2,000 or less.

A polymer or an oligomer having a repeating unit has an advantage of easily forming a film with a wet process. In addition, since a polymer has generally a high Tg, the polymer is preferable from the viewpoint of heat resistivity.

<<Electron Transport Layer>>

An electron transport layer of the present invention is composed of a material having a function of transferring an electron. It is only required to have a function of transporting an injected electron from a cathode to a light emitting layer.

A total layer thickness of the electron transport layer is not specifically limited, however, it is generally in the range of 2 nm to 5 μm, and preferably, it is in the range of 2 to 500 nm, and more preferably, it is in the range of 5 to 200 nm.

In an organic EL element of the present invention, it is known that there occurs interference between the light directly taken from the light emitting layer and the light reflected at the electrode located at the opposite side of the electrode from which the light is taken out at the moment of taking out the light which is produced in the light emitting layer. When the light is reflected at the cathode, it is possible to use effectively this interference effect by suitably adjusting the total thickness of the electron transport layer in the range of several nm to several μm.

On the other hand, the voltage will be increased when the layer thickness of the electron transport layer is made thick. Therefore, especially when the layer thickness is large, it is preferable that the electron mobility in the electron transport layer is $1\times10^{-5}$ cm$^2$/Vs or more.

As a material used for an electron transport layer (hereafter, it is called as an electron transport material), it is only required to have either a property of ejection or transport of electrons, or a barrier to holes. Any of the conventionally known compounds may be selected and they may be employed.

Cited examples thereof include: a nitrogen-containing aromatic heterocyclic derivative (a carbazole derivative, an azacarbazole derivative (a compound in which one or more carbon atoms constituting the carbazole ring are substitute with nitrogen atoms), a pyridine derivative, a pyrimidine derivative, a pyrazine derivative, a pyridazine derivative, a triazine derivative, a quinoline derivative, a quinoxaline derivative, a phenanthroline derivative, an azatriphenylene derivative, an oxazole derivative, a thiazole derivative, an oxadiazole derivative, a thiadiazole derivative, a triazole derivative, a benzimidazole derivative, a benzoxazole derivative, and a benzothiazole derivative); a dibenzofuran derivative, a dibenzothiophene derivative, a silole derivative; and an aromatic hydrocarbon ring derivative (a naphthalene derivative, an anthracene derivative and a triphenylene derivative).

Further, metal complexes having a ligand of a 8-quinolinol structure or dibnenzoquinolinol structure such as tris(8-quinolinol)aluminum (Alq$_3$),
tris(5, 7-dichloro-8-quinolinol)aluminum,
tris(5, 7-dibromo-8-quinolinol)aluminum,
tris(2-methyl-8-quinolinol)aluminum,
tris(5-methyl-8-quinolinol)aluminum and bis(8-quinolinol)zinc (Znq); and metal complexes in which a central metal of the aforesaid metal complexes is substituted by In, Mg, Cu, Ca, Sn, Ga or Pb, may be also utilized as an electron transport material.

Further, a metal-free or metal phthalocyanine, or a compound whose terminal is substituted by an alkyl group or a sulfonic acid group, may be preferably utilized as an electron transport material. A distyryl pyrazine derivative, which is exemplified as a material for a light emitting layer, may be used as an electron transport material. Further, in the same manner as used for a hole injection layer and a hole transport layer, an inorganic semiconductor such as an n-type Si and an n-type SiC may be also utilized as an electron transport material.

It may be used a polymer material introduced these compounds in the polymer side-chain or a polymer material having any one of these substance in a polymer main chain.

In an electron transport layer according to the present invention, it is possible to employ an electron transport layer of a higher n property (electron rich) which is doped with impurities as a guest material. As examples of a dope material, listed are those described in each of JP-A Nos. 4-297076, 10-270172, 2000-196140, 2001-102175, as well as in J. Appl. Phys., 95, 5773 (2004).

Although the present invention is not limited thereto, preferable examples of a known electron transport material used in an organic EL element of the present invention are compounds described in the following publications.

U.S. Pat. Nos. 6,528,187, 7,230,107, US 2005/0025993, US 2004/0036077, US 2009/0115316, US 2009/0101870, US 2009/0179554, WO2003/060956, WO2008/132085, Appl. Phys. Lett. 75, 4 (1999), Appl. Phys. Lett. 79, 449 (2001), Appl. Phys. Lett. 81, 162 (2002), Appl. Phys. Lett. 81, 162 (2002), Appl. Phys. Lett. 79, 156 (2001), U.S. Pat. No. 7,964,293, US 2009/030202, WO 2004/080975, WO 2004/063159, WO 2005/085387, WO 2006/067931, WO2007/086552, WO2008/114690, WO2009/069442, WO2009/066779, WO2009/054253, WO2011/086935, WO2010/150593, WO2010/047707, EP 2311826, JP-A 2010-251675, JP-A 2009-209133, JP-A 2009-124114, JP-A 2008-277810, JP-A 2006-156445, JP-A 2005-340122, JP-A 2003-45662, JP-A 2003-31367, JP-A 2003-282270, and WO 2012/115034.

As a preferable electron transport material, it may be cited an aromatic heterocyclic ring compound containing at least one nitrogen atom. Examples thereof are: a pyridine derivative, a pyrimidine derivative, a pyrazine derivative, a triazine derivative, a dibenzofuran derivative, a dibenzothiophene derivative, a carbazole derivative, an azacarbazole derivative, and a benzimidazole derivative. An electron transport material may be used singly, or may be used in combination of plural kinds of compounds.

<<Hole Blocking Layer>>

A hole blocking layer is a layer provided with a function of an electron transport layer in a broad meaning. Preferably, it contains a material having a function of transporting an electron, and having very small ability of transporting a hole. It will improve the recombination probability of an electron and a hole by blocking a hole while transporting an electron.

Further, a composition of an electron transport layer described above may be appropriately utilized as a hole blocking layer of the present invention when needed.

A hole blocking layer placed in an organic EL element of the present invention is preferably arranged at a location in the light emitting layer adjacent to the cathode side.

A thickness of a hole blocking layer according to the present invention is preferably in the range of 3 to 100 nm, and more preferably, in the range of 5 to 30 nm.

With respect to a material used for a hole blocking layer, the material used in the aforesaid electron transport layer is suitably used, and further, the material used as the aforesaid host compound is also suitably used for a hole blocking layer.

<<Electron Injection Layer>>

An electron injection layer (it is also called as "a cathode buffer layer") according to the present invention is a layer which is arranged between a cathode and a light emitting layer to decrease an operating voltage and to improve an emission luminance. An example of an electron injection layer is detailed in volume 2, chapter 2 "Electrode materials" (pp. 123-166) of "Organic EL Elements and Industrialization Front thereof (Nov. 30, 1998, published by N.T.S. Co. Ltd.)".

In the present invention, an electron injection layer is provided according to necessity, and as described above, it is placed between a cathode and a light emitting layer, or between a cathode and an electron transport layer.

An electron injection layer is preferably a very thin layer. The layer thickness thereof is preferably in the range of 0.1 to 5 nm depending on the materials used.

An election injection layer is detailed in JP-A Nos. 6-325871, 9-17574, and 10-74586. Examples of a material preferably used in an election injection layer include: a metal such as strontium and aluminum; an alkaline metal compound such as lithium fluoride, sodium fluoride, or potassium fluoride; an alkaline earth metal compound such as magnesium fluoride; a metal oxide such as aluminum oxide; and a metal complex such as lithium 8-hydroxyquinolate (Liq). It is possible to use the aforesaid electron transport materials.

The above-described materials may be used singly or plural kinds may be used together in an election injection layer.

<<Hole Transport Layer>>

In the present invention, a hole transport layer contains a material having a function of transporting a hole. A hole transport layer is only required to have a function of transporting a hole injected from an anode to a light emitting layer.

The total layer thickness of a hole transport layer of the present invention is not specifically limited, however, it is generally in the range of 0.5 nm to 5 μm, preferably in the range of 2 to 500 nm, and more preferably in the range of 5 to 200 nm.

A material used in a hole transport layer (hereafter, it is called as a hole transport material) is only required to have any one of properties of injecting and transporting a hole, and a barrier property to an electron. A hole transport material may be suitably selected from the conventionally known compounds.

Examples of a hole transport material include: a porphyrin derivative, a phthalocyanine derivative, an oxazole derivative, an oxadiazole derivative, a triazole derivative, an imidazole derivative, a pyrazoline derivative, a pyrazolone derivative, a phenylenediamine derivative, a hydrazone derivative, a stilbene derivative, a polyarylalkane derivative, a triarylamine derivative, a carbazole derivative, an indolocarbazole derivative, an isoindole derivative, an acene derivative of anthracene or naphthalene, a fluorene derivative, a fluorenone derivative, polyvinyl carbazole, a polymer or an oligomer containing an aromatic amine in a side chain or a main chain, polysilane, and a conductive polymer or an oligomer (e.g., PEDOT:PSS, an aniline type copolymer, polyaniline and polythiophene).

Examples of a triarylamine derivative include: a benzidine type represented by α-NPD (4,4'-bis[N-(1-naphthyl)-N-phenyamino]biphenyl), a star burst type represented by MTDATA (4,4',4"-tris(N-(3-methylphenyl)-N-phenylamino) triphenylamine), a compound having fluorenone or anthracene in a triarylamine bonding core.

A hexaazatriphenylene derivative described in JP-A Nos. 2003-519432 and 2006-135145 may be also used as a hole transport material.

In addition, it is possible to employ an electron transport layer of a higher p property which is doped with impurities. As its example, listed are those described in each of JP-A Nos. 4-297076, 2000-196140, and 2001-102175, as well as in J. Appl. Phys., 95, 5773 (2004).

Further, it is possible to employ so-called p-type hole transport materials, and inorganic compounds such as p-type Si and p-type SiC, as described in JP-A No. 11-251067, and J. Huang et al. reference (Applied Physics Letters 80 (2002), p. 139). Moreover, an orthometal compounds having Ir or Pt as a center metal represented by Ir(ppy)$_3$ are also preferably used.

Although the above-described compounds may be used as a hole transport material, preferably used are: a triarylamine derivative, a carbazole derivative, an indolocarbazole derivative, an azatriphenylene derivative, an organic metal complex, a polymer or an oligomer incorporated an aromatic amine in a main chain or in a side chain.

Specific examples of a known hole transport material used in an organic EL element of the present invention are compounds in the aforesaid publications and in the following publications. However, the present invention is not limited to them.

Examples of a publication are: Appl. Phys. Lett. 69, 2160(1996), J. Lumin. 72-74, 985(1997), Appl. Phys. Lett. 78, 673(2001), Appl. Phys. Lett. 90, 183503(2007), Appl. Phys. Lett. 51, 913(1987), Synth. Met. 87, 171(1997), Synth. Met. 91, 209(1997), Synth. Met. 111, 421(2000), SID Symposium Digest, 37, 923(2006), J. Mater. Chem. 3, 319(1993), Adv. Mater. 6, 677(1994), Chem. Mater. 15, 3148(2003), US 2003/0162053, US 2002/0158242, US 2006/0240279, US 2008/0220265, U.S. Pat. No. 5,061,569, WO 2007/002683, WO 2009/018009, EP 650955, US 2008/0124572, US 2007/0278938, US 2008/0106190, US 2008/0018221, WO 2012/115034, JP-A 2003-519432, JP-A 2006-135145, and U.S. patent application Ser. No. 13/585,981.

A hole transport material may be used singly or may be used in combination of plural kinds of compounds.

<<Electron Blocking Layer>>

An electron blocking layer is a layer provided with a function of a hole transport layer in a broad meaning. Preferably, it contains a material having a function of transporting a hole, and having very small ability of transporting an electron. It will improve the recombination probability of an electron and a hole by blocking an electron while transporting a hole. Further, a composition of a hole transport layer described above may be appropriately utilized as an electron blocking layer of an organic EL element of the present invention when needed.

An electron blocking layer placed in an organic EL element of the present invention is preferably arranged at a location in the light emitting layer adjacent to the anode side.

A thickness of an electron blocking layer is preferably in the range of 3 to 100 nm, and more preferably, in the range of 5 to 30 nm.

With respect to a material used for an electron blocking layer, the material used in the aforesaid hole transport layer is suitably used, and further, the material used as the aforesaid host compound is also suitably used for an electron blocking layer.

<<Hole Injection Layer>>

A hole injection layer (it is also called as "an anode buffer layer") is a layer which is arranged between an electrode and a light emitting layer to decrease an operating voltage and to improve an emission luminance. An example of a hole injection layer is detailed in volume 2, chapter 2 "Electrode materials" (pp. 123-166) of "Organic EL Elements and Industrialization Front thereof (Nov. 30, 1998, published by N.T.S. Co. Ltd.)".

A hole injection layer is provided according to necessity, and as described above, it is placed between an anode and a light emitting layer, or between an anode and a hole transport layer.

A hole injection layer is also detailed in JP-A Nos. 9-45479, 9-260062 and 8-288069. Materials used in the hole injection layer are the same materials used in the aforesaid hole transport layer.

Among them, preferable materials are: a phthalocyanine derivative represented by copper phthalocyanine; a hexaazatriphenylene derivative described in JP-A Nos. 2003-519432 and 2006-135145; a metal oxide represented by vanadium oxide; a conductive polymer such as amorphous carbon, polyaniline (or called as emeraldine) and polythiophene; an orthometalated complex represented by tris(2-phenylpyridine) iridium complex; and a triarylamine derivative.

The above-described materials used in a hole injection layer may be used singly or plural kinds may be co-used.

<<Additive>>

The above-described organic layer of the present invention may further contain other additive.

Examples of an additive are: halogen elements such as bromine, iodine and chlorine, and a halide compound; and a compound, a complex and a salt of an alkali metal, an alkaline earth metal and a transition metal such as Pd, Ca and Na.

Although a content of an additive may be arbitrarily decided, preferably, it is 1,000 ppm or less based on the total mass of the layer containing the additive, more preferably, it is 500 ppm or less, and still more preferably, it is 50 ppm or less.

In order to improve a transporting porporty of an electron or a hole, or to facilitate energy transport of an exciton, the content of the additive is not necessarily within these range, and other range of content may be used.

<<Forming Method of Organic Layers>>

It will be described forming methods of organic layers according to the present invention (hole injection layer, hole transport layer, light emitting layer, hole blocking layer, electron transport layer, and electron injection layer).

Forming methods of organic layers according to the present invention are not specifically limited. They may be formed by using a known method such as a vacuum vapor deposition method and a wet method (wet process).

Examples of a wet process include: a spin coating method, a cast method, an inkjet method, a printing method, a die coating method, a blade coating method, a roll coating method, a spray coating method, a curtain coating method, and a LB method (Langmuir Blodgett method). From the viewpoint of getting a uniform thin layer with high productivity, preferable are method highly appropriate to a roll-to-roll method such as a die coating method, a roll coating method, an inkjet method, and a spray coating method.

Examples of a liquid medium to dissolve or to disperse a material for organic layers according to the present invention include: ketones such as methyl ethyl ketone and cyclohexanone; aliphatic esters such as ethyl acetate; halogenated hydrocarbons such as dichlorobenzene; aromatic hydrocarbons such as toluene, xylene, mesitylene, and cyclohexylbenzene; aliphatic hydrocarbons such as cyclohexane, decalin, and dodecane; organic solvents such as DMF and DMSO.

These will be dispersed with a dispersion method such as an ultrasonic dispersion method, a high shearing dispersion method and a media dispersion method.

A different film forming method may be applied to every organic layer. When a vapor deposition method is adopted for forming each layer, the vapor deposition conditions may be changed depending on the compounds used. Generally, the following ranges are suitably selected for the conditions, heating temperature of boat: 50 to 450° C., level of vacuum: $1\times10^{-6}$ to $1\times10^{-2}$ Pa, vapor deposition rate: 0.01 to 50 nm/sec, temperature of substrate: −50 to 300° C., and layer thickness: 0.1 nm to 5 μm, preferably 5 to 200 nm.

Formation of organic layers of the present invention is preferably continuously carried out from a hole injection layer to a cathode with one time vacuuming. It may be taken out on the way, and a different layer forming method may be employed. In that case, the operation is preferably done under a dry inert gas atmosphere.

<<Anode>>

As an anode of an organic EL element, a metal having a large work function (4 eV or more, preferably, 4.5 eV or more), an alloy, and a conductive compound and a mixture thereof are utilized as an electrode substance.

Specific examples of an electrode substance are: metals such as Au, and an alloy thereof; transparent conductive materials such as CuI, indium tin oxide (ITO), $SnO_2$, and ZnO. Further, a material such as IDIXO ($In_2O_3$—ZnO), which may form an amorphous and transparent electrode, may also be used.

As for an anode, these electrode substances may be made into a thin layer by a method such as a vapor deposition method or a sputtering method; followed by making a pattern of a desired form by a photolithography method. Otherwise, when the requirement of pattern precision is not so severe (about 100 μm or more), a pattern may be formed through a mask of a desired form at the time of layer formation with a vapor deposition method or a sputtering method using the above-described material.

Alternatively, when a coatable substance such as an organic conductive compound is employed, it is possible to employ a wet film forming method such as a printing method or a coating method. When emitted light is taken out from the anode, the transmittance is preferably set to be 10% or more. A sheet resistance of the anode is preferably a few hundred Ω/sq or less.

Further, although a layer thickness of the anode depends on a material, it is generally selected in the range of 10 nm to 1 μm, and preferably in the range of 10 to 200 nm.

<<Cathode>>

As a cathode, a metal having a small work function (4 eV or less) (it is called as an electron injective metal), an alloy, a conductive compound and a mixture thereof are utilized as an electrode substance. Specific examples of the aforesaid electrode substance includes: sodium, sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, aluminum, and a rare earth metal. Among them, with respect to an electron injection property and durability against oxidation, preferable are: a mixture of election injecting metal with a second metal which is stable metal having a work function larger than the electron injecting metal. Examples thereof are: a magnesium/silver mixture, a magnesium/aluminum mixture, a magnesium/indium mixture, an aluminum/aluminum oxide ($Al_2O_3$) mixture, a lithium/aluminum mixture and aluminum.

A cathode may be made by using these electrode substances with a method such as a vapor deposition method or a sputtering method to form a thin film. A sheet resistance of the cathode is preferably a few hundred Q/sq or less. A layer thickness of the cathode is generally selected in the range of 10 nm to 5 μm, and preferably in the range of 50 to 200 nm.

In order to transmit emitted light, it is preferable that one of an anode and a cathode of an organic EL element is transparent or translucent for achieving an improved luminescence.

Further, after forming a layer of the aforesaid metal having a thickness of 1 to 20 nm on the cathode, it is possible to prepare a transparent or translucent cathode by providing with a conductive transparent material described in the description for the anode thereon. By applying this process, it is possible to produce an element in which both an anode and a cathode are transparent.

[Support Substrate]

A support substrate which may be used for an organic EL element of the present invention is not specifically limited with respect to types such as glass and plastics. Hereafter, the support substrate may be also called as substrate body, substrate, substrate substance, or support. They may be transparent or opaque. However, a transparent support substrate is preferable when the emitting light is taken from the side of the support substrate. Support substrates preferably utilized includes such as glass, quartz and transparent resin film. A specifically preferable support substrate is a resin film capable of providing an organic EL element with a flexible property.

Examples of a resin film include: polyesters such as polyethylene terephthalate (PET) and polyethylene naphthalate (PEN), polyethylene, polypropylene, cellophane, cellulose esters and their derivatives such as cellulose diacetate, cellulose triacetate (TAC), cellulose acetate butyrate, cellulose acetate propionate (CAP), cellulose acetate phthalate, and cellulose nitrate, polyvinylidene chloride, polyvinyl alcohol, polyethylene vinyl alcohol, syndiotactic polystyrene, polycarbonate, norbornene resin, polymethyl pentene, polyether ketone, polyimide, polyether sulfone (PES), polyphenylene sulfide, polysulfones, polyether imide, polyether ketone imide, polyamide, fluororesin, Nylon, polymethyl methacrylate, acrylic resin, polyallylates and cycloolefin resins such as ARTON (trade name, made by JSR Co. Ltd.) and APEL (trade name, made by Mitsui Chemicals, Inc.).

On the surface of a resin film, it may be formed a film incorporating an inorganic or an organic compound or a hybrid film incorporating both compounds. Barrier films are preferred with a water vapor permeability of 0.01 g/m²·24 h or less (at 25±0.5° C., and 90±2% RH) determined based on JIS K7129-1992. Further, high barrier films are preferred to have an oxygen permeability of $1\times10^{-3}$ cm³/m²·24 h·atm or less determined based on JIS K 7126-1987, and a water vapor permeability 1 of $1\times10^{-5}$ g/m²·24 h or less.

As materials that form a barrier film, employed may be those which retard penetration of moisture and oxygen, which deteriorate the element. For example, it is possible to employ silicon oxide, silicon dioxide, and silicon nitride.

Further, in order to improve the brittleness of the aforesaid film, it is more preferable to achieve a laminated layer structure of inorganic layers and organic layers. The laminating order of the inorganic layer and the organic layer is not particularly limited, but it is preferable that both are alternatively laminated a plurality of times.

Barrier film forming methods are not particularly limited, and examples of employable methods include a vacuum deposition method, a sputtering method, a reactive sputtering method, a molecular beam epitaxy method, a cluster ion beam method, an ion plating method, a plasma polymerization method, a plasma CVD method, a laser CVD method, a thermal CVD method, and a coating method. Of these, specifically preferred is a method employing an atmospheric pressure plasma polymerization method, described in JP-A No. 2004-68143.

Examples of opaque support substrates include metal plates such aluminum or stainless steel films, opaque resin substrates, and ceramic substrates.

An external taking out quantum efficiency of light emitted by the organic EL element of the present invention is preferably at least 1% at a room temperature, but is more preferably at least 5%.

External taking out quantum efficiency (%)=(Number of photons emitted by the organic EL element to the exterior/Number of electrons fed to organic EL element)×100.

Further, it may be used simultaneously a color hue improving filter such as a color filter, or it may be used simultaneously a color conversion filter which convert emitted light color from the organic EL element to multicolor by employing fluorescent materials.

[Sealing]

As sealing means employed in the present invention, listed may be, for example, a method in which sealing members, electrodes, and a supporting substrate are subjected to adhesion via adhesives. The sealing members may be arranged to cover the display region of an organic EL element, and may be a concave plate or a flat plate. Neither transparency nor electrical insulation is limited.

Specifically listed are glass plates, polymer plate-films, metal plate-films. Specifically, it is possible to list, as glass plates, soda-lime glass, barium-strontium containing glass, lead glass, aluminosilicate glass, borosilicate glass, barium borosilicate glass, and quartz. Further, listed as polymer plates may be polycarbonate, acryl, polyethylene terephthalate, polyether sulfide, and polysulfone. As a metal plate, listed are those composed of at least one metal selected from the group consisting of stainless steel, iron, copper, aluminum magnesium, nickel, zinc, chromium, titanium, molybdenum, silicon, germanium, and tantalum, or alloys thereof.

In the present invention, since it is possible to achieve a thin organic EL element, it is preferable to employ a polymer film or a metal film. Further, it is preferable that the polymer film has an oxygen permeability of $1\times10^{-3}$ cm$^3$/m$^2$·24 h·atm or less determined by the method based on JIS K 7126-1987, and a water vapor permeability of $1\times10^{-3}$ g/m$^2$·24 h or less (at 25±0.5° C., and 90±2% RH) determined by the method based on JIS K 7129-1992.

Conversion of the sealing member into concave is carried out by employing a sand blast process or a chemical etching process.

In practice, as adhesives, listed may be photo-curing and heat-curing types having a reactive vinyl group of acrylic acid based oligomers and methacrylic acid, as well as moisture curing types such as 2-cyanoacrylates. Further listed may be thermal and chemical curing types (mixtures of two liquids) such as epoxy based ones. Still further listed may be hot-melt type polyamides, polyesters, and polyolefins. Yet further listed may be cationically curable type UV curable epoxy resin adhesives.

In addition, since an organic EL element is occasionally deteriorated via a thermal process, preferred are those which enable adhesion and curing between a room temperature and 80° C. Further, desiccating agents may be dispersed into the aforesaid adhesives. Adhesives may be applied onto sealing portions via a commercial dispenser or printed on the same in the same manner as screen printing.

Further, it is appropriate that on the outside of the aforesaid electrode which interposes the organic layer and faces the support substrate, the aforesaid electrode and organic layer are covered, and in the form of contact with the support substrate, inorganic and organic material layers are formed as a sealing film. In this case, as materials that form the aforesaid film may be those which exhibit functions to retard penetration of moisture or oxygen which results in deterioration. For example, it is possible to employ silicon oxide, silicon dioxide, and silicon nitride.

Still further, in order to improve brittleness of the aforesaid film, it is preferable that a laminated layer structure is formed, which is composed of these inorganic layers and layers composed of organic materials. Methods to form these films are not particularly limited. It is possible to employ, for example, a vacuum deposition method, a sputtering method, a reactive sputtering method, a molecular beam epitaxy method, a cluster ion beam method, an ion plating method, a plasma polymerization method, an atmospheric pressure plasma polymerization method, a plasma CVD method, a thermal CVD method, and a coating method.

It is preferable to inject a gas phase and a liquid phase material of inert gases such as nitrogen or argon, and inactive liquids such as fluorinated hydrocarbon or silicone oil into the space between the space formed with the sealing member and the display region of the organic EL element. Further, it is possible to form vacuum in the space. Still further, it is possible to enclose hygroscopic compounds in the interior of the space.

Examples of a hygroscopic compound include: metal oxides (for example, sodium oxide, potassium oxide, calcium oxide, barium oxide, magnesium oxide, and aluminum oxide); sulfates (for example, sodium sulfate, calcium sulfate, magnesium sulfate, and cobalt sulfate); metal halides (for example, calcium chloride, magnesium chloride, cesium fluoride, tantalum fluoride, cerium bromide, magnesium bromide, barium iodide, and magnesium iodide); perchlorates (for example, barium perchlorate and magnesium perchlorate). In sulfates, metal halides, and perchlorates, suitably employed are anhydrides. For sulfate salts, metal halides and perchlorates, suitably used are anhydrous salts.

[Protective Film and Protective Plate]

On the aforesaid sealing film which interposes the organic layer and faces the support substrate or on the outside of the aforesaid sealing film, a protective or a protective plate may be arranged to enhance the mechanical strength of the element. Specifically, when sealing is achieved via the aforesaid sealing film, the resulting mechanical strength is not always high enough, therefore it is preferable to arrange the protective film or the protective plate described above. Usable materials for these include glass plates, polymer plate-films, and metal plate-films which are similar to those employed for the aforesaid sealing. However, from the viewpoint of reducing weight and thickness, it is preferable to employ a polymer film.

[Improving Method of Light Extraction]

It is generally known that an organic EL element emits light in the interior of the layer exhibiting the refractive index (being about 1.6 to 2.1) which is greater than that of air, whereby only about 15% to 20% of light generated in the light emitting layer is extracted. This is due to the fact that light incident to an interface (being an interlace of a transparent substrate to air) at an angle of θ which is at least critical angle is not extracted to the exterior of the element due to the resulting total reflection, or light is totally reflected between the transparent electrode or the light emitting layer and the transparent substrate, and light is guided via the transparent electrode or the light emitting layer, whereby light escapes in the direction of the element side surface.

Means to enhance the efficiency of the aforesaid light extraction include, for example: a method in which roughness is formed on the surface of a transparent substrate, whereby total reflection is minimized at the interface of the transparent substrate to air (U.S. Pat. No. 4,774,435), a method in which efficiency is enhanced in such a manner that a substrate results in light collection (JP-A No. 63-314795), a method in which a reflection surface is formed on the side of the element (JP-A No. 1-220394), a method in which a flat layer of a middle refractive index is introduced between the substrate and the light emitting body and an antireflection film is formed (JP-A No. 62-172691), a method in which a flat layer of a refractive index which is equal to or less than the substrate is introduced between the substrate and the light emitting body (JP-A No. 2001-202827), and a method in which a diffraction grating is formed between the substrate and any of the layers such as the transparent electrode layer or the light emitting layer (including between the substrate and the outside) (JP-A No. 11-283751).

In the present invention, it is possible to employ these methods while combined with the organic EL element of the present invention. Of these, it is possible to appropriately employ the method in which a flat layer of a refractive index which is equal to or less than the substrate is introduced between the substrate and the light emitting body and the method in which a diffraction grating is formed between any layers of a substrate, and a transparent electrode layer and a light emitting layer (including between the substrate and the outside space).

By combining these means, the present invention enables the production of elements which exhibit higher luminance or excel in durability.

When a low refractive index medium having a thickness, greater than the wavelength of light is formed between the transparent electrode and the transparent substrate, the extraction efficiency of light emitted from the transparent electrode to the exterior increases as the refractive index of the medium decreases.

As materials of the low refractive index layer, listed are, for example, aerogel, porous silica, magnesium fluoride, and fluorine based polymers. Since the refractive index of the transparent substrate is commonly about 1.5 to 1.7, the refractive index of the low refractive index layer is preferably approximately 1.5 or less. More preferably, it is 1.35 or less.

Further, thickness of the low refractive index medium is preferably at least two times of the wavelength in the medium. The reason is that, when the thickness of the low refractive index medium reaches nearly the wavelength of light so that electromagnetic waves escaped via evanescent enter into the substrate, effects of the low refractive index layer are lowered.

The method in which the interface which results in total reflection or a diffraction grating is introduced in any of the media is characterized in that light extraction efficiency is significantly enhanced. The above method works as follows. By utilizing properties of the diffraction grating capable of changing the light direction to the specific direction different from diffraction via so-called Bragg diffraction such as primary diffraction or secondary diffraction of the diffraction grating, of light emitted from the light entitling layer, light, which is not emitted to the exterior due to total reflection between layers, is diffracted via introduction of a diffraction grating between any layers or in a medium (in the transparent substrate and the transparent electrode) so that light is extracted to the exterior.

It is preferable that the introduced diffraction grating exhibits a two-dimensional periodic refractive index. The reason is as follows. Since light emitted in the light emitting layer is randomly generated to all directions, in a common one-dimensional diffraction grating exhibiting a periodic refractive index distribution only in a certain direction, light which travels to the specific direction is only diffracted, whereby light extraction efficiency is not sufficiently enhanced.

However, by changing the refractive index distribution to a two-dimensional one, light, which travels to all directions, is diffracted, whereby the light extraction efficiency is enhanced.

A position to introduce a diffraction grating may be between any layers or in a medium (in a transparent substrate or a transparent electrode). However, a position near the organic light emitting layer, where light is generated, is preferable. In this case, the cycle of the diffraction grating is preferably from about ½ to 3 times of the wavelength of light in the medium. The preferable arrangement of the diffraction grating is such that the arrangement is two-dimensionally repeated in the form of a square lattice, a triangular lattice, or a honeycomb lattice.

[Light Collection Sheet]

Via a process to arrange a structure such as a micro-lens array shape on the light extraction side of the organic EL element of the present invention or via combination with a so-called light collection sheet, light is collected in the specific direction such as the front direction with respect to the light emitting element surface, whereby it is possible to enhance luminance in the specific direction.

In an example of the micro-lens array, square pyramids to realize a side length of 30 μm and an apex angle of 90 degrees are two-dimensionally arranged on the light extraction side of the substrate. The side length is preferably 10 to 100 μm. When it is less than the lower limit, coloration occurs due to generation of diffraction effects, while when it exceeds the upper limit, the thickness increases undesirably.

It is possible to employ, as a light collection sheet, for example, one which is put into practical use in the LED backlight of liquid crystal display devices. It is possible to employ, as such a sheet, for example, the luminance enhancing film (BEF), produced by Sumitomo 3M Limited. As shapes of a prism sheet employed may be, for example, A shaped stripes of an apex angle of 90 degrees and a pitch of 50 μm formed on a base material, a shape in which the apex angle is rounded, a shape in which the pitch is randomly changed, and other shapes.

Further, in order to control the light radiation angle from the light emitting element, simultaneously employed may be a light diffusion plate-film. For example, it is possible to employ the diffusion film (LIGHT-UP), produced by Kimoto Co., Ltd.

[Applications]

It is possible to employ the organic EL element of the present invention as display devices, displays, and various types of light emitting sources.

Examples of light emitting sources include: lighting apparatuses (home lighting and car lighting), clocks, backlights for liquid crystals, sign advertisements, signals, light sources of light memory media, light sources of electrophotographic copiers, light sources of light communication processors, and light sources of light sensors. The present invention is not limited to them. It is especially effectively employed as a backlight of a liquid crystal display device and a lighting source.

If needed, the organic EL element of the present, invention may undergo patterning via a metal mask or an ink-jet printing method during film formation. When the patterning is carried out, only an electrode may undergo patterning, an electrode and a light emitting layer may undergo patterning, or all element layers may undergo patterning. During preparation of the element, it is possible to employ conventional methods.

<Display Device>

A display device provided with an organic EL element of the present invention may emit a single color or multiple colors. Here, it will be described a multiple color display device.

In case of a multiple color display device, a shadow mask is placed during the formation of a light emitting layer, and a layer is formed as a whole with a vapor deposition method, a cast method, a spin coating method, an inkjet method, and a printing method.

When patterning is done only to the light emitting layer, although the coating method is not limited in particular, preferable methods are a vapor deposition method, an inkjet method, a spin coating method, and a printing method.

A constitution of an organic EL element provided for a display device is selected from the above-described examples of an organic EL element according to the necessity.

The production method of an organic EL element is described as an embodiment of a production method of the above-described organic EL element.

When a direct-current voltage is applied to the produced multiple color display device, light emission may be observed by applying voltage of 2~40 V by setting the anode to have a plus (+) polarity, and the cathode to have a minus (−) polarity. When the voltage is applied to the device with reverse polarities, an electric current does not pass and light emission does not occur. Further, when an alternating-current voltage is applied to the device, light emission occurs only when the anode has a plus (+) polarity and the cathode has a minus (−) polarity. In addition, an arbitrary wave shape may be used for applying alternating-current.

The multiple color display device may be used for a display device, a display, and a variety of light emitting sources. In a display device or a display, a full color display is possible by using 3 kinds of organic EL elements emitting blue, red and green.

Examples of a display device or a display are: a television set, a personal computer, a mobile device, an AV device, a character broadcast display, and an information display in a car. Specifically, it may be used for a display device reproducing a still image or a moving image. When it is used for a display device reproducing a moving image, the driving mode may be any one of a passive-matrix mode and an active-matrix mode.

Examples of a light emitting source include: home lighting, car lighting, backlights for clocks and liquid crystals, sign advertisements, signals, light sources of light memory media, light sources of electrophotographic copiers, light sources of light communication processors, and light sources of light sensors. The present invention is not limited to them.

In the following, an example of a display device provided with an organic EL element of the present invention will be described by referring to drawings.

Figure 9:
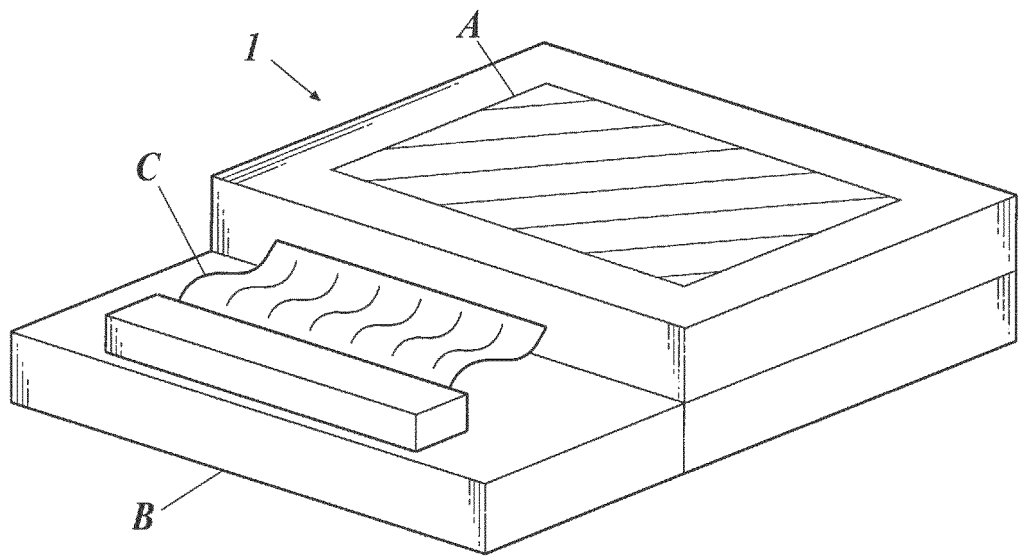
FIG. 9 is a schematic diagram illustrating an example of a display device including an organic EL element.

FIG. 9 is a schematic drawing illustrating an example of a display device composed of an organic EL element. Display of image information is carried out by light emission of an organic EL element. For example, it is a schematic drawing of a display of a cell-phone.

A display 1 is constituted of a display section A having plural number of pixels, a control section B which performs image scanning of the display section A based on image information, and a wiring section C electrically connecting the display section A and the control section B.

The control section B, which is electrically connected to the display section A via the wiring section C, sends a scanning signal and an image data signal to plural number of pixels based on image information from the outside and pixels of each scanning line successively emit depending on the image data signal by a scanning signal to perform image scanning, whereby image information is displayed on the display section A.

Figure 10:
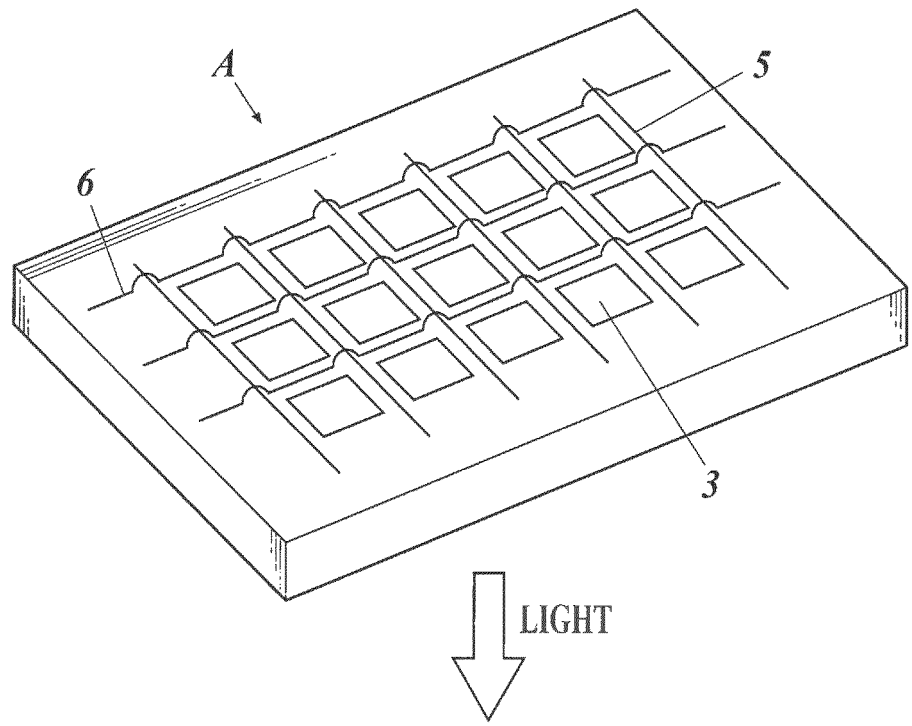
FIG. 10 is a schematic diagram of a display device by an active matrix mode.

FIG. 10 is a schematic drawing of the display section A based on an active matrix mode.

The display section A is provided with the wiring section C, which contains plural scanning lines 5 and data lines 6, and plural pixels 3 on a substrate. Primary part materials of the display section A will be explained in the following.

In FIG. 10, illustrated is the case that light emitted by the pixel 3 is taken out along the white allow (downward).

The scanning lines 5 and the plural data lines 6 each are comprised of a conductive material, and the scanning lines 5 and the data lines 6 are perpendicular in a grid form and are connected to pixels 3 at the right-angled crossing points (details are not shown in the drawing).

The pixel 3 receives an image data from the data line 6 when a scanning signal is applied from the scanning line 5 and emits according to the received image data.

Full-color display is possible by appropriately arranging pixels having an emission color in a red region, pixels in a green region and pixels in a blue region, side by side on the same substrate.

Figure 11:
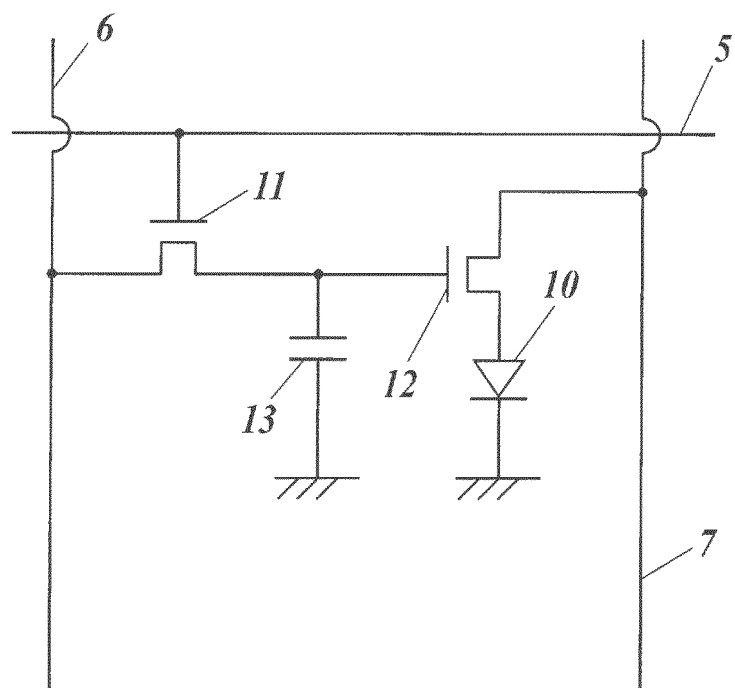
FIG. 11 is a schematic view illustrating a pixel circuit.

Next, an emission process of a pixel will be explained. FIG. 11 is a schematic drawing of a pixel.

A pixel is equipped with an organic EL element 10, a switching transistor 11, an operating transistor 12 and a capacitor 13. Red, green and blue emitting organic EL elements are utilized as the organic EL element 10 for plural pixels, and full-color display device is possible by arranging these side by side on the same substrate.

In FIG. 11, an image data signal is applied on the drain of the switching transistor 11 via the data line 6 from the control section B. Then when a scanning signal is applied on the gate of the switching transistor 11 via the scanning line 5 from control section B, operation of switching transistor is on to transmit the image data signal applied on the drain to the gates of the capacitor 13 and the operating transistor 12.

The operating transistor 12 is on, simultaneously with the capacitor 13 being charged depending on the potential of an image data signal, by transmission of an image data signal. In the operating transistor 12, the drain is connected to an electric source line 7 and the source is connected to the electrode of the organic EL element 10, and an electric current is supplied from the electric source line 7 to the organic EL element 10 depending on the potential of an image data applied on the gate.

When a scanning signal is transferred to the next scanning line 5 by successive scanning of the control section B, operation of the switching transistor 11 is off.

However, since the capacitor 13 keeps the charged potential of an image data signal even when operation of the switching transistor 11 is off, operation of the operating transistor 12 is kept on to continue emission of the organic EL element 10 until the next scanning signal is applied.

When the next scanning signal is applied by successive scanning, the operating transistor 12 operates depending on the potential of an image data signal synchronized to the scanning signal and the organic EL element 10 emits light.

That is, emission of each organic EL element 10 of the plural pixels 3 is performed by providing the switching transistor 11 and the operating transistor 12 against each organic EL element 10 of plural pixels 3. Such an emission method is called as an active matrix mode.

Herein, emission of the organic EL element 10 may be either emission of plural gradations based on a multiple-valued image data signal having plural number of gradation potentials or on and off of a predetermined emission quantity based on a binary image data signal. Further, potential hold of the capacitor 13 may be either continuously maintained until the next scanning signal application or discharged immediately before the next scanning signal application.

In the present invention, emission operation is not necessarily limited to the above-described active matrix mode but may be a passive matrix mode in which organic EL element is emitted based on a data signal only when a scanning signal is scanned.

Figure 12:
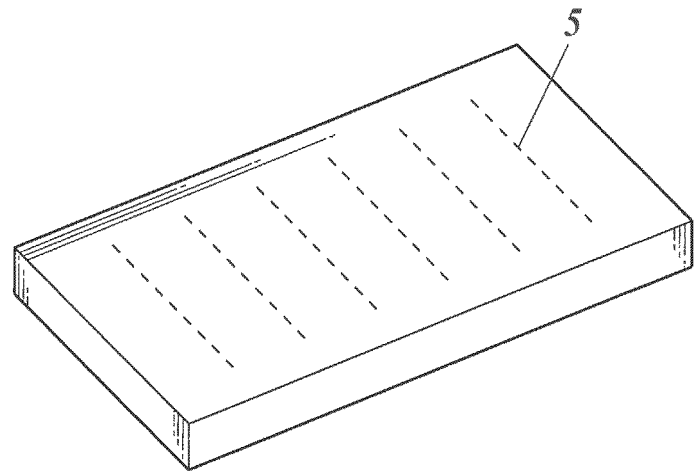
FIG. 12 is a schematic diagram of a display device by a passive matrix mode.
Figure 12:
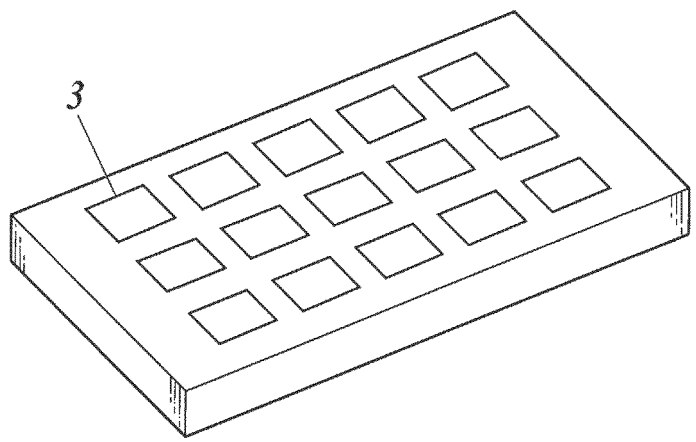
Figure 12:
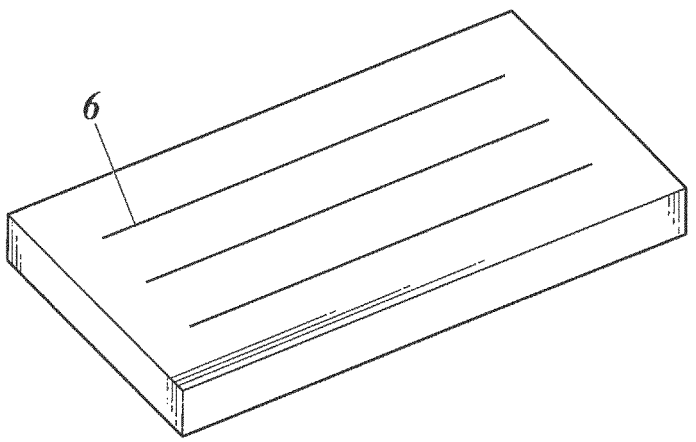

FIG. 12 is a schematic drawing of a display device based on a passive matrix mode. In FIG. 12, plural number of scanning lines 5 and plural number of image data lines 6 are arranged grid-wise, opposing to each other and sandwiching the pixels 3.

When a scanning signal of the scanning line 5 is applied by successive scanning, the pixel 3 connected to the scanning line 5 applied with the signal emits depending on an image data signal.

Since the pixel 3 is provided with no active element in a passive matrix mode, decrease of manufacturing cost is possible.

By employing the organic EL element of the present invention, it was possible to obtain a display device having improved emission efficiency.

<Light Emitting Device>

An organic EL element of the present invention may be used for a light emitting device.

An organic EL element of the present invention may be provided with a rasonator structure. The intended uses of the organic EL element provided with a rasonator structure are: a light source of a light memory media, a light source of an electrophotographic copier, a light source of a light communication processor, and a light source of a light sensor, however, it is not limited to them. It may be used for the above-described purposes by making to emit a laser.

Further, an organic EL element of the present invention may be used for a kind of lamp such as for illumination or exposure. It may be used for a projection device for projecting an image, or may be used for a display device to directly observe a still image or a moving image thereon.

The driving mode used for a display device of a moving image reproduction may be any one of a passive matrix mode and an active matrix mode. By employing two or more kinds of organic EL elements of the present invention emitting a different emission color, it may produce a full color display device.

In addition, a π-conjugated compound used in the present invention may be applicable to an organic EL element substantially emitting white light as a light emitting device. For example, when a plurality of light emitting materials are employed, white light may be obtained by mixing colors of a plurality of emission colors. As a combination of the plurality of emission colors, it may be a combination of red, green and blue having emission maximum wavelength of three primary colors, or it may be a combination of colors having two emission maximum wavelength making use of the relationship of two complementary colors of blue and yellow, or blue-green and orange.

A production method of an organic EL element of the present invention is done by placing a mask only during formation of a light emitting layer, a hole transport layer and an electron transport layer. It may be produced by coating with a mask to make simple arrangement. Since other layers are common, there is no need of pattering with a mask. For example, it may produce an electrode uniformly with a vapor deposition method, a cast method, a spin coating method, an inkjet method, and a printing method. The production yield will be improved.

By using these methods, it may be produced a white organic EL device in which a plurality of light emitting elements are arranged in parallel to form an array state. The element itself emits white light.

[One Embodiment of Lighting Device of the Present Invention]

One embodiment of lighting devices of the present Invention provided with an organic EL element of the present invention will be described.

The non-light emitting surface of the organic EL element of the present invention was covered with a glass case, and a 300 μm thick glass substrate was employed as a sealing substrate. An epoxy based light curable type adhesive (LUXTRACK LC0629B produced by Toagosei Co., Ltd.) was employed in the periphery as a sealing material. The resulting one was superimposed on the aforesaid cathode to be brought into close contact with the aforesaid transparent support substrate, and curing and sealing were carried out via exposure of UV radiation onto the glass substrate side, whereby the lighting device shown in FIG. 13 and FIG. 14, was formed.

Figure 13:
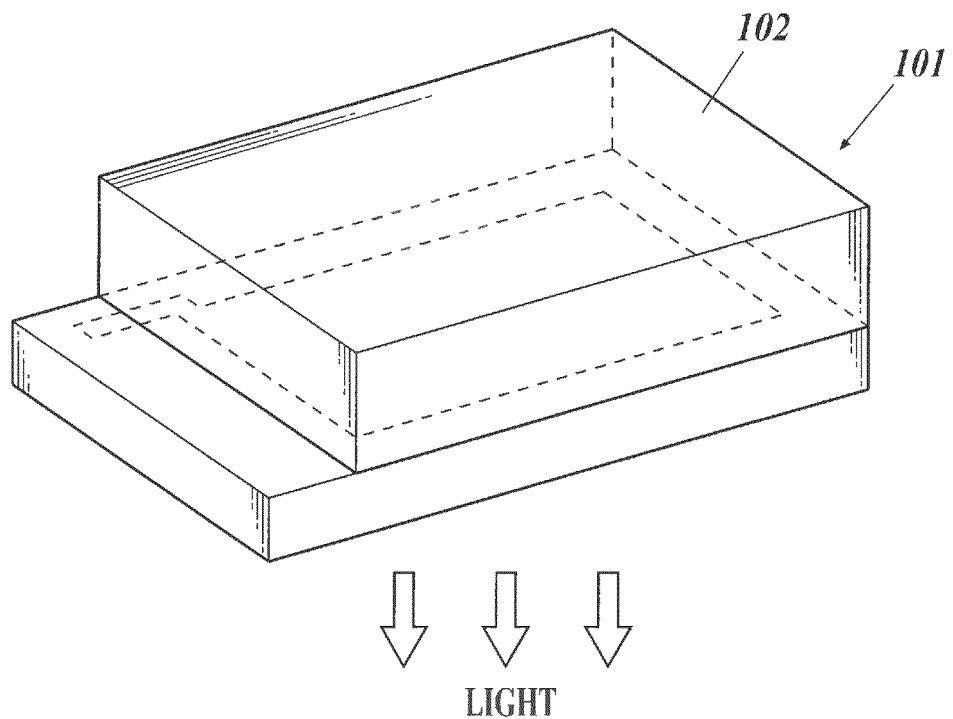
FIG. 13 is a schematic view of a lighting device.

FIG. 13 is a schematic view of a lighting device, and an organic EL element of the present invention (Organic EL element 101 in a light emitting device) is covered with glass cover 102 (incidentally, sealing by the glass cover was carried out in a globe box under nitrogen ambience (under an ambience of high purity nitrogen gas at a purity of at least 99.999%) so that Organic EL Element 101 was not brought into contact with atmosphere).

Figure 6:
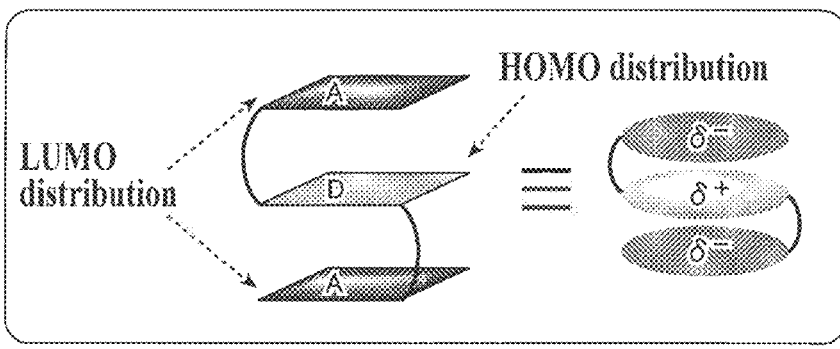
FIG. 6 is a schematic diagram illustrating an interaction of a π-conjugated compound of the present invention and a medium.
Figure 6:
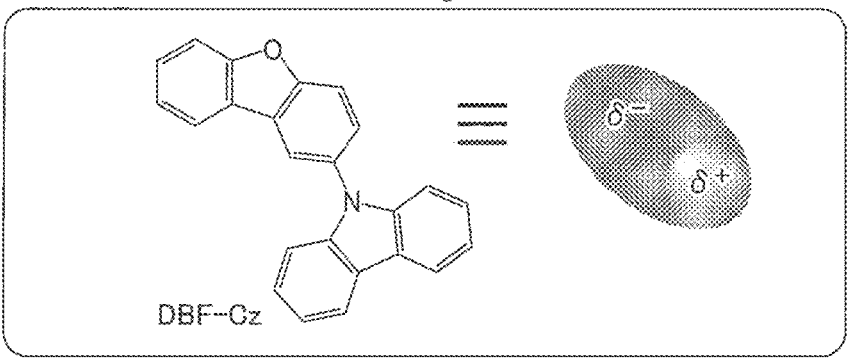
Figure 6:
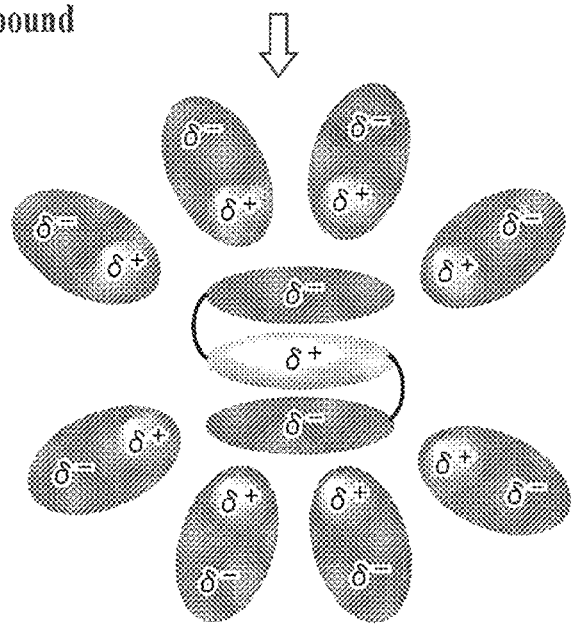
Figure 14:
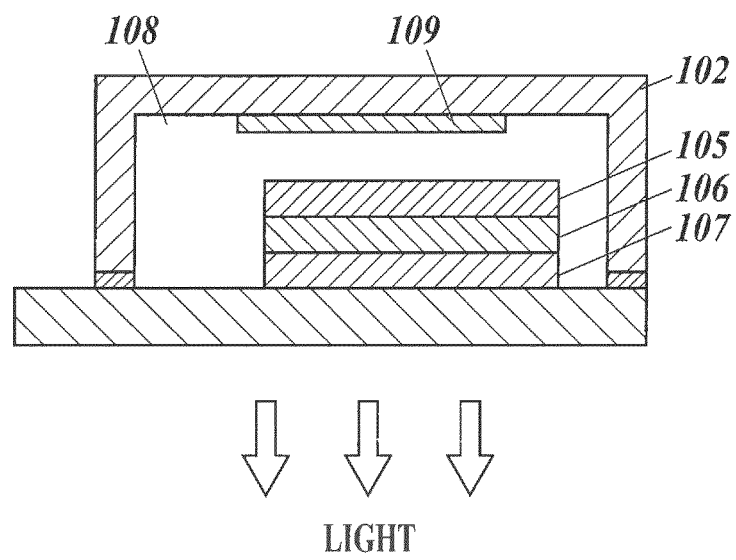
FIG. 14 is a cross-sectional diagram of a lighting device.

FIG. 14 is a cross-sectional view of a lighting device. In FIG. 6, 105 represents a cathode, 106 represents an organic EL layer, and 107 represents a glass substrate fitted with a transparent electrode. Further, the interior of glass cover 102 is filled with nitrogen gas 108 and water catching agent 109 is provided.

By employing an organic EL element of the present invention, it was possible to obtain a light emitting having improved emission efficiency.

<Light-emitting Thin Film>

A light-emitting thin film of the present invention is characterized in containing a π-conjugated compound according to the above-described present invention. It may be produced in the same way as preparation of the above-described organic layer.

Forming methods of a light-emitting thin film according to the present invention are not specifically limited. They may be formed by using a known method such as a vacuum vapor deposition method and a wet method (wet process).

Examples of a wet process include: a spin coating method, a cast method, an inkjet method, a printing method, a die coating method, a blade coating method, a roll coating method, a spray coating method, a curtain coating method, and a LB method (Langmuir Blodgett method). From the viewpoint of getting a uniform thin layer with high productivity, preferable are methods highly appropriate to a roll-to-roll method such as a die coating method, a roll coating method, an inkjet method, and a spray coating method.

Examples of a liquid medium to dissolve or to disperse a π-conjugated compound according to the present invention include: ketones such as methyl ethyl ketone and cyclohexanone; aliphatic esters such as ethyl acetate; halogenated hydrocarbons such as dichlorobenzene; aromatic hydrocarbons such as toluene, xylene, mesitylene, and cyclohexylbenzene; aliphatic hydrocarbons such as cyclohexane, decalin, and dodecane; organic solvents such as DMF and DMSO.

These will be dispersed with a dispersion method such as an ultrasonic dispersion method, a high shearing dispersion method and a media dispersion method.

A different film forming method may be applied to every organic layer. When a vapor deposition method is adopted for forming each layer, the vapor deposition conditions will change depending on the compounds used. Generally, the following ranges are suitably selected for the conditions, heating temperature of boat: 50 to 450° C., level of vacuum: $1 \times 10^{-6}$ to $1 \times 10^{-2}$ Pa, vapor deposition rate: 0.01 to 50 nm/sec, temperature of substrate: −50 to 300° C., and layer thickness: 0.1 nm to 5 μm, preferably 5 to 200 nm.

When a spin coating method is adopted, it is preferable to use a spin coater in the range of 100 to 1000 rpm for 10 to 120 seconds under a dry inert gas atmosphere.

A light-emitting thin film of the present invention may be used for a display device or a light emitting device.

EXAMPLES

Hereafter, the present invention will be described specifically by referring to examples, however, the present invention is not limited to them. In examples, the indication of "%" is used. Unless particularly mentioned, it represents "mass %".

Figure 15:
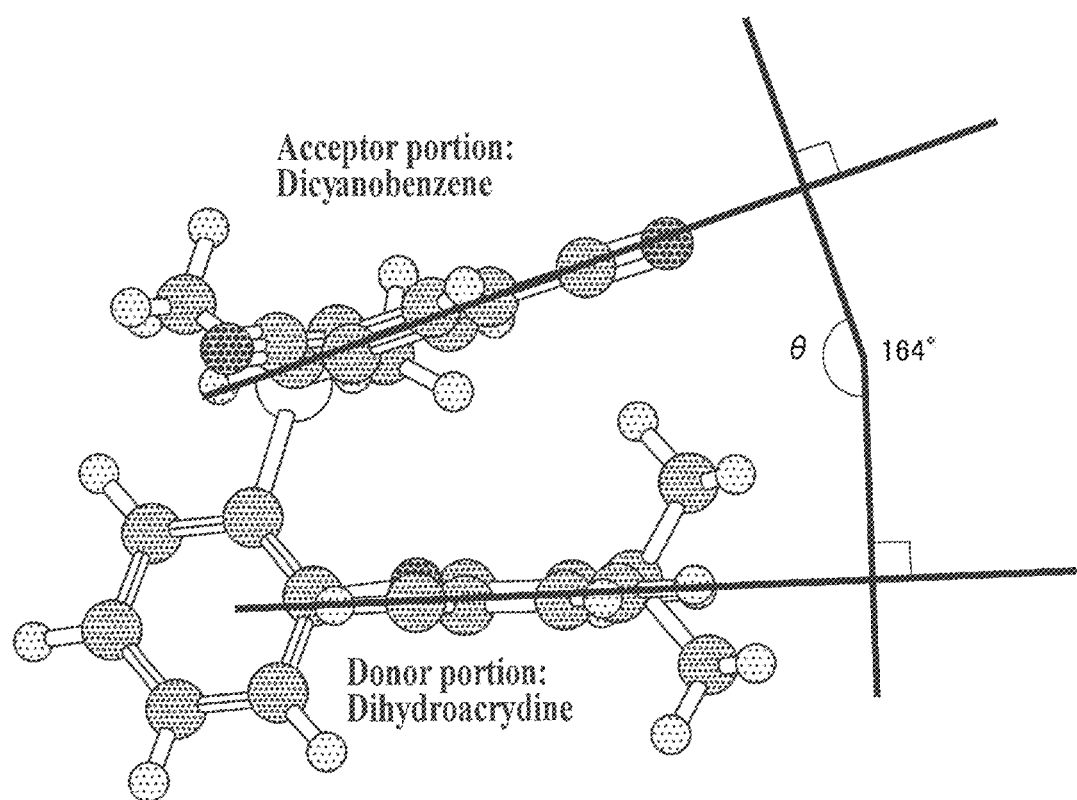
FIG. 15 is a schematic diagram illustrating a calculation method of an angle θ of the present invention.

A calculation method of an angle θ in Examples will be described by referring to a compound T-93 as an example. The compound T-93 was calculated by performing an optimization of a structure with a density-functional calculation method using B3LYP as a functional and 6-31G(d) as a base function. The theoretical calculation results revealed that a LUMO is localized at a dicyanobenzene being an acceptor portion, and a HOMO is localized at a 9,10-dihydroacridine portion being a donor portion. Since the frontier orbitals of the compound T-93 are a π*-orbital and a π-orbital, as described above, a vertical direction to the π-conjugated plane is a direction vector of the LUMO orbital and the HOMO orbital defined in the present invention (refer to FIG. 15). By using the optimized structure obtained by the theoretical calculation, the angle θ formed with two direction vectors was calculated to be 164 degree for the compound T-93.

Example 1

(Preparation of Organic EL Element 1-1)

An anode was prepared on a glass substrate of 50 mm×50 mm with a thickness of 0.7 mm by forming a film of ITO (indium tin oxide) with a thickness of 150 nm, then by making patterning to it. The transparent support substrate provided with the ITO transparent electrode was subjected to ultrasonic washing with isopropyl alcohol, followed by drying with desiccated nitrogen gas, and it was subjected to UV ozone washing for 5 minutes. The transparent support substrate was fixed to a substrate holder of a commercial vacuum deposition apparatus.

The constituting materials for each layer were loaded in each heating boat for vapor deposition in the vacuum deposition apparatus with an optimum amount. As a heating boat for vapor deposition, it was used a resistance heating boat made of molybdenum or tungsten.

After reducing the pressure of a vacuum tank to $4 \times 10^{-4}$ Pa, the heating boat containing HAT-CN (1,4,5,8,9,12-hexaazatriphenylene hexacarbonitrile) was heated via application of electric current and vapor deposition was made onto the ITO transparent electrode at a deposition rate of 0.1 nm/second, whereby it was produced a hole injection layer having a thickness of 10 nm.

Subsequently, α-NPD (4,4'-bis[N-(naphthyl)-N-phenylamino]biphenyl) was deposited onto the hole injection layer at a deposition rate of 0.1 nm/second, whereby it was produced a hole transport layer having a thickness of 40 nm.

Further, a host compound mCP (1,3-bis(N-carbazolyl)benzene) and a comparative compound 1 were co-deposited onto the hole transport layer at a deposition rate of 0.1 nm/second so that they have 96 volume % and 4 volume % respectively, whereby it was produced a light emitting layer having a thickness of 30 nm.

Subsequently, BCP (2,9-dimethyl-4,7-diphenyl-1,10-phenanthroline) was deposited at a deposition rate of 0.1 nm/second, whereby it was produced an electron transport layer having a thickness of 30 nm.

Further, after forming a lithium fluoride layer having a thickness of 0.5 nm, 110 nm thick aluminum was vapor deposited to form a cathode.

The non-light emitting surface side of the produced element was sealed by a glass case having a can shape under an ambience of high purity nitrogen gas having a purity of at least 99.999%. The electrode taken out wiring was set to obtain an organic EL element 1-1.

Comparative Compound 1

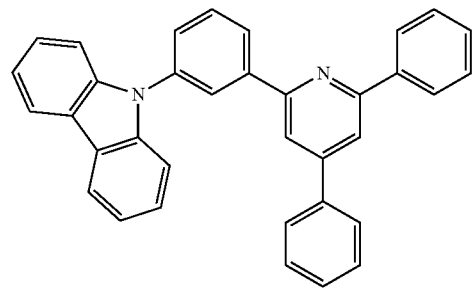

-continued

Comparative Compound 2

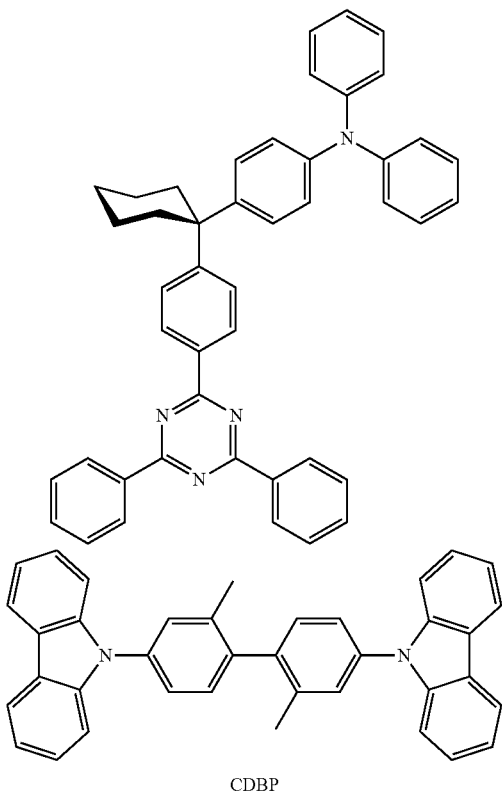

CDBP (Preparation of Organic EL Elements 1-2 to 1-9)

Organic EL elements 1-2 to 1-9 were prepared in the same manner as preparation of the organic EL element 1-1 except that the light emitting compound was changed from the comparative compound 1 to the compounds described in Table 1.

TABLE 1

| Organic EL element No. | Emission compound | Angle θ (degree) | $\Delta E_{ST}$ (eV) | Emission efficiency (%) | Remarks |
|---|---|---|---|---|---|
| 1-1 | Comparative compound 1 | 50 | 0.47 | 100 | Comp. |
| 1-2 | T-71 | 130 | 0.18 | 109 | Inv. |
| 1-3 | T-19 | 135 | 0.02 | 114 | Inv. |
| 1-4 | T-2 | 120 | 0.04 | 111 | Inv. |
| 1-5 | T-86 | 141 | 0.03 | 117 | Inv. |
| 1-6 | T-92 | 110 | 0.03 | 111 | Inv. |
| 1-7 | T-93 | 164 | 0.01 | 121 | Inv. |
| 1-8 | T-96 | 113 | 0.04 | 110 | Inv. |
| 1-9 | Comparative compound 2 | 71 | 0.07 | 103 | Comp. |

Comp.: Comparative example
Inv.: Inventive example

Example 2

(Preparation of Organic EL element 2-1)

An anode was prepared by making patterning to a glass substrate of 100 mm×100 mm×1.1 mm (NA45, produced by NH Techno Glass Corp.) on which ITO (indium tin oxide) was formed with a thickness of 100 nm. Thereafter, the above transparent support substrate provided with the ITO transparent electrode was subjected to ultrasonic washing with isopropyl alcohol, followed by drying with desiccated nitrogen gas, and it was subjected to UV ozone washing for 5 minutes.

On the transparent support substrate thus prepared was applied a 70% solution of poly (3,4-ethylenedioxythiphene)-polystyrene sulfonate (PEDOT/PSS, Baytron P AI4083, made by Bayer AG.) diluted with water by using a spin coating method at 3,000 rpm for 30 seconds to forma film, and then it was dried at 200° C. for one hour. A hole injection layer having a thickness of 20 nm was prepared. The resulting transparent support substrate was fixed to a substrate holder of a commercial vacuum deposition apparatus. The constituting materials for each layer were loaded in each heating boat for vapor deposition in the vacuum deposition apparatus with an optimum amount. As a heating boat for vapor deposition, it was used a resistance heating boat made of molybdenum or tungsten.

After reducing the pressure of a vacuum tank to $4 \times 10^{-4}$ Pa, α-NPD was deposited onto the hole injection layer at a deposition rate of 0.1 nm/second, whereby it was produced a hole transport layer having a thickness of 40 nm.

CDBP and perylene were co-deposited onto the hole transport layer at a deposition rate of 0.1 nm/second so that they have 94 volume % and 6 volume % respectively, whereby it was produced a light emitting layer having a thickness of 30 nm.

Subsequently, TPBi (1,3,5-tris(N-benzimidazole-2-yl)) was deposited at a deposition rate of 0.1 nm/second, whereby it was produced an electron transport layer having a thickness of 30 nm.

Further, after forming a lithium fluoride layer having a thickness of 0.5 nm, 110 nm thick aluminum was vapor deposited to form a cathode.

The non-light emitting surface side of the produced element was sealed by a glass case having a can shape under an ambience of high purity nitrogen gas having a purity of at least 99.999%. The electrode taken out wiring was set to obtain an organic EL element 2-1.

(Preparation of Organic EL Element 2-2)

Organic EL elements 2-2 was prepared in the same manner as preparation of the organic EL element 2-1 except that the light emitting layer was formed by using: CDBP as a host compound; perylene as a light emitting compound; and the comparative compound 1 as a third compound, and the contents of compounds were respectively adjusted to be 80 volume %, 6 volume %, and 14 volume %.

(Preparation of Organic EL elements 2-3 to 2-9)

Organic EL elements 2-3 to 2-9 were prepared in the same manner as preparation of the organic EL element 2-2 except that the third compound was changed as indicated in Table 2.

TABLE 2

| Organic EL element No. | Third component | Angle θ (degree) | $\Delta E_{ST}$ (eV) | Emission efficiency (%) | Remarks |
|---|---|---|---|---|---|
| 2-1 | None | — | — | 100 | Comp. |
| 2-2 | Comparative compound 1 | 50 | 0.47 | 105 | Comp. |
| 2-3 | T-71 | 130 | 0.18 | 115 | Inv. |
| 2-4 | T-19 | 135 | 0.02 | 119 | Inv. |
| 2-5 | T-2 | 120 | 0.04 | 118 | Inv. |
| 2-6 | T-86 | 141 | 0.03 | 125 | Inv. |
| 2-7 | T-93 | 164 | 0.01 | 130 | Inv. |

TABLE 2-continued

| Organic EL element No. | Third component | Angle θ (degree) | $\Delta E_{ST}$ (eV) | Emission efficiency (%) | Remarks |
|---|---|---|---|---|---|
| 2-8 | Comparative compound 2 | 71 | 0.07 | 108 | Comp. |
| 2-9 | T-110 | 120 | 0.01 | 112 | Inv. |

Comp.: Comparative example
Inv.: Inventive example

Example 3

(Preparation of Organic EL Element 3-1)

An anode was prepared on a glass substrate of 50 mm×50 mm with a thickness of 0.7 mm by forming a film of ITO (indium tin oxide) with a thickness of 150 nm, then by making patterning to it. The transparent support substrate provided with the ITO transparent electrode was subjected to ultrasonic washing with isopropyl alcohol, followed by drying with desiccated nitrogen gas, and it was subjected to UV ozone washing for 5 minutes. The transparent support substrate was fixed to a substrate holder of a commercial vacuum deposition apparatus.

The constituting materials for each layer were loaded in each heating boat for vapor deposition in the vacuum deposition apparatus with an optimum amount. As a heating boat for vapor deposition, it was used a resistance heating boat made of molybdenum or tungsten.

After reducing the pressure of a vacuum tank to $4 \times 10^{-4}$ Pa, the heating boat containing HAT-CN (1,4,5,8,9,12-hexaazatriphenylene hexacarbonitrile) was heated via application of electric current and deposition was made onto the ITO transparent electrode at a deposition rate of 0.1 nm/second, whereby it was produced a hole injection layer having a thickness of 15 nm.

Subsequently, α-NPD (4,4'-bis[N-(naphthyl)-N-phenylamino]biphenyl) was deposited onto the hole injection layer at a deposition rate of 0.1 nm/second, whereby it was produced a hole transport layer having a thickness of 30 nm.

Subsequently, the heating boats each containing the comparative compound 1 as a host compound and tris (2-phenylpyridinate) iridium (III) were heated via application of electric current and co-deposition was made onto the hole transport layer at a deposition rate of 0.1 nm/second and 0.010 nm/second, whereby it was produced a light emitting layer having a thickness of 40 nm.

Subsequently, HB-1 was deposited at a deposition rate of 0.1 nm/second, whereby it was produced a first electron transport layer having a thickness of 5 nm.

HB-1

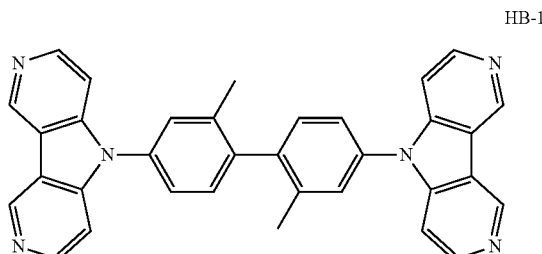

Further, ET-1 was deposited thereon at a deposition rate of 0.1 nm/second, whereby it was produced a second electron transport layer having a thickness of 45 nm.

ET-1

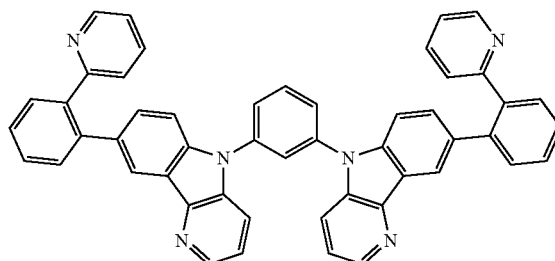

Further, after forming a lithium fluoride layer having a thickness of 0.5 nm, 100 nm thick aluminum was vapor deposited to form a cathode. Thus, an organic EL element 3-1 was prepared.

(Preparation of Organic EL Elements 3-2 to 3-7)

Organic EL elements 3-2 to 3-7 were prepared in the same manner as preparation of the organic EL element 3-1 except that the host compound was changed as indicated in Table 3.

In the same manner as described above, an emission luminance of the organic EL element 3-1 was measured. A relative emission luminance of each organic EL element was obtained with respect to the emission luminance of the organic EL element 3-1. The obtained measurement results are listed in Table 3.

TABLE 3

| Organic EL element No. | Host component | Angle θ (degree) | $\Delta E_{ST}$ (eV) | Emission efficiency (%) | Remarks |
|---|---|---|---|---|---|
| 3-1 | Comparative Compound 1 | 50 | 0.47 | 100 | Comp. |
| 3-2 | Comparative compound 2 | 71 | 0.07 | 87 | Comp. |
| 3-3 | T-71 | 130 | 0.18 | 115 | Inv. |
| 3-4 | T-86 | 141 | 0.03 | 118 | Inv. |
| 3-5 | T-93 | 164 | 0.01 | 123 | Inv. |
| 3-6 | T-97 | 142 | 0.18 | 117 | Inv. |
| 3-7 | T-101 | 110 | 0.01 | 109 | Inv. |

Comp.: Comparative example
Inv.: Inventive example (Measurement of Emission Efficiency)

Emission efficiency of an organic EL element sample during driving was evaluated by conducting the following measurement.

(Measurement of Emission Efficiency)

Each organic EL element thus produced was allowed to emit light by applying a constant electric current of 2.5 mA/cm² at room temperature (about 25° C.). The emission luminance immediately after starting to emit light was measured with Spectroradiometer CS-2000 (produced by Konica Minolta, Inc.). The emission efficiency was determined. The obtained results were indicated as a relative value in Tables 1 to 3.

In Example 1, the indicated values were a relative value when the emission efficiency of the organic EL element 1-1 was set to be 100%. In Example 2, the indicated values were a relative value when the emission efficiency of the organic EL element 2-1 was set to be 100%. Further, in Example 3, the indicated values were a relative value when the emission efficiency of the organic EL element 3-1 was set to be 100%.

CONCLUSION

An absolute value of the difference between the first (lowest) singlet excited level and the first (lowest) triplet excited level ($\Delta E_{ST}$) was calculated based on an optimized structure for calculation of an angle θ. The calculation of the excited state was done using Time-dependent density-functional calculation method (DFT) with Gaussian 09 using B3LYP as a functional and 6-31G(d) as a base function.

In Table 1, the organic EL elements 1-2 to 1-8 had a larger θ value and a smaller $\Delta E_{ST}$ value compared with the organic EL elements 1-1 and 1-9. It was shown that the organic EL elements 1-2 to 1-8 exhibited improved emission efficiency.

In Table 2, it was shown that the organic EL elements 2-2 and 2-8 containing a third component exhibited improved emission efficiency compared with the organic EL elements 2-1. It was shown that the organic EL elements 2-3 to 2-7 and 2-9 containing a third component having a larger angle θ exhibited further improved emission efficiency compared with the organic EL elements 2-1.

In Table 3, it was shown that the organic EL elements 3-3 and 3-7 had a larger θ value and a smaller $\Delta E_{ST}$ value compared with the organic EL elements 3-1 and 3-2. The organic EL elements 3-3 and 3-7 exhibited improved emission efficiency.

INDUSTRIAL APPLICABILITY

As described above, the present invention is suitable to provide an organic electroluminescent element enabling to achieve restrained broadening of an absorption spectrum and an emission spectrum, and high emission efficiency without using a rare metal.

DESCRIPTION OF SYMBOLS

1: Display
3: Pixel
5: Scanning line
6: Data line
7: Electric source line
10: Organic EL element
11: Switching transistor
12: Operating transistor
13: Capacitor
101: Organic EL element in a light emitting device
102: Glass cover
105: Cathode
106: Organic EL layer
107: Glass substrate having a transparent electrode
108: Nitrogen gas
109: Water catching agent
A: Display section
B: Control section
C: Wiring section

The invention claimed is:

1. An organic electroluminescent element comprising an organic layer interposed between an anode and a cathode, the organic layer containing at least one light emitting layer, wherein the at least one light emitting layer contains a π-conjugated compound having an electron donor portion and an electron acceptor portion in the molecule; the π-conjugated compound has a direction vector from an atom having a HOMO orbital in the electron donor portion to an electron cloud of the HOMO orbital, and a direction vector from an atom having a LUMO orbital in the electron acceptor portion to an electron cloud of the LUMO orbital, and the two direction vectors form an angle θ in the range of 90 to 180 degrees; and the π-conjugated compound has a plurality of the electron donor portions or a plurality of the electron acceptor portions, and the π-conjugated compound is represented by Formula (3) or Formula (6):

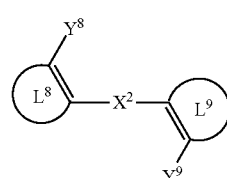

Formula (3)

Formula (6)

wherein $X^3$, $X^6$, $Y^8$, $Y^9$, $Y^{17}$, and $Y^{18}$ each respectively represent the electron donor portion or the electron acceptor portion,
$X^3$, $X^6$, $Y^8$, $Y^9$, $Y^{17}$, and $Y^{18}$ each respectively are one selected from the group consisting of an aryl group which may have a substituent, a heteroaryl group which may have a substituent, a carbonyl group which may have a substituent, a nitrogen atom which may have a substituent, a boron atom which may have a substituent, a phosphor atom which may have a substituent, and a silicon atom which may have a substituent, and
$L^8$ and $L^9$ represent a linking group, $L^8$ and $L^9$ each respectively represent an aryl group which may have a substituent or a heteroaryl group which may have a substituent, $L^8$ binds $X^3$ and $Y^8$ through adjacent carbon atoms, $L^9$ binds $X^3$ and $Y^9$ through adjacent carbon atoms, and
wherein the π-conjugated compound is not represented by Formula (2):

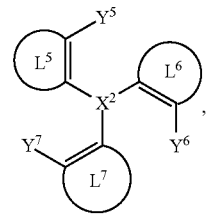

wherein $X^2$ and $Y^5$ to $Y^7$ each respectively represent the electron donor portion or the electron acceptor portion; when $X^2$ represents the electron donor portion, $Y^5$ to $Y^7$ each respectively represent the electron acceptor portion; when $X^2$ represents the electron acceptor portion, $Y^5$ to $Y^7$ each respectively represent the electron donor portion; $L^5$ to $L^7$ each represent a linking group, $L^5$ to $L^7$ each respectively represent an aryl group which may have a substituent or a heteroaryl group which may have a substituent, $L^5$ binds $X^2$ and $Y^5$ through adjacent carbon atoms, $L^6$ binds $X^2$ and $Y^6$ through adjacent carbon atoms, $L^7$ binds $X^2$ and $Y^7$ through adjacent carbon atoms.

2. The organic electroluminescent element described in claim 1,
wherein the angle θ is in the range of 135 to 180 degrees.

3. The organic electroluminescent element described in claim 1,
wherein one of the electron acceptor portions is bonded to two or more electron donor portions through the linking group, or one of the electron donor portions is bonded to two or more electron acceptor portions through the linking group.

4. The organic electroluminescent element described in claim 1,
wherein one of the electron acceptor portions is directly bonded to two or more electron donor portions, or one of the electron donor portions is directly bonded to two or more electron acceptor portions.

5. The organic electroluminescent element described in claim 1,
wherein $L^8$ and $L^9$ in Formula (3) each are a benzene ring.

6. The organic electroluminescent element described in claim 1,
wherein an absolute value of a difference between a lowest excited singlet energy level and a lowest triplet energy level ($\Delta E_{ST}$) is 0.5 eV or less.

7. The organic electroluminescent element described in claim 1,
wherein the at least one light emitting layer contains: the π-conjugated compound; and at least one of a fluorescent compound and a phosphorescent compound.

8. The organic electroluminescent element described in claim 1,
wherein the at least one light emitting layer contains: the π-conjugated compound; at least one of a fluorescent compound and a phosphorescent compound; and a host compound.

9. A display device provided with the organic electroluminescent element described in claim 1.

10. A lighting device provided with the organic electroluminescent element described in claim 1.

11. A π-conjugated compound having an electron donor portion and an electron acceptor portion in the molecule,
wherein the π-conjugated compound has a direction vector from an atom having a HOMO orbital in the electron donor portion to an electron cloud of the HOMO orbital, and a direction vector from an atom having a LUMO orbital in the electron acceptor portion to an electron cloud of the LUMO orbital, and the two direction vectors form an angle θ in the range of 90 to 180 degrees; and the π-conjugated compound has a plurality of the electron donor portions or a plurality of the electron acceptor portions, and the π-conjugated compound is represented by Formula (3) or Formula (6):

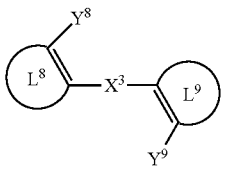

Formula (3)

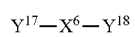

Formula (6)

wherein $X^3$, $X^6$, $Y^8$, $Y^9$, $Y^{17}$, and $Y^{18}$ each respectively represent the electron donor portion or the electron acceptor portion, and
$X^3$, $X^6$, $Y^8$, $Y^9$, $Y^{17}$, and $Y^{18}$ each respectively are one selected from the group consisting of an aryl group which may have a substituent, a heteroaryl group which may have a substituent, a carbonyl group which may have a substituent, a nitrogen atom which may have a substituent, a boron atom which may have a substituent, a phosphor atom which may have a substituent, and a silicon atom which may have a substituent, and
$L^8$ and $L^9$ represent a linking group, $L^8$ and $L^9$ each respectively represent an aryl group which may have a substituent or a heteroaryl group which may have a substituent, $L^8$ binds $X^3$ and $Y^8$ through adjacent carbon atoms, $L^9$ binds $X^3$ and $Y^9$ through adjacent carbon atoms, and
wherein the π-conjugated compound is not represented by Formula (2):

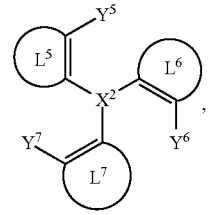

wherein $X^2$ and $Y^5$ to $Y^7$ each respectively represent the electron donor portion or the electron acceptor portion; when $X^2$ represents the electron donor portion, $Y^5$ to $Y^7$ each respectively represent the electron acceptor portion; when $X^2$ represents the electron acceptor portion, $Y^5$ to $Y^7$ each respectively represent the electron donor portion; $L^5$ to $L^7$ represent a linking group, $L^5$ to $L^7$ each respectively represent an aryl group which may have a substituent or a heteroaryl group which may have a substituent, $L^5$ binds $X^2$ and $Y^5$ through adjacent carbon atoms, $L^6$ binds $X^2$ and $Y^6$ through adjacent carbon atoms, $L^7$ binds $X^2$ and $Y^7$ through adjacent carbon atoms.

12. A light-emitting thin film containing the π-conjugated compound described in claim 11.

* * * * *